(12) United States Patent
Cartledge et al.

(10) Patent No.: US 11,083,576 B2
(45) Date of Patent: Aug. 10, 2021

(54) ACTIVELY CONTROLLABLE HEART VALVE IMPLANT AND METHOD OF CONTROLLING SAME

(71) Applicant: Edwards Lifesciences CardiAQ LLC, Irvine, CA (US)

(72) Inventors: Richard George Cartledge, Boca Raton, FL (US); Derek Dee Deville, Coral Gables, FL (US); Kevin W. Smith, Coral Gables, FL (US); James L. Greene, Warwickshire (GB); Jorge H. Jimenez, Atlanta, GA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 245 days.

(21) Appl. No.: 16/275,769

(22) Filed: Feb. 14, 2019

(65) Prior Publication Data

US 2019/0175341 A1 Jun. 13, 2019

Related U.S. Application Data

(63) Continuation of application No. 15/189,786, filed on Jun. 22, 2016, now Pat. No. 10,226,335.
(Continued)

(51) Int. Cl.
*A61F 2/24* (2006.01)

(52) U.S. Cl.
CPC .......... *A61F 2/2418* (2013.01); *A61F 2/2436* (2013.01); *A61F 2/2412* (2013.01);
(Continued)

(58) Field of Classification Search
CPC .......... A61F 2/82; A61F 2/852; A61F 2/2418; A61F 2/24; A61F 2/2412
See application file for complete search history.

(56) References Cited

U.S. PATENT DOCUMENTS

| 3,657,744 A | 4/1972 | Ersek |
| 3,671,979 A | 6/1972 | Moulopoulos |

(Continued)

FOREIGN PATENT DOCUMENTS

| CA | 2304325 A1 | 10/2000 |
| CA | 2827556 A1 | 7/2012 |

(Continued)

OTHER PUBLICATIONS

Bavaria, Joseph E. M.D. et al.: "Transcatheter Mitral Valve Implantation: The Future Gold Standard for MR?," Applicant requests the Examiner to consider this reference to be prior art as of Dec. 2010.
(Continued)

*Primary Examiner* — Bruce E Snow
(74) *Attorney, Agent, or Firm* — Klarquist Sparkman LLP

(57) ABSTRACT

A method of implanting a replacement mitral valve can include expanding a replacement mitral valve to a first expanded configuration. The replacement mitral valve can include a force-expanding mitral valve lattice and a self-expanding valve trampoline lattice. The mitral valve lattice has an inflow end portion and an outflow end portion, and the valve trampoline lattice is attached to the outflow end portion of the mitral valve lattice. The method can also include rotating a plurality of jack screws connected to the mitral valve lattice. The jack screws can be configured to expand the mitral valve lattice from the first expanded configuration to a second expanded configuration.

20 Claims, 39 Drawing Sheets

Related U.S. Application Data

(60) Provisional application No. 62/183,451, filed on Jun. 23, 2015, provisional application No. 62/182,820, filed on Jun. 22, 2015.

(52) U.S. Cl.
CPC ............... *A61F 2220/0016* (2013.01); *A61F 2230/0006* (2013.01); *A61F 2230/0034* (2013.01); *A61F 2230/0052* (2013.01); *A61F 2250/001* (2013.01); *A61F 2250/0039* (2013.01); *A61F 2250/0048* (2013.01)

(56) References Cited

U.S. PATENT DOCUMENTS

| | | |
|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,777,951 A | 10/1988 | Cribier et al. |
| 4,865,600 A | 9/1989 | Carpentier et al. |
| 4,994,077 A | 2/1991 | Dobben |
| 5,326,371 A | 7/1994 | Love et al. |
| 5,332,402 A | 7/1994 | Teitelbaum |
| 5,370,685 A | 12/1994 | Stevens |
| 5,415,667 A | 5/1995 | Frater |
| 5,545,214 A | 8/1996 | Stevens |
| 5,554,183 A | 9/1996 | Nazari |
| 5,554,185 A | 9/1996 | Block et al. |
| 5,697,382 A | 12/1997 | Love et al. |
| 5,797,951 A | 8/1998 | Mueller |
| 5,840,081 A | 11/1998 | Andersen et al. |
| 5,855,601 A | 1/1999 | Bessler et al. |
| 5,957,949 A | 9/1999 | Leonhardt et al. |
| 6,086,612 A | 7/2000 | Jansen |
| 6,113,631 A | 9/2000 | Jansen |
| 6,168,614 B1 | 1/2001 | Andersen et al. |
| 6,224,626 B1 | 5/2001 | Steinke |
| 6,251,093 B1 | 6/2001 | Valley et al. |
| 6,267,783 B1 | 7/2001 | Letendre et al. |
| 6,312,465 B1 | 11/2001 | Griffin et al. |
| 6,358,277 B1 | 3/2002 | Duran |
| 6,440,164 B1 | 8/2002 | DiMatteo et al. |
| 6,458,153 B1 | 10/2002 | Bailey et al. |
| 6,482,228 B1 | 11/2002 | Norred |
| 6,527,800 B1 | 3/2003 | McGuckin, Jr. et al. |
| 6,558,396 B1 | 5/2003 | Inoue |
| 6,582,462 B1 | 6/2003 | Andersen et al. |
| 6,610,088 B1 | 8/2003 | Gabbay |
| 6,629,534 B1 | 10/2003 | St. Goar et al. |
| 6,652,578 B2 | 11/2003 | Bailey et al. |
| 6,656,215 B1 | 12/2003 | Yanez et al. |
| 6,669,720 B1 | 12/2003 | Pierce |
| 6,676,698 B2 | 1/2004 | McGuckin, Jr. et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,716,230 B2 | 4/2004 | Whitman |
| 6,729,356 B1 | 5/2004 | Baker et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,746,422 B1 | 6/2004 | Noriega et al. |
| 6,749,560 B1 | 6/2004 | Konstorum et al. |
| 6,761,733 B2 | 7/2004 | Chobotov et al. |
| 6,767,362 B2 | 7/2004 | Schreck |
| 6,773,456 B1 | 8/2004 | Gordon et al. |
| 6,780,200 B2 | 8/2004 | Jansen |
| 6,790,229 B1 | 9/2004 | Berreklouw |
| 6,790,230 B2 | 9/2004 | Beyersdorf et al. |
| 6,860,900 B2 | 3/2005 | Clerc et al. |
| 6,875,231 B2 | 4/2005 | Anduiza et al. |
| 6,890,350 B1 | 5/2005 | Walak |
| 6,893,460 B2 | 5/2005 | Spenser et al. |
| 6,908,481 B2 | 6/2005 | Cribier |
| 6,929,659 B2 | 8/2005 | Pinchuk |
| 6,945,994 B2 | 9/2005 | Austin et al. |
| 6,951,571 B1 | 10/2005 | Srivastava |
| 7,007,396 B2 | 3/2006 | Rudko et al. |
| 7,011,681 B2 | 3/2006 | Vesely |
| 7,018,406 B2 | 3/2006 | Seguin et al. |
| 7,041,132 B2 | 5/2006 | Quijano et al. |
| 7,090,688 B2 | 8/2006 | Nishtala et al. |
| 7,097,658 B2 | 8/2006 | Oktay |
| 7,141,063 B2 | 11/2006 | White et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,553,324 B2 | 6/2009 | Andreas et al. |
| 7,585,321 B2 | 9/2009 | Cribier |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,748,389 B2 | 7/2010 | Salahieh et al. |
| 7,753,949 B2 | 7/2010 | Lamphere et al. |
| 7,803,185 B2 | 9/2010 | Gabbay |
| 7,806,919 B2 | 10/2010 | Bloom et al. |
| 7,815,673 B2 | 10/2010 | Bloom et al. |
| 7,824,443 B2 | 11/2010 | Salahieh et al. |
| 7,892,281 B2 | 2/2011 | Seguin et al. |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,934 B2 | 5/2012 | Styrc et al. |
| 8,182,528 B2 | 5/2012 | Salahieh et al. |
| 8,182,530 B2 | 5/2012 | Huber |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,493 B2 | 7/2012 | Boyle et al. |
| 8,226,710 B2 | 7/2012 | Nguyen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,036 B2 | 8/2012 | Cartledge et al. |
| 8,252,051 B2 | 8/2012 | Chau et al. |
| 8,252,052 B2 | 8/2012 | Salahieh et al. |
| 8,287,584 B2 | 10/2012 | Salahieh et al. |

(56) References Cited

U.S. PATENT DOCUMENTS

| | | |
|---|---|---|
| 8,303,653 B2 | 11/2012 | Bonhoeffer et al. |
| 8,313,525 B2 | 11/2012 | Tuval et al. |
| 8,323,335 B2 | 12/2012 | Rowe et al. |
| 8,353,953 B2 | 1/2013 | Giannetti et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |
| 8,617,236 B2 | 12/2013 | Paul et al. |
| 8,640,521 B2 | 2/2014 | Righini et al. |
| 8,647,378 B2 | 2/2014 | Mews et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,673,000 B2 | 3/2014 | Tabor et al. |
| 8,673,001 B2 | 3/2014 | Cartledge et al. |
| 8,679,174 B2 | 3/2014 | Ottma et al. |
| 8,679,404 B2 | 3/2014 | Liburd et al. |
| 8,685,080 B2 | 4/2014 | White |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,818 B2 | 7/2014 | Gregg |
| 8,771,344 B2 | 7/2014 | Tran et al. |
| 8,771,345 B2 | 7/2014 | Tuval et al. |
| 8,771,346 B2 | 7/2014 | Tuval et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,356 B2 | 8/2014 | Quadri et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,845,718 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,951,299 B2 | 2/2015 | Paul et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,992,608 B2 | 3/2015 | Haug et al. |
| 8,998,979 B2 | 4/2015 | Seguin et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,220,594 B2 | 12/2015 | Braido et al. |
| 9,241,790 B2 | 1/2016 | Lane et al. |
| 9,248,014 B2 | 2/2016 | Lane et al. |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,289,296 B2 | 3/2016 | Braido et al. |
| 9,295,551 B2 | 3/2016 | Straubinger et al. |
| 9,301,860 B2 | 4/2016 | White |
| 9,326,815 B2 | 5/2016 | Watson |
| 9,331,328 B2 | 5/2016 | Eberhardt et al. |
| 9,339,382 B2 | 5/2016 | Tabor et al. |
| 9,351,831 B2 | 5/2016 | Braido et al. |
| 9,351,832 B2 | 5/2016 | Braido et al. |
| 9,364,321 B2 | 6/2016 | Alkhatib et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,700,329 B2 | 7/2017 | Metzger et al. |
| 9,700,411 B2 | 7/2017 | Klima et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 10,022,221 B2 | 7/2018 | Gainor et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0077695 A1 | 6/2002 | Swanson et al. |
| 2003/0105517 A1 | 6/2003 | White et al. |
| 2003/0120331 A1 | 6/2003 | Chobotov et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |

(56) References Cited

U.S. PATENT DOCUMENTS

| | | |
|---|---|---|
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0173527 A1 | 8/2006 | Scherrible |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0009746 A1 | 1/2008 | Forster et al. |
| 2008/0021546 A1 | 1/2008 | Patz et al. |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208327 A1 | 8/2008 | Rowe |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0030501 A1 | 1/2009 | Morris et al. |
| 2009/0099653 A1 | 4/2009 | Suri et al. |
| 2009/0138079 A1 | 5/2009 | Tuval et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0292350 A1 | 11/2009 | Eberhardt et al. |
| 2009/0306768 A1 | 12/2009 | Quadri |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0004296 A1 | 1/2011 | Lutter et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0218619 A1 | 9/2011 | Benichou et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2012/0022639 A1 | 1/2012 | Hacohen et al. |
| 2012/0041550 A1 | 2/2012 | Salahieh et al. |
| 2012/0059454 A1 | 3/2012 | Millwee et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2012/0323316 A1 | 12/2012 | Chau et al. |
| 2013/0006294 A1 | 1/2013 | Kashkarov et al. |
| 2013/0035759 A1 | 2/2013 | Gross et al. |
| 2013/0046373 A1 | 2/2013 | Cartledge et al. |
| 2013/0053950 A1 | 2/2013 | Rowe et al. |
| 2013/0131788 A1 | 5/2013 | Quadri et al. |
| 2013/0144378 A1 | 6/2013 | Quadri et al. |
| 2013/0166017 A1* | 6/2013 | Cartledge ............... A61F 2/93 623/1.15 |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0296962 A1 | 11/2013 | Keel et al. |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214159 A1* | 7/2014 | Vidlund ............... A61L 27/34 623/2.14 |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |

(56) References Cited

U.S. PATENT DOCUMENTS

| | | |
|---|---|---|
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0358224 A1 | 12/2014 | Tegels et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0135506 A1 | 5/2015 | White |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0327994 A1 | 11/2015 | Morriss et al. |
| 2015/0328001 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1* | 2/2016 | Shahriari ............... A61F 2/2409 623/2.18 |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0279386 A1 | 9/2016 | Dale et al. |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |

FOREIGN PATENT DOCUMENTS

| | | |
|---|---|---|
| DE | 102006052564 B3 | 12/2007 |
| EP | 1171059 A1 | 1/2002 |
| EP | 1369098 A1 | 12/2003 |
| EP | 1259194 B1 | 2/2005 |
| EP | 1255510 B1 | 4/2007 |
| EP | 1827558 A2 | 9/2007 |
| EP | 1239901 B1 | 10/2007 |
| EP | 1472996 B1 | 9/2009 |
| EP | 1935377 B1 | 3/2010 |
| EP | 2238947 A2 | 10/2010 |
| EP | 2308425 A1 | 4/2011 |
| EP | 2398543 A1 | 12/2011 |
| EP | 1281375 B1 | 2/2012 |
| EP | 2496182 A1 | 9/2012 |
| EP | 2285317 B1 | 12/2012 |
| EP | 2566416 A1 | 3/2013 |
| EP | 2319458 B1 | 4/2013 |
| EP | 2124826 B1 | 7/2014 |
| EP | 2750630 A1 | 7/2014 |
| EP | 2777617 A1 | 9/2014 |
| EP | 2745805 B1 | 6/2015 |
| EP | 2749254 B1 | 6/2015 |
| EP | 2898858 A1 | 7/2015 |
| EP | 1734903 B1 | 10/2015 |
| EP | 2967858 A2 | 1/2016 |
| EP | 2926766 B1 | 2/2016 |
| EP | 2985006 A1 | 2/2016 |
| EP | 2168536 B1 | 4/2016 |
| EP | 2815725 B1 | 4/2016 |
| EP | 2237746 B1 | 5/2016 |
| EP | 2815723 B1 | 7/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 1315844 A | 5/1973 |
| GB | 2398245 A | 8/2004 |
| JP | 2002540889 A | 12/2002 |
| JP | 2008541865 A | 11/2008 |
| WO | 0061034 A1 | 10/2000 |
| WO | 03092554 A1 | 11/2003 |
| WO | 2004030569 A2 | 4/2004 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2006127765 A1 | 11/2006 |
| WO | 2007025028 A1 | 3/2007 |
| WO | 2007058857 A2 | 5/2007 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008125153 A1 | 10/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2009134701 A2 | 11/2009 |
| WO | 2010005524 A2 | 1/2010 |
| WO | 2010008549 A1 | 1/2010 |
| WO | 2010022138 A2 | 2/2010 |
| WO | 2010037141 A1 | 4/2010 |
| WO | 2010040009 A1 | 4/2010 |
| WO | 2010057262 A1 | 5/2010 |
| WO | 2011025945 A1 | 3/2011 |
| WO | 2011057087 A1 | 5/2011 |
| WO | 2011111047 A2 | 9/2011 |
| WO | 2011137531 A1 | 11/2011 |

(56) References Cited

FOREIGN PATENT DOCUMENTS

| WO | 2012177942 A2 | 12/2012 |
|---|---|---|
| WO | 2013028387 A2 | 2/2013 |
| WO | 2013059747 A1 | 4/2013 |
| WO | 2013075215 A1 | 5/2013 |
| WO | 2013106585 A1 | 7/2013 |
| WO | 2013120181 A1 | 8/2013 |
| WO | 2013175468 A2 | 11/2013 |
| WO | 2013192305 A2 | 12/2013 |
| WO | 2014018432 A2 | 1/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2015077274 A1 | 5/2015 |
| WO | 2015148241 A1 | 10/2015 |
| WO | 2016016899 A1 | 2/2016 |
| WO | 2016065158 A1 | 4/2016 |
| WO | 2017096157 A1 | 6/2017 |

OTHER PUBLICATIONS

Boudjemline, Younes, et al., "Steps Toward the Percutaneous Replacement of Atrioventricular Valves," JACC, vol. 46, No. 2, Jul. 19, 2005:360-5.

Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

Karimi, Houshang, et al., "Percutaneous Valve Therapies," SIS 2007 Yearbook, Chapter 11, pp. 1-11.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. 2005.

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.

NJ350: Vote for Your Favorite New Jersey Innovations, Jun. 27, 2014, http://www.kilmerhouse.com/2014/06/nj350-vote-for-your-favorite-new-jersey-innovations/.

Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.

Spillner, J. et al., "New Sutureless 'Atrial- Mitral-Valve Prosthesis' For Minimally Invasive Mitral Valve Therapy," Textile Research Journal, 2010, in 7 pages, Applicant believes this may have been available as early as Aug. 9, 2010.

* cited by examiner

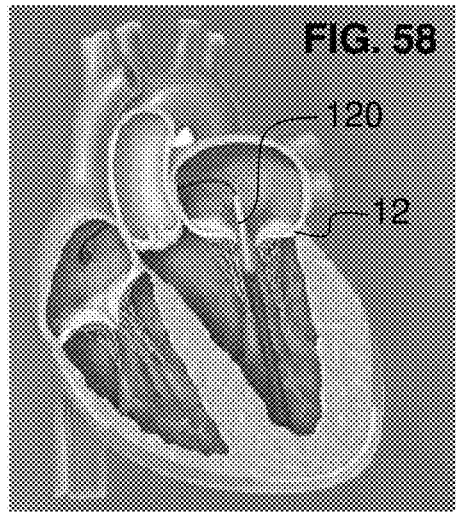
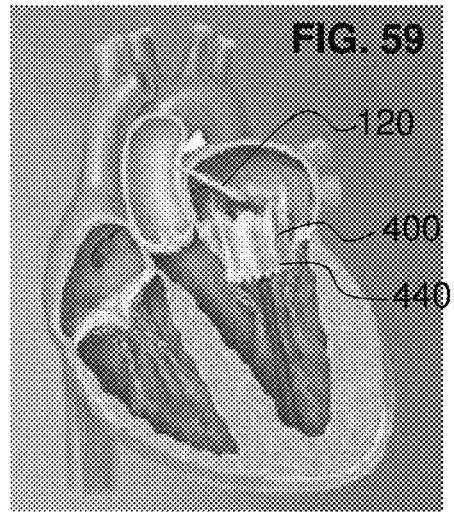
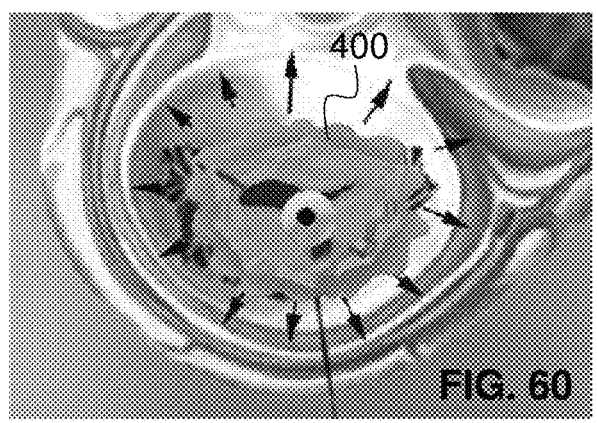
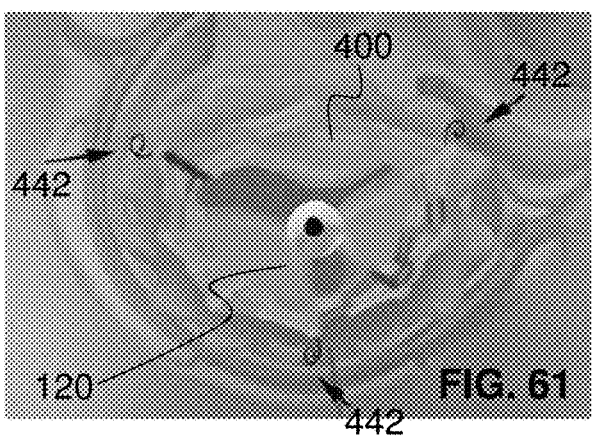
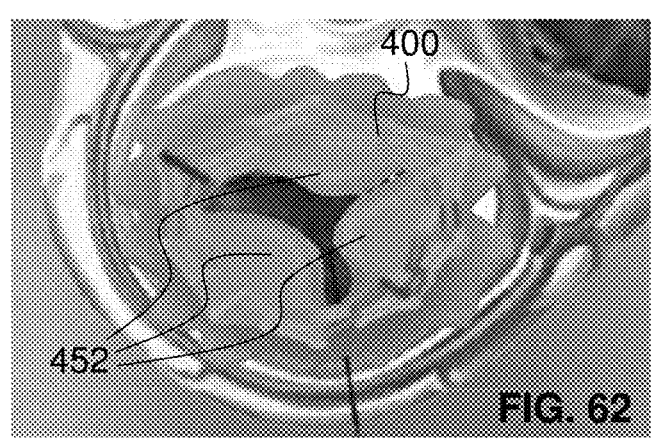

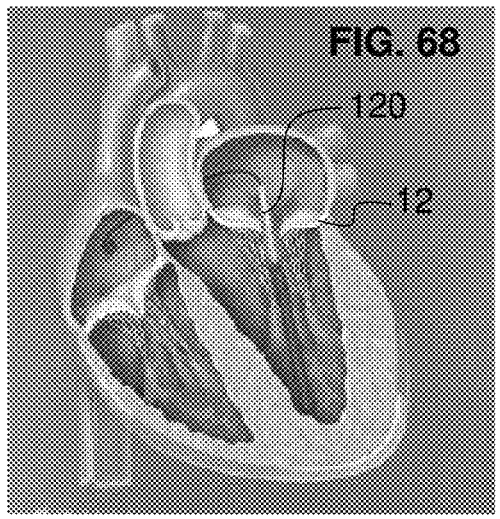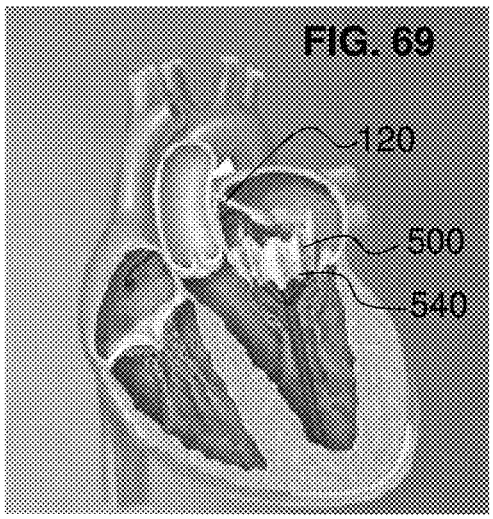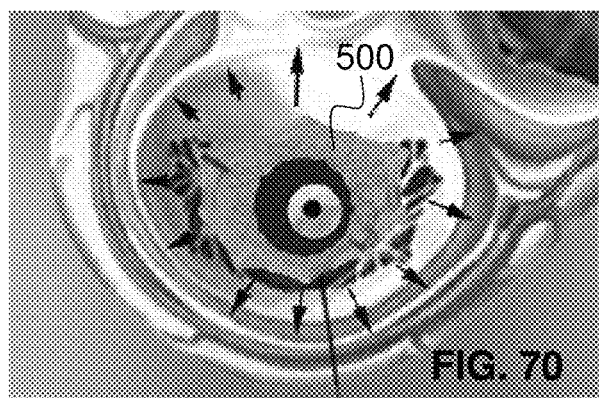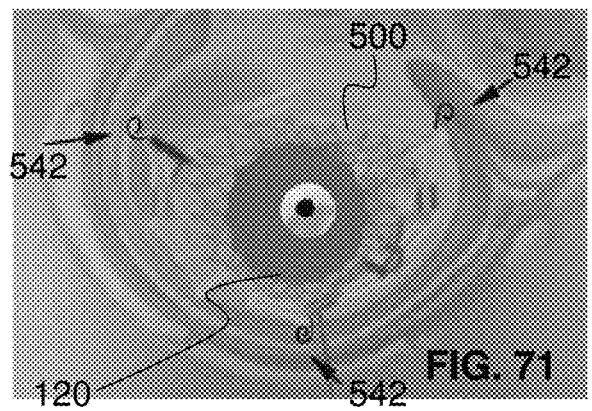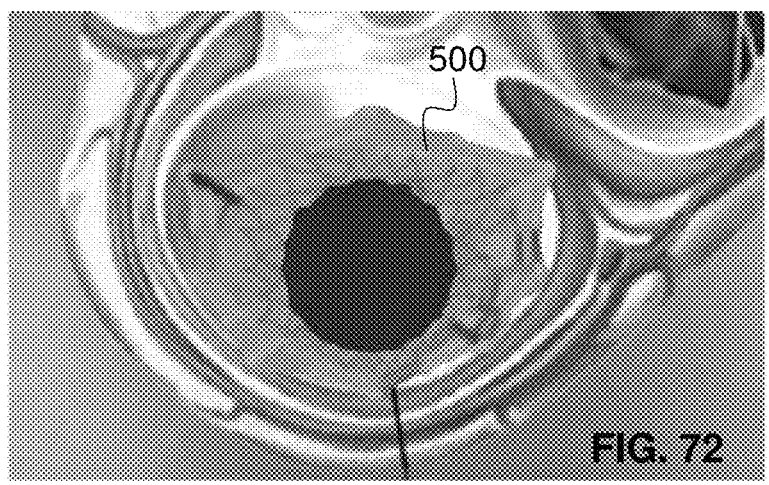

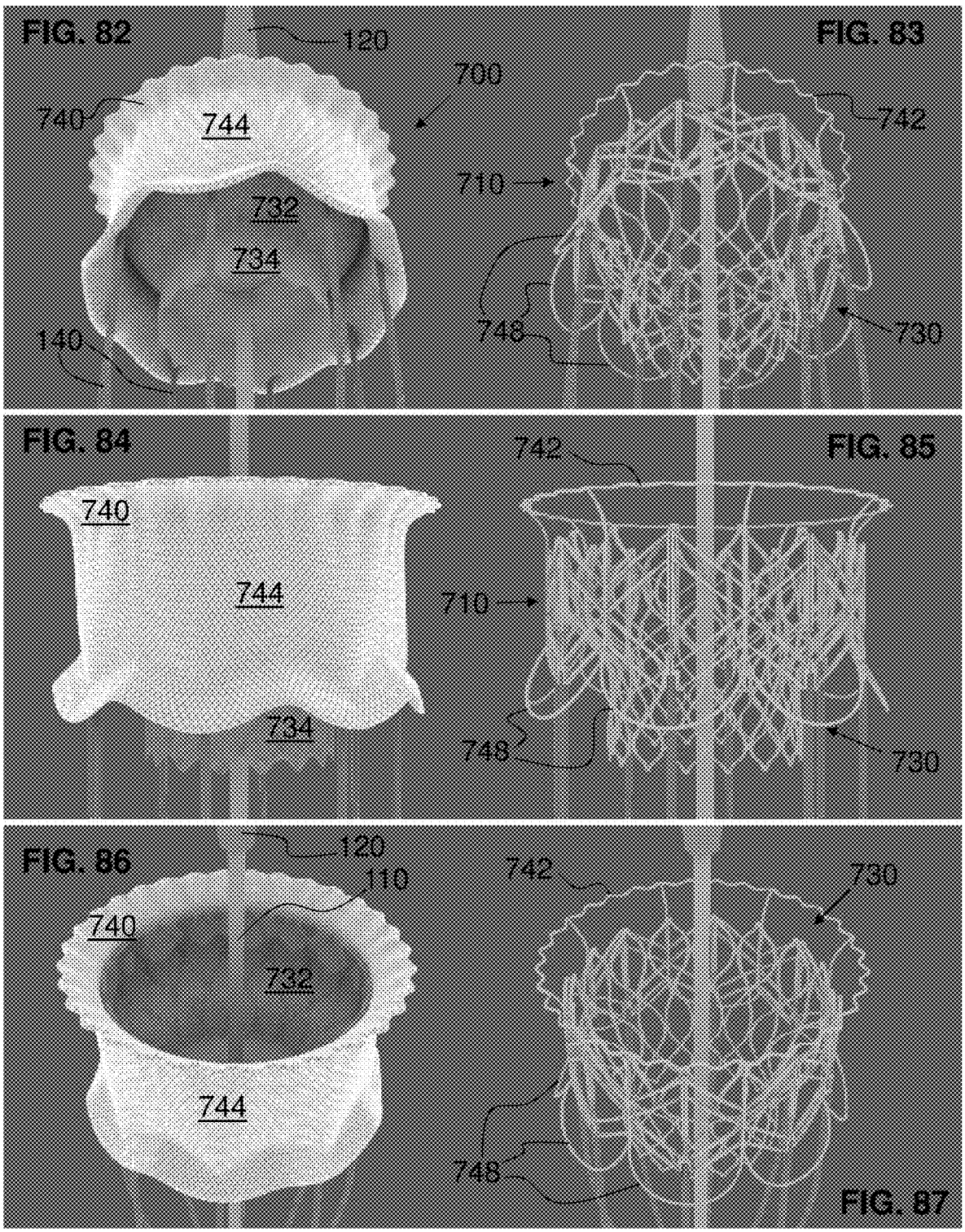

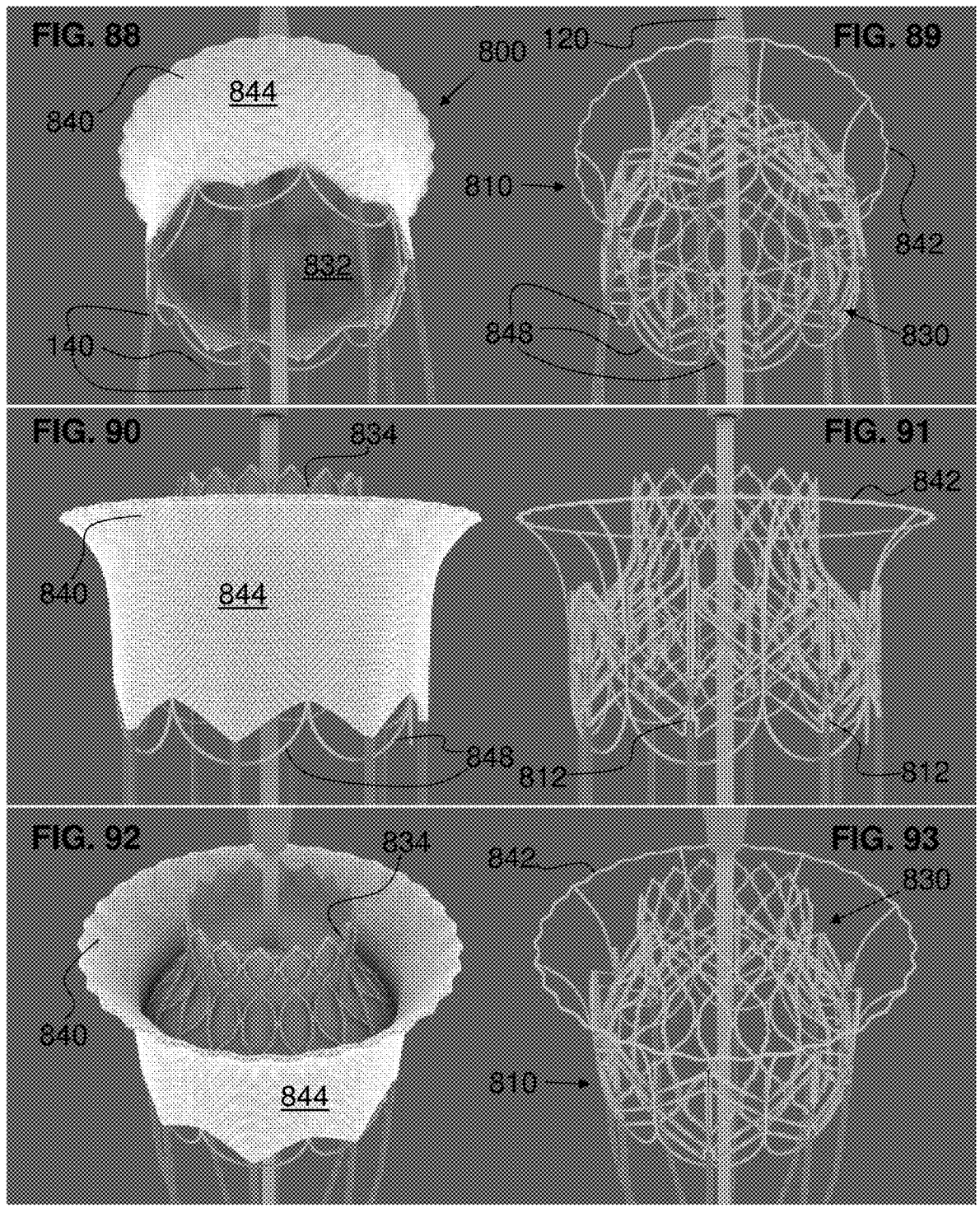

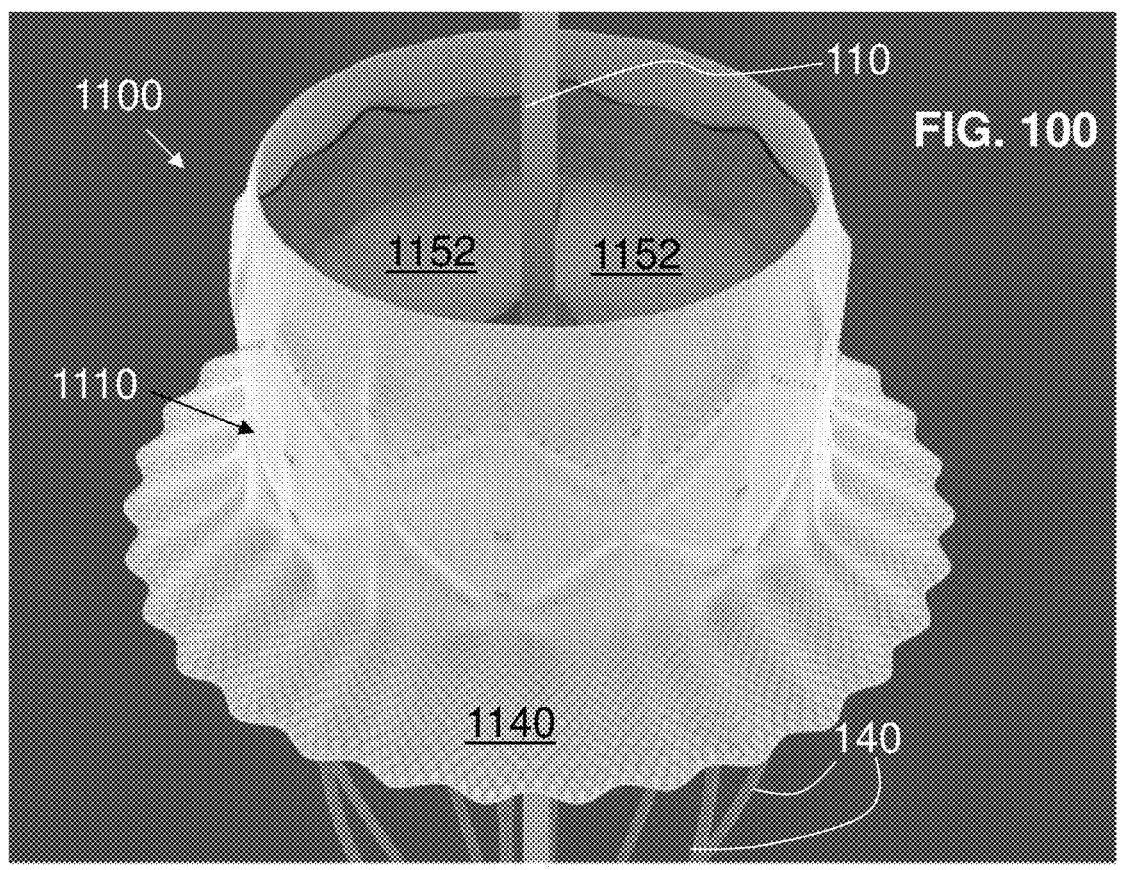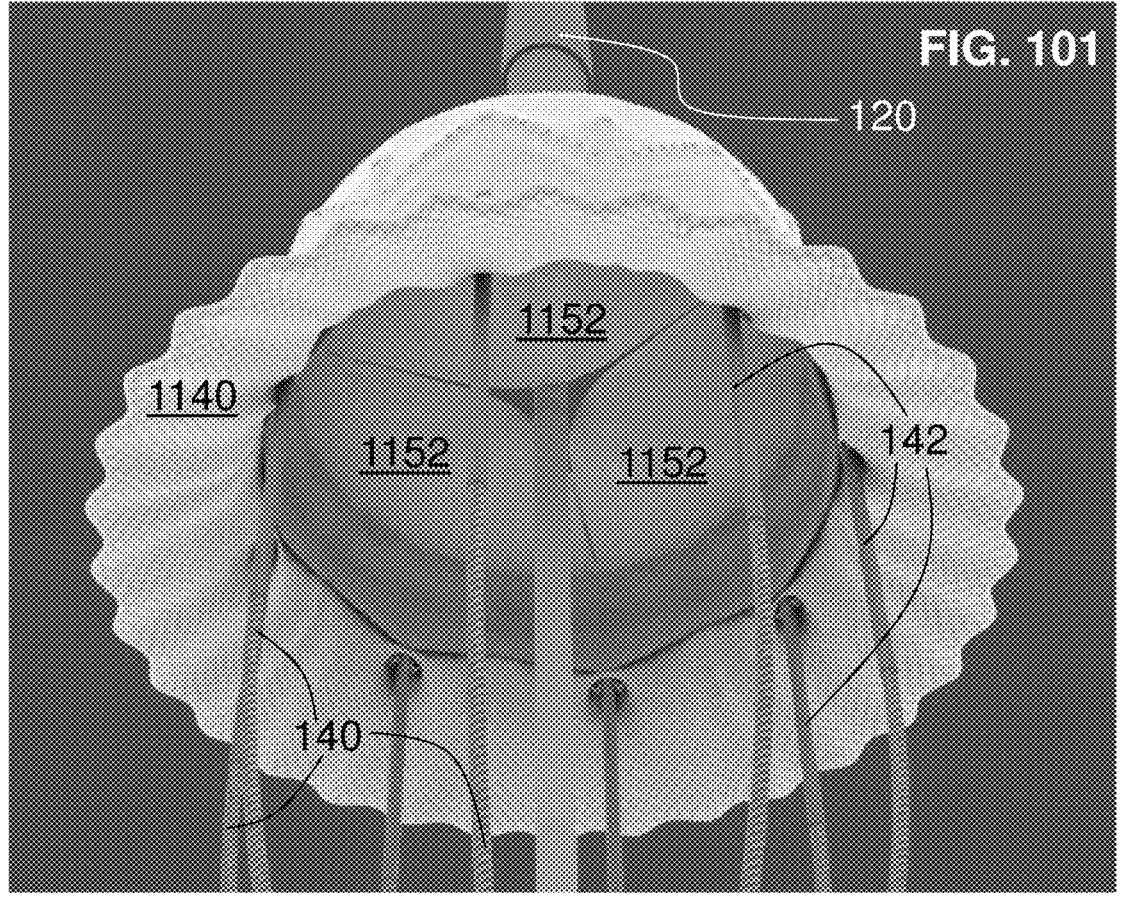

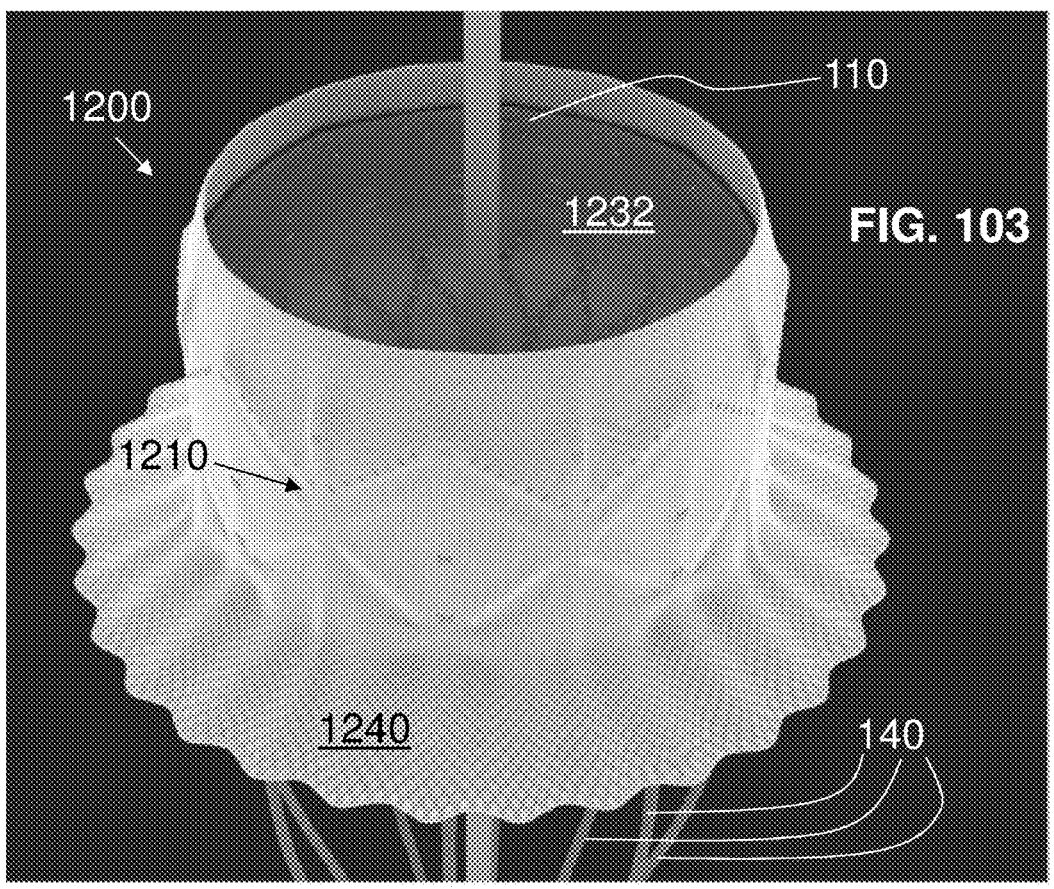
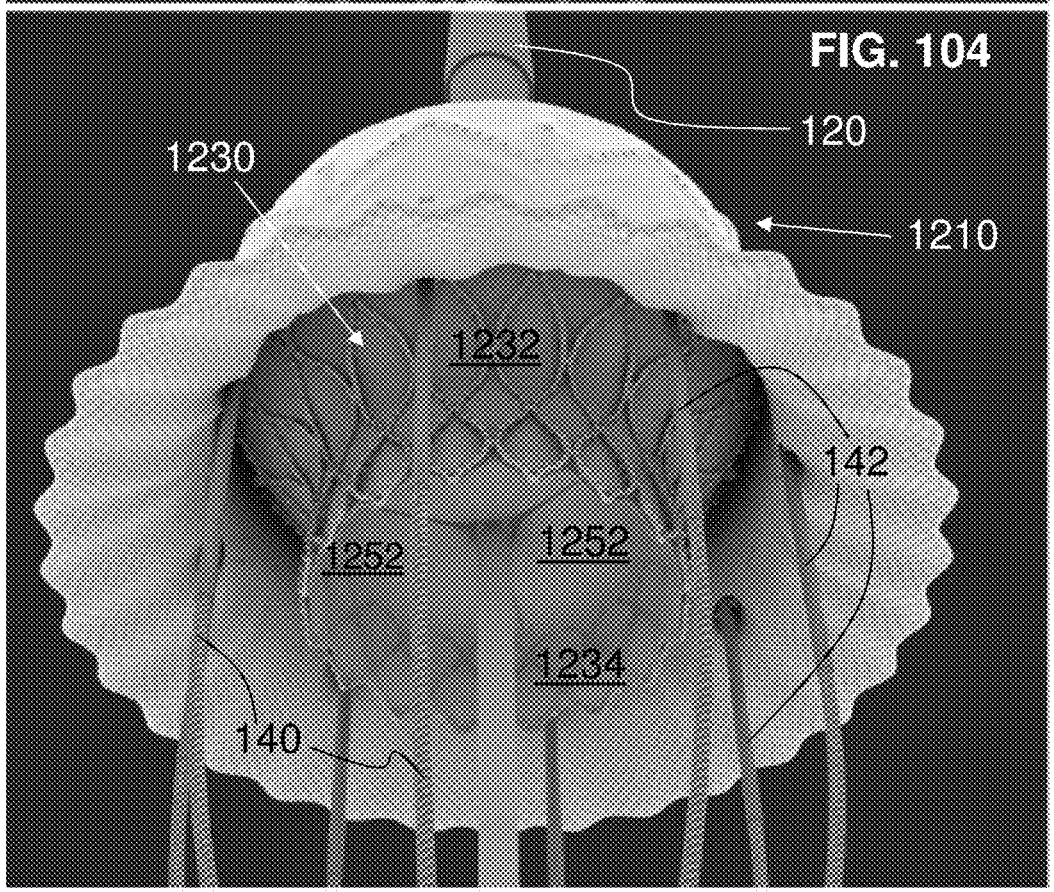

ACTIVELY CONTROLLABLE HEART VALVE IMPLANT AND METHOD OF CONTROLLING SAME

CROSS-REFERENCE TO RELATED APPLICATIONS

This application is a continuation of U.S. application Ser. No. 15/189,786, filed Jun. 22, 2016, which claims the benefit of U.S. Provisional Application No. 62/182,820, filed Jun. 22, 2015 and U.S. Provisional Application No. 62/183,451, filed Jun. 23, 2015, the entire disclosures of which are incorporated by reference in their entireties

FIELD OF THE INVENTION

The present invention lies in the field of heart valve implants (including mitral, aortic, pulmonary, and tricuspid), and methods and systems for controlling and implanting heart valves.

BACKGROUND OF THE INVENTION

The human heart can suffer from various valvular diseases, which can result in significant malfunctioning of the heart and ultimately require replacement of the native heart valve with an artificial valve. There are a number of known artificial valves and a number of known methods of implanting these artificial valves in humans.

One method of implanting an artificial heart valve in a human patient is via open-chest surgery, during which the patient's heart is stopped and the patient is placed on cardiopulmonary bypass (using a so-called "heart-lung machine"). In one common surgical procedure, the diseased native valve leaflets are excised and a prosthetic valve is sutured to the surrounding tissue at the native valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure.

Because of the drawbacks associated with conventional open-chest surgery, percutaneous and minimally-invasive surgical approaches are in some cases preferred. In one such technique, a prosthetic valve is configured to be implanted in a much less invasive procedure by way of catheterization. For instance, U.S. Pat. Nos. 7,393,360, 7,510,575, and 7,993,394 describe collapsible transcatheter prosthetic heart valves that can be percutaneously introduced in a compressed state on a catheter and expanded to a functional size at the desired position by balloon inflation or by utilization of a self-expanding frame or stent.

Various heart valve replacement devices exist in the art and, during the past decade, advancements in valve replacement implants have been achieved. Many of these advancements have occurred with those implants delivered percutaneously in a compressed state on a catheter and, with outer sheath retraction, self-expand to a given extent for implantation. Some implants are made of entirely self-expanding structures. Other implants partially self-expand and then are further expanded by force. Such dual-expansion implants can be made from a single, substantially cylindrical, lattice structure having a pre-defined (e.g., heat-set) initial shape that is smaller than the intended implantation diameter of an anatomic orifice, such as a vessel or heart valve. The lattice can be made of nitinol, for example. A lattice of non-self-expanding material can also be used, for example, of a cobalt chromium material. Within the lattice there can be a set of adjustable expansion devices that place respective forces upon the lattice to elastically and/or plastically deform the lattice to a size that is even greater than the pre-defined shape. One example of the expansion devices is a set of jack screws that are controlled by rotating drive wires (which wires extend from the implant location to the environment outside the patient and terminate, for example, at an electronic delivery control handle). As shown in U.S. Patent Application Publication Nos. 2013/0046373, 2013/0166017, and 2014/0296962, these rotating wires are initially connected to a respective jack screw and rotation of each wire causes a corresponding rotation of the jack screw. With the jack screws being connected to the lattice on each of their opposing ends (for example, through a threaded connection on one end and a freely rotating but longitudinally fixed connection on the other), rotation in one direction expands the circumference of the lattice and rotation in the other direction contracts the lattice. These control wires can be connected to the delivery handle with temporary securement structures that keep the wires rotationally connected to the respective jack screw until implantation and release of the replacement valve is desired. Before being disconnected, the control wires can reversibly expand and contract the lattice as the surgeon desires for optimal placement in the installation location. In other words, such implants can be repositioned before final deployment. When the implant is positioned in a final desired orientation, the drive wires are disconnected from all of the jack screws and are removed from the patient.

One advantage that such implants have over entirely self-expanding lattices is that these implants can be carefully expanded and also can provide feedback to the operator as to the device diameter and forces encountered from surrounding tissue. In contrast, entirely self-expanding implants continuously expand and apply an outwardly directed force where the lattice is implanted. The final diameter of the implant is not finely controllable or adjustable. Expansion of the tissue could lead to paravalvular leakage, movement of the implant, and/or embolism, all of which are undesirable.

Another feature of lattice implants that, upon deployment, first self-expand when removed from the installation catheter and then are forcibly expanded into the delivery site (referred to as self-expanding/forcibly expanding) is the fact that the force imparted against the tissue can be measured (and/or calculated) and either minimized or set to a desired value. While rotating the drive wires, any torque applied to the drive wires can be measured and determined with an implant delivery and deployment system having sensors (e.g., electronic sensors) that measure various parameters, such as current draw for example. Rotation of the drive wires for expanding the implant can be halted when a value of the determined torque is reached.

Delivery of implants in the art for replacement or repair of a heart valve can be achieved over different avenues. One percutaneous way that implant delivery can occur is through the aorta, where the entry site in the patient is located adjacent the femoral artery, referred to as the transfemoral (TF) approach. Another route to implantation of a replacement valve is through a transapical approach. Aortic replacement valves installed in these manners are referred to as Transcatheter Aortic Valve Replacement (TAVR) and Transcatheter Aortic Valve Implantation (TAVI) surgeries, which can be transapical. A third path through the septum of the heart is also possible and one such procedure is referred as a Transseptal (TS) Antegrade Transcatheter Aortic Valve Replacement.

For the treatment of mitral valve disease, Transcatheter Mitral Valve Replacement (TMVR) has been the subject of study, but has not been widely commercialized. Current TMVR techniques have several limitations. First, the size of the valves that are available for TMVR implant may not fit well. In particular, the mitral valve is not substantially circular, it has a D-shape with a long curving interface between the mitral valve's native leaflets. This is in contrast to the aortic valve, which is substantially circular. Also, the TMVR devices do not tend to allow for repositioning of the implant once it has been deployed in place. Next, the final expanded diameter of the known TMVR devices is predetermined, making pre-sizing by a doctor a critical and difficult step. The physician must remotely assess the size of the diseased valve for selecting the correct implant. Migration of existing mitral valve implants is a significant clinical problem, potentially causing leakage and/or compromising necessary vascular supply. In such situations, emergency open surgery can be required, and/or it can lead to an unstable seal and/or migration.

No commercially approved transcatheter mitral valve exists. Some are being studied but there is no replacement mitral valve that can be fully repositioned during deployment and adjusted to better accommodate and seal a natural, diseased mitral valve. Thus, a need exists to overcome the problems with the prior art systems, designs, and processes as discussed above.

SUMMARY OF THE INVENTION

Embodiments of the systems, apparatuses, and methods described herein relate to an actively controllable implant or heart valve implant and methods of controlling same that overcome the hereinafore-mentioned disadvantages of the heretofore-known devices and methods of this general type and that provide such features with the ability to be fully repositioned before final deployment.

Described herein are various systems, apparatuses, and methods for implanting replacement heart valves, which implants can be used in any valve of the heart. In some exemplary embodiments herein, implants for a stent graft, a valve, a mitral valve and associated system, apparatuses, and methods are shown and described.

As compared to other heart valves, in a diseased mitral valve, the tissue is relatively soft. This means that prior art self-expanding mitral implant valves which are oversized relative to the native mitral valve continuously provide an outward expanding force to the native mitral valve tissue. This force further expands the diseased tissue throughout the life of the implant. Such a result is not desirable for many reasons, e.g., leakage, movement, and/or embolization. Provided herein in some exemplary embodiments are heart valve (e.g., mitral valve) replacement implants that do not continuously provide an outwardly directed force after implantation. These implants have a self-expansion aspect but that self-expansion occurs only for a certain extent—before or up to the native annulus of tissue surrounding the mitral valve. After the self-expansion occurs, the adjustable stent lattice portion of the implant is then forcibly expanded into the native annulus only to an extent to seat the implant within the annulus with no leakage occurring around the implant. This means that, when a correct and sufficient implanted status occurs, there will be no additional outwardly directed force imparted on the native annulus by the implant to cause further outwards expansion of that tissue over the life of the implant. This advantage over the prior art permits greater longevity. Also provided in some of the exemplary embodiments are optional structures that ensure a fluid-tight seal against each of the two sides of the valve being replaced. One exemplary implant-securing structure is a self-expanding, implant skirt attached to the adjustable stent lattice, having a material that is fluid-tight or resistant (or after being installed becomes fluid-tight), and, when released from the delivery catheter, springing open to occlude the side of the valve on which it resides. It essentially is in the form of an umbrella that contacts the side of the implant site on its entire circumference. Another independent exemplary implant-securing structure is a set of self-expanding, wall-retaining petals. These petals can be compressed within delivery wires while the implant is installed in the delivery catheter, can continue to be held radially inwards by the delivery wires, while the implant is being maneuvered and installed in an implant site, and spring open radially away from the central longitudinal axis of the implant when the delivery wires are released from the implant upon final deployment. In this way, the implant is adjustable and repositionable repeatedly in both the expansion and contraction directions up until final deployment. With both implant-securing structures on opposing sides of the implant, the petals, the implant skirt, and the adjustable stent lattice form an annulus having a concave U-shape that can entirely capture and hold therein the native valve annulus in a fluid-tight and leak-tight manner.

A further advantage of some of the embodiments of herein-described mitral valve implants relates to the size of the valve portion when the implant is secured in the native annulus. The native annulus of mitral valves are substantially D-shaped. One characteristic of a diseased mitral valve is that the annulus stretches outwardly, leaving the leaflets of the mitral valve unable to coapt and, thereby, impairing the functionality of the valve. In what is referred to as Mitral Valve Prolapse, one or both of the valve flaps are enlarged and do not close in an even manner. With improper closure, blood could flow backwards into the left atrium, referred to as Mitral Valve Regurgitation. With a stretching of the mitral valve annulus, even if a prior art implant is able to be secured therein, the size of that implant's valve opening may be too large for the patient. Some of the embodiments of the mitral valve implant herein provide a valve opening sized for optimal flow irrespective of the size of the diseased mitral valve annulus. These embodiments provide a fixed-sized valve opening contained within a variable outer annular skirt, the combined structures of the variably sized outer skirt and the fixed-sized valve being referred to herein as a trampoline valve. These exemplary implants, therefore, provide an ideal amount of flow through the valve of the implant in spite of the enlarged native mitral valve annulus. This means that, regardless of the final D-shaped diameter of the implanted stent lattice, the trampoline valve will have its own fixed maximum circular diameter, which improves valve function and durability. This feature allows a standard-sized valve to cover a large patient population with mitral valves of various sizes. The skirt can optionally have a downstream flair that creates a back seal when high pressure of ventricle contraction is imparted.

With the foregoing and other objects in view, there is provided, a mitral valve implant comprising a force-expanding mitral valve lattice having an interior orifice and a self-expanding valve trampoline attached at the interior orifice of the force-expanding mitral valve lattice.

With the objects in view, there is also provided a mitral heart valve implant system comprising a valve delivery system, a self-expanding and forcibly expanding mitral valve frame, a self-expanding implant skirt, wall-retaining wires, and a self-expanding valve trampoline lattice. The valve delivery system comprises a controller, a guidewire lumen connected to the controller and having a distal nosecone, a hollow external sheath surrounding the guidewire lumen, having a proximal end connected to the controller, and configured to retract proximally from an extended, valve-installed position, a given number of implant drive wires each having a distal drive wire connector, and hollow connector lumens equal in number to the given number and each respectively threaded on one of the drive wires and having a distal hollow connector sleeve. The self-expanding and forcibly expanding mitral valve frame defines a central axis and comprises proximal and distal jack screw strut pairs equal in number to the given number and disposed parallel to the central axis, intermediate struts equal in number to the given number and disposed parallel to the central axis, each intermediate strut disposed between two adjacent ones of the jack screw strut pairs, arms respectively connecting adjacent ones of the jack screw strut pairs and the intermediate struts, and a plurality of jack screws. The jack screws are each rotatably connected to one jack screw strut pair, form, together with the jack screw strut pairs, the intermediate struts, and the arms, an adjustable stent lattice having a ventricle side and an atrial side, are configured to reversibly forcibly expand and contract the adjustable stent lattice between a compressed state and an enlarged state for implantation of the mitral valve frame into a native mitral valve, and each have a driving connector shaped to removably mate and connect to the distal drive wire connector of one of the drive wires and be held connected thereto when the hollow connector sleeve is disposed about the mated driving connector and distal drive wire connector such that rotation of the drive wires correspondingly rotates the jack screws to forcibly expand or contract the adjustable stent lattice. The self-expanding implant skirt is attached to the ventricle side of the adjustable stent lattice. The implant skirt is configured to compress and be stored inside the external sheath and, when released from the external sheath at a native mitral valve, to self-expand and sealably position on tissue at a ventricular side of the native mitral valve. The wall-retaining wires are attached to the atrium side of the adjustable stent lattice and are configured to compress and be stored inside the external sheath and, when released from the external sheath at a native mitral valve, to self-expand on tissue at an atrial side of the native mitral valve. The self-expanding valve trampoline lattice is disposed inside and is connected to the adjustable stent lattice and comprises an expandable outer trampoline portion having a circumferential exterior connected to the interior of the adjustable stent lattice and a circumferential interior and an inner circumferential valve portion connected to the circumferential interior and extending inwardly from the circumferential interior to define an interior cylindrical portion and having a circular valve with internal valve leaflets disposed at the interior cylindrical portion.

With the objects in view, there is also provided a mitral heart valve implant system comprises a mitral valve lattice having a pre-set D-shaped cross-sectional configuration, defining an internal orifice, and comprising a plurality of jack screws configured to forcibly expand and contract the mitral valve lattice reversibly between a compressed configuration and an enlarged configuration, an outwardly flaring, self-expanding implant skirt attached to an exterior of the mitral valve lattice, the implant skirt shaped to be positioned on a ventricular side of a native mitral valve to secure the mitral valve lattice in the annulus of the native mitral valve, radially outwardly biased wall-retaining wires attached to the mitral valve lattice and shaped to be positioned on an atrial side of the native mitral valve to secure the mitral valve lattice in the annulus of the native mitral valve, a self-expanding valve trampoline lattice containing interior valve leaflets, the valve trampoline lattice disposed within the internal orifice of the mitral valve lattice and having a D-shape portion attached to the mitral valve lattice and a substantially cylindrical interior portion, wherein the valve leaflets are attached to the substantially cylindrical interior portion, and a delivery system comprising a plurality of implant drive wires temporarily connectable to the jack screws such that, when connected, rotation of the drive wires in one direction forcibly expands the mitral valve lattice towards the enlarged configuration and rotation of the drive wires in a direction opposite the one direction forcibly contracts the mitral valve lattice towards the compressed configuration.

With the objects in view, there is also provided a method for implanting a mitral heart valve including the steps of contracting a self-expanding and forcibly-expanding mitral valve of a shape-memory material set to a given shape to a reduced implantation size with a delivery system having drive wires, the mitral valve having an adjustable assembly with adjustable elements operatively connected to the drive wires such that, when the adjustable elements are adjusted by the drive wires, a configuration change in at least a portion of the mitral valve occurs, inserting the contracted mitral valve into a native mitral valve annulus in which the mitral valve is to be implanted, rotating the drive wires with the delivery system to forcibly expand the mitral valve into the native annulus, while rotating the drive wires, determining with the delivery system a torque applied to the drive wires, and stopping rotation of the drive wires based upon a value of the determined torque.

In accordance with another feature, the force-expanding mitral valve lattice is self-expandable to a first configuration and is force expandable from the first configuration to a second configuration.

In accordance with a further feature, the first configuration is one of circular and D-shaped.

In accordance with an added feature, the second configuration corresponds in shape to the one of circular and D-shaped first configuration.

In accordance with an additional feature, the mitral valve lattice comprises a plurality of jack screws configured to adjust expansion and contraction of a configuration of the mitral valve lattice.

In accordance with yet another feature, the mitral valve lattice is made of a shape memory material set shape to a given shape.

In accordance with yet a further feature, the valve trampoline has a cylindrical central region comprising valve leaflets.

In accordance with yet an added feature, the valve trampoline comprises a D-shaped portion.

In accordance with yet an additional feature, the valve leaflets have an inflow side and the D-shaped portion is located on an inflow side of the valve leaflets.

In accordance with again another feature, the mitral valve lattice has an exterior and there is provided an outwardly flaring implant skirt attached to the exterior of the mitral valve lattice and shaped to be positioned on a side of a native mitral valve.

In accordance with again a further feature, there are provided wall-retaining wires attached to the mitral valve lattice and shaped to be positioned on a side of the native mitral valve.

In accordance with again an added feature, the wall-retaining wires are in the shape of petals and have a pre-set, radially outward, memory shape to impart a force on the side of the native mitral valve when the mitral valve lattice is expanded within an annulus of the native mitral valve.

In accordance with again an additional feature, the implant skirt is a left ventricle implant skirt shaped to be positioned on a ventricular side of the native mitral valve when the mitral valve lattice is expanded within the annulus of the native mitral valve and the wall-retaining wires are left-atrium wall-retaining wires shaped to be positioned on an atrial side of the native mitral valve when the mitral valve lattice is expanded within the annulus of the native mitral valve.

In accordance with still another feature, the implant skirt is a left atrium implant skirt shaped to be positioned on an atrial side of the native mitral valve when the mitral valve lattice is expanded within the annulus of the native mitral valve and the wall-retaining wires are left-ventricle wall-retaining wires shaped to be positioned on a ventricular side of the native mitral valve when the mitral valve lattice is expanded within the annulus of the native mitral valve.

In accordance with still a further feature, the mitral valve lattice has an inlet end and an outlet end and the valve trampoline is attached to the inlet end of the interior orifice.

In accordance with still an added feature, the mitral valve lattice has an inlet end and an outlet end and the valve trampoline is attached to the outlet end of the interior orifice.

In accordance with a concomitant feature, the adjustable stent lattice has a pre-set D-shaped cross-section and the exterior of the expandable outer trampoline portion is pre-set to a circumferential D-shape.

Although the systems, apparatuses, and methods are illustrated and described herein as embodied in an actively controllable heart valve implant and methods of controlling same, it is, nevertheless, not intended to be limited to the details shown because various modifications and structural changes may be made therein without departing from the spirit of the invention and within the scope and range of equivalents of the claims. Additionally, well-known elements of exemplary embodiments will not be described in detail or will be omitted so as not to obscure the relevant details of the systems, apparatuses, and methods.

Additional advantages and other features characteristic of the systems, apparatuses, and methods will be set forth in the detailed description that follows and may be apparent from the detailed description or may be learned by practice of exemplary embodiments. Still other advantages of the systems, apparatuses, and methods may be realized by any of the instrumentalities, methods, or combinations particularly pointed out in the claims.

Other features that are considered as characteristic for the systems, apparatuses, and methods are set forth in the appended claims. As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one of ordinary skill in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the systems, apparatuses, and methods of the invention that are regarded as novel, it is believed that the systems, apparatuses, and methods will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the systems, apparatuses, and methods. Advantages of embodiments of the systems, apparatuses, and methods will be apparent from the following detailed description of the exemplary embodiments thereof, which description should be considered in conjunction with the accompanying drawings in which:

FIG. 58 is a fragmentary, vertically cross-sectional and perspective view of the delivery system of FIG. 44 inserted through the apex of the heart and through the mitral valve annulus into the left atrium;

FIG. 59 is a fragmentary, vertically cross-sectional and perspective view of the heart of FIG. 58 with the delivery system deploying the replacement mitral valve implant of FIG. 57 with the implant partially expanded in the mitral valve annulus;

FIG. 60 is a fragmentary, horizontally cross-sectional and perspective view of the heart of FIG. 59;

FIG. 61 is a fragmentary, horizontally cross-sectional and perspective view of the heart of FIG. 60 with the delivery system having deployed hooks of the implant into the mitral valve annulus;

FIG. 62 is a fragmentary, horizontally cross-sectional and perspective view of the heart of FIG. 61 with the delivery system removed from the heart and the implant secured in the mitral valve annulus;

FIG. 68 is a fragmentary, vertically cross-sectional and perspective view of the delivery system of FIG. 44 inserted through the apex of the heart and through the mitral valve annulus into the left atrium;

FIG. 69 is a fragmentary, vertically cross-sectional and perspective view of the heart of FIG. 68 with the delivery system deploying the replacement mitral valve implant of FIG. 67 with the implant partially expanded in the mitral valve annulus;

FIG. 70 is a fragmentary, horizontally cross-sectional and perspective view of the heart of FIG. 69 with the leaflets removed from the implant;

FIG. 71 is a fragmentary, horizontally cross-sectional and perspective view of the heart of FIG. 70 with the delivery system having deployed hooks of the implant into the mitral valve annulus;

FIG. 72 is a fragmentary, horizontally cross-sectional and perspective view of the heart of FIG. 71 with the delivery system removed from the heart and the implant secured in the mitral valve annulus;

FIG. 82 is an installation-side perspective view of another exemplary embodiment of an actively controllable, trampoline-side installed, circular valve replacement implant with an implant skirt, covered opposing-side wall-retaining petals, and an internal valve trampoline;

FIG. 83 is an installation-side perspective view of an implant skirt frame, wall-retaining petals, a valve trampoline lattice, and an adjustable stent lattice of the circular valve replacement implant of FIG. 82;

FIG. 84 is a substantially side elevational view of the circular valve replacement implant of FIG. 82;

FIG. 85 is a substantially side elevational view of the implant skirt frame, the wall-retaining petals, the valve trampoline lattice, and the adjustable stent lattice of the circular valve replacement implant of FIG. 82;

FIG. 86 is a nosecone-side perspective view of the circular valve replacement implant of FIG. 82;

FIG. 87 is a nosecone-side perspective view of the implant skirt frame, the wall-retaining petals, the valve trampoline lattice, and the adjustable stent lattice of the circular valve replacement implant of FIG. 82;

FIG. 88 is an installation-side perspective view of another exemplary embodiment of an actively controllable, petal-side installed, circular valve replacement implant with an implant skirt, opposing-side wall-retaining petals, and an internal valve trampoline facing the implant skirt;

FIG. 89 is an installation-side perspective view of an implant skirt frame, wall-retaining petals, a valve trampoline lattice, and an adjustable stent lattice of the circular valve replacement implant of FIG. 88;

FIG. 90 is a substantially side elevational view of the circular valve replacement implant of FIG. 88;

FIG. 91 is a substantially side elevational view of the implant skirt frame, the wall-retaining petals, the valve trampoline lattice, and the adjustable stent lattice of the circular valve replacement implant of FIG. 88;

FIG. 92 is a nosecone-side perspective view of the circular valve replacement implant of FIG. 88;

FIG. 93 is a nosecone-side perspective view of the implant skirt frame, the wall-retaining petals, the valve trampoline lattice, and the adjustable stent lattice of the circular valve replacement implant of FIG. 88;

FIG. 100 is a nosecone-side perspective view of another exemplary embodiment of an actively controllable, circular valve replacement implant with an installation-side implant skirt;

FIG. 101 is an installation-side perspective view of the circular valve replacement implant of FIG. 100;

FIG. 103 is a nosecone-side perspective view of another exemplary embodiment of an actively controllable, circular valve replacement implant with an installation-side implant skirt and a trampoline valve; and FIG. 104 is an installation-side perspective view of the circular valve replacement implant of FIG. 103.

DETAILED DESCRIPTION OF THE INVENTION

Figure 1:
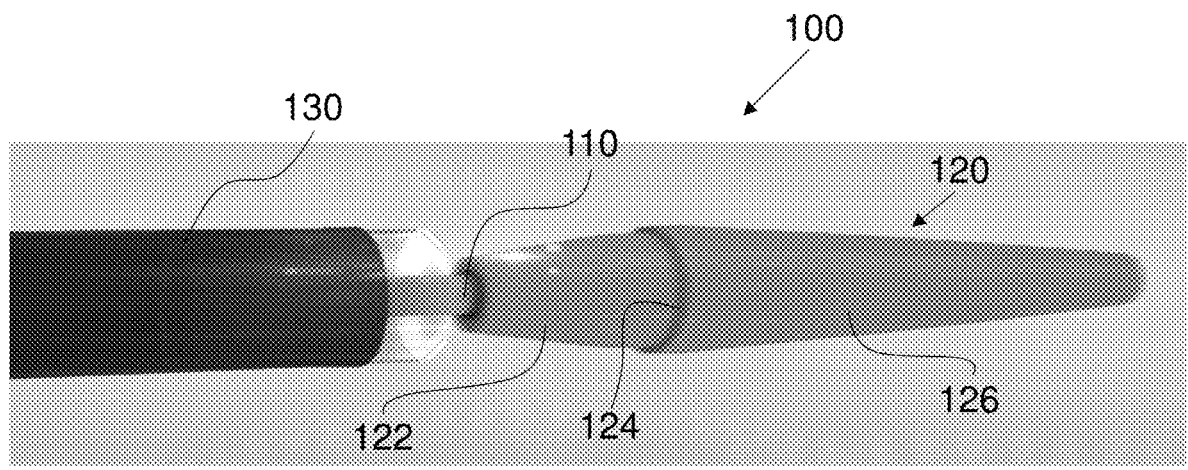
FIG. 1 is a fragmentary, side perspective view of an exemplary embodiment of a distal end of a delivery and deployment system for an actively controllable heart valve implant.

As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are optional and not to be interpreted as limiting, but merely as a basis for the claims and as a representative basis for teaching one skilled in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the features of the systems, apparatuses, and methods that are regarded as novel, it is believed that the systems, apparatuses, and methods will be better understood from a consideration of the following description in conjunction with the drawing figures, in which like reference numerals are carried forward.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Alternate embodiments may be devised without departing from the spirit or the scope of the invention. Additionally, well-known elements of exemplary embodiments of the systems, apparatuses, and methods will not be described in detail or will be omitted so as not to obscure the relevant details of the systems, apparatuses, and methods.

Before the systems, apparatuses, and methods are disclosed and described, it is to be understood that the terminology used herein is for the purpose of describing particular embodiments only and is not intended to be limiting. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including" and/or "having," as used herein, are defined as comprising (i.e., open language). The terms "a" or "an", as used herein, are defined as one or more than one. The term "plurality," as used herein, is defined as two or more than two. The term "another," as used herein, is defined as at least a second or more. The description may use the terms "embodiment" or "embodiments," which may each refer to one or more of the same or different embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact (e.g., directly coupled). However, "coupled" may also mean that two or more elements are not in direct contact with each other, but yet still cooperate or interact with each other (e.g., indirectly coupled).

For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C).

Relational terms such as first and second, top and bottom, and the like may be used solely to distinguish one entity or action from another entity or action without necessarily requiring or implying any actual such relationship or order between such entities or actions. The description may use perspective-based descriptions such as up/down, back/front, top/bottom, and proximal/distal. Such descriptions are merely used to facilitate the discussion and are not intended to restrict the application of disclosed embodiments. Various operations may be described as multiple discrete operations in turn, in a manner that may be helpful in understanding embodiments; however, the order of description should not be construed to imply that these operations are order dependent.

Herein the relational terms "proximal" and "distal" are used. Meanings for these terms are to be determined in the context in which they are used. In various embodiments, where proximal and distal are used with regard to the delivery system and the implant to be deployed, the term "proximal" is in the direction towards the delivery handle and the user and away from the implant and term "distal" is in the direction away from the delivery handle and the user and towards the implant.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

It will be appreciated that embodiments of the systems, apparatuses, and methods described herein may be comprised of one or more conventional processors and unique stored program instructions that control the one or more processors to implement, in conjunction with certain non-processor circuits and other elements, some, most, or all of the functions of the devices and methods described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs) or field-programmable gate arrays (FPGA), in which each function or some combinations of certain of the functions are implemented as custom logic. Of course, a combination of these approaches could also be used. Thus, methods and means for these functions have been described herein.

The terms "program," "software," "software application," and the like as used herein, are defined as a sequence of instructions designed for execution on a computer system or programmable device. A "program," "software," "application," "computer program," or "software application" may include a subroutine, a function, a procedure, an object method, an object implementation, an executable application, an applet, a servlet, a source code, an object code, any computer language logic, a shared library/dynamic load library and/or other sequence of instructions designed for execution on a computer system.

Herein various embodiments of the systems, apparatuses, and methods are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments of the present invention. Referring now to the figures of the drawings in detail and first, particularly to FIGS. 1 to 13, there is shown a first exemplary embodiment of an actively controllable delivery and deployment system 100, for example, for an actively controllable mitral heart valve replacement implant 200. The delivery system 100 includes an inner elongate member that comprises a guidewire lumen 110, a nosecone 120 disposed at the distal end of the guidewire lumen 110, a hollow exterior sheath 130 surrounding the guidewire lumen 110 and shaped to smoothly connect to the proximal end of the nosecone 120, and a non-illustrated delivery and deployment handle connected to the guidewire lumen 110, to the exterior sheath 130, and to implant controls that are described in further detail below. The sheath-nosecone connection is established by forming the proximal end of the nosecone 120 with a taper 122 that ends with an abutting wall 124 at the proximal most end of the distal nosecone taper 126. The distal taper 126 has an outer diameter at the wall 124 that is substantially equal to the outer diameter of the distal end of the sheath 130 and the wall 124 has a height that is substantially equal to the thickness of the material of the hollow sheath 130.

Figure 2:
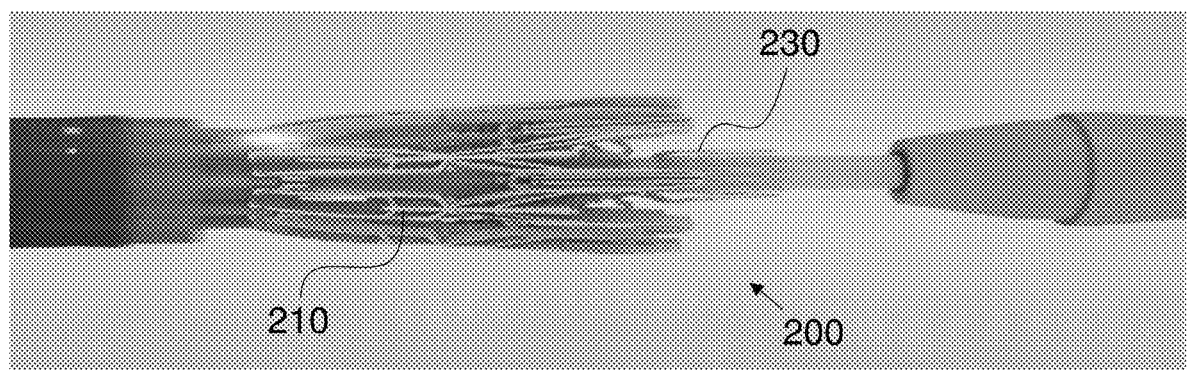
FIG. 2 is a fragmentary, side perspective view of the distal end of the delivery system of FIG. 1 with an exemplary embodiment of an actively controllable mitral valve replacement implant, with an implant skirt and a valve trampoline removed for clarity, in a pre-installation orientation with an outer catheter covering implant drive wires, with the drive wires connected to jack screws of a self-expanding and forcibly-expanding valve lattice, with a self-expanding valve trampoline lattice containing non-illustrated valve leaflets within an orifice of the valve lattice and attached to the valve lattice.

The actively controllable mitral heart valve replacement implant 200 is, in FIG. 1, compressed within the sheath 130 and surrounding the guidewire lumen 110, as can be seen in FIG. 2, in which the sheath 130 has been retracted proximally to such an extent that the implant 200 can be seen in its entire longitudinal extent. Even though the implant 200 should be expanded further than the configuration shown in FIG. 2 when it is fully exposed from the sheath 130, the implant 200 is depicted in FIG. 2 in only a slightly expanded orientation as compared to the completely encased and compressed orientation of the non-visible implant 200 in FIG. 1.

Figure 5:
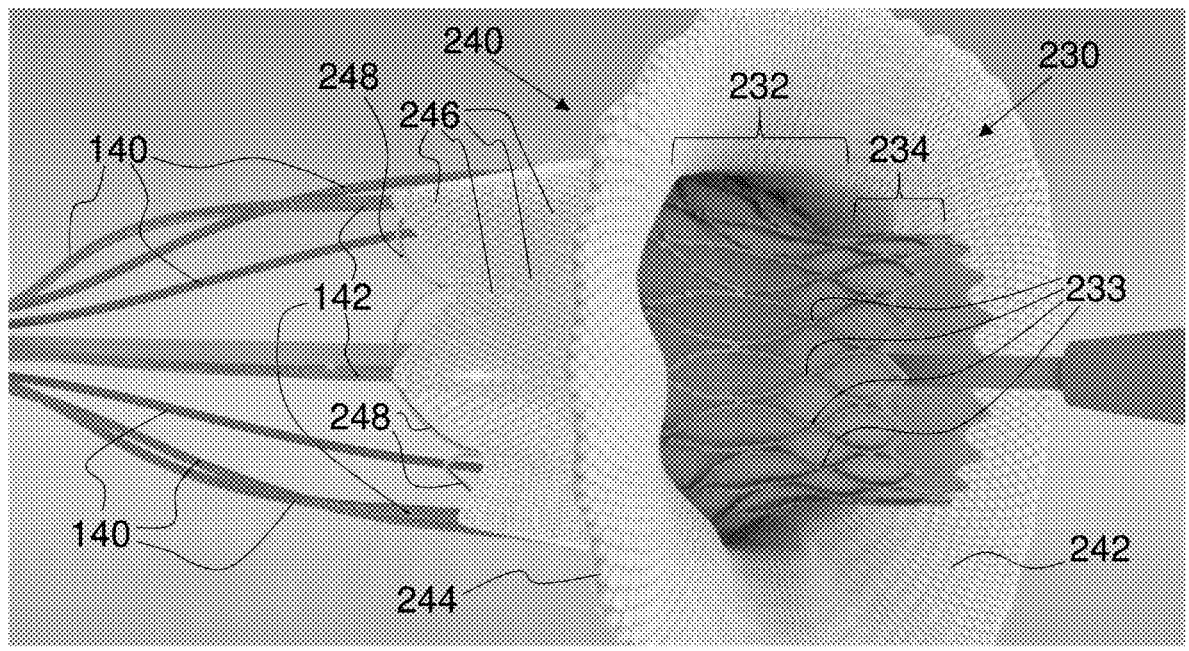
FIG. 5 is a fragmentary, perspective view of the distal end of the delivery system of FIG. 1 with the valve implant of FIG. 4 in a pre-installation orientation with the valve implant in a forcibly expanded, enlarged state.

The implant 200 has an external, adjustable stent lattice 210. The stent lattice 210 can be of a shape memory material (such as nitinol, for example). The adjustable stent lattice 210 is set to a pre-determined shape that, in this exemplary mitral valve embodiment, is D-shaped as shown in FIG. 5 and, particularly, in FIGS. 9 to 12. (In an alternative exemplary embodiment where the implant site is circular, the adjustable stent lattice would be pre-set to a circular shape.) Connected to the interior of the adjustable stent lattice 210 is a self-expanding valve trampoline lattice 230. The trampoline lattice 230 can be integral with the adjustable stent lattice 210 or fixedly connected thereto, for example, by crimping, banding, welding. A set of hollow disconnect lumens 140 surround lattice drive wires 150 and both are operatively connected to a non-illustrated delivery and deployment handle (also referred to as a controller because it need not be shaped as a handle). The exemplary embodiment of the disconnect lumens 140 are tubes that extend from the handle to the implant 200 and each surround a drive wire 150. Lattice disconnect tubes 142 are respectively disposed at the end of each hollow disconnect lumens 140. The lattice disconnect tubes 142 are rotationally fixed to the disconnect lumens 140 such that, when the disconnect lumen 140 rotates, the respective lattice disconnect tube 142 rotates correspondingly. The lattice disconnect tubes 142 surround the distal end of the drive wires 150, at which distal end are drive wire connectors 152. The drive wire connectors 152 are each shaped to connect to respective proximal ends of jack screws 220 that are rotatably connected to the adjustable stent lattice 210 as described in further detail below.

Figure 4:
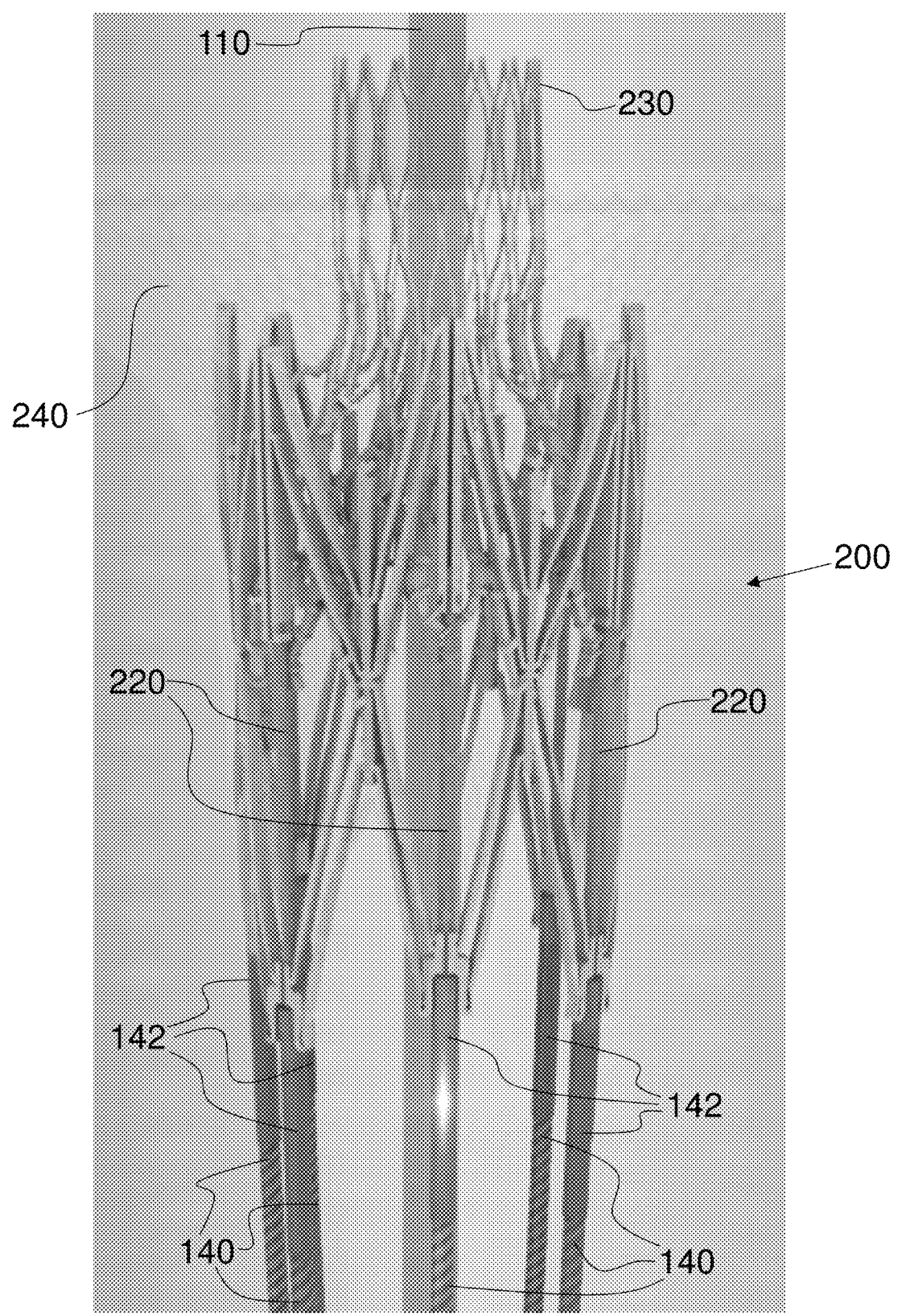
FIG. 4 is an enlarged, fragmentary, side perspective view of the distal end of the delivery system of FIG. 1 with the mitral valve replacement implant of FIG. 3 in a pre-installation orientation with the mitral valve implant in a self-expanded, enlarged state, with the implant skirt and the valve trampoline transparent.

FIG. 2 depicts the implant 200 without an implant skirt and a valve trampoline (which are removed for clarity but are shown in FIG. 4). The implant 200 is in a pre-installation orientation before the drive wires 150 have caused the jack screws 220 to expand the adjustable stent lattice 210. The lattice disconnect tubes 142 at each distal end of the disconnect lumens 140 are partially visible from under the outer sheath 130. Under the lattice disconnect tubes 142, the drive wires 150 are removably connected to the proximal end of each jack screw 220 so that, as long as the lattice disconnect tubes 142 remain in this distally disposed state adjacent the proximal end of the adjustable stent lattice 210, the drive wires 150 are rotationally fixed to the proximal end of each jack screw 220, which means that, as a drive wire 150 rotates, the respective jack screw 220 rotates correspondingly. The non-illustrated delivery and deployment handle controls expansion and contraction of the adjustable stent lattice 210 and deployment of the implant 200 by rotation of the drive wires 150 and, when deployment is desired, by proximal movement of the disconnect lumens 140, which, when moved proximally, translate the lattice disconnect tubes 142 away from the connection between the drive wires 150 and the expansion/contraction assembly of the adjustable stent lattice 210 (see jack screws below) to permit automatic separation of the drive wires 150 and the jack screws.

Figure 3:
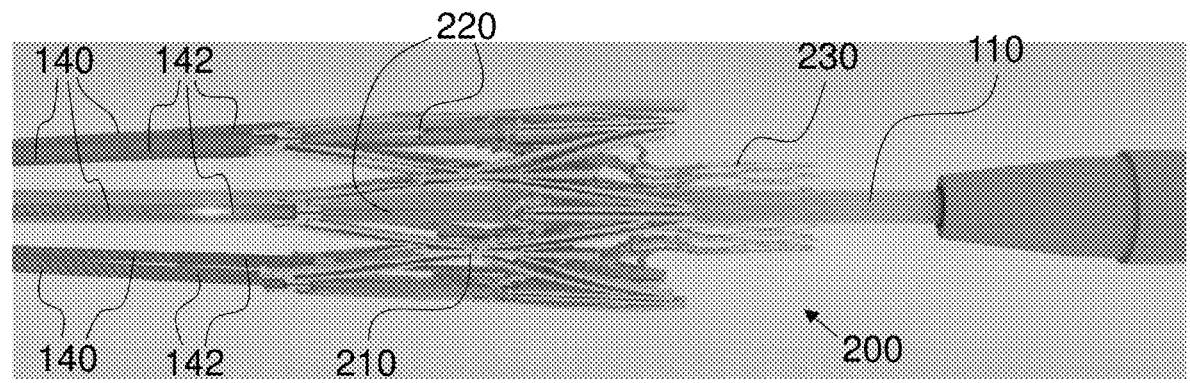
FIG. 3 is a fragmentary, side perspective view of the distal end of the delivery system of FIG. 1 with the mitral valve replacement implant of FIG. 2 in a pre-installation orientation with the outer sheath retracted from the implant drive wires.

The self-expanding valve trampoline lattice 230 is disposed within a central orifice of the adjustable stent lattice 210 and is attached to the adjustable stent lattice 210. FIG. 3 shows the sheath 130 entirely removed from the implant 200 and the lattice disconnect tubes 142. Here, the adjustable stent lattice 210 is further expanded towards its pre-defined self-expanding shape. Visible in FIG. 3 is the connection location of the drive wire connectors 152 and the proximal end of the jack screws 220, but that connection is hidden within the respective lattice disconnect tubes 142.

FIG. 4 illustrates the implant 200 in approximately its fully self-expanded state. The exterior implant skirt 240 and the valve trampoline lattice 230 are shown but are transparent in this figure. As will be explained in further detail below, the implant skirt 240 is attached (e.g., with sutures in the shape of an "X") to the exterior surfaces of the adjustable stent lattice 210.

Figure 6:
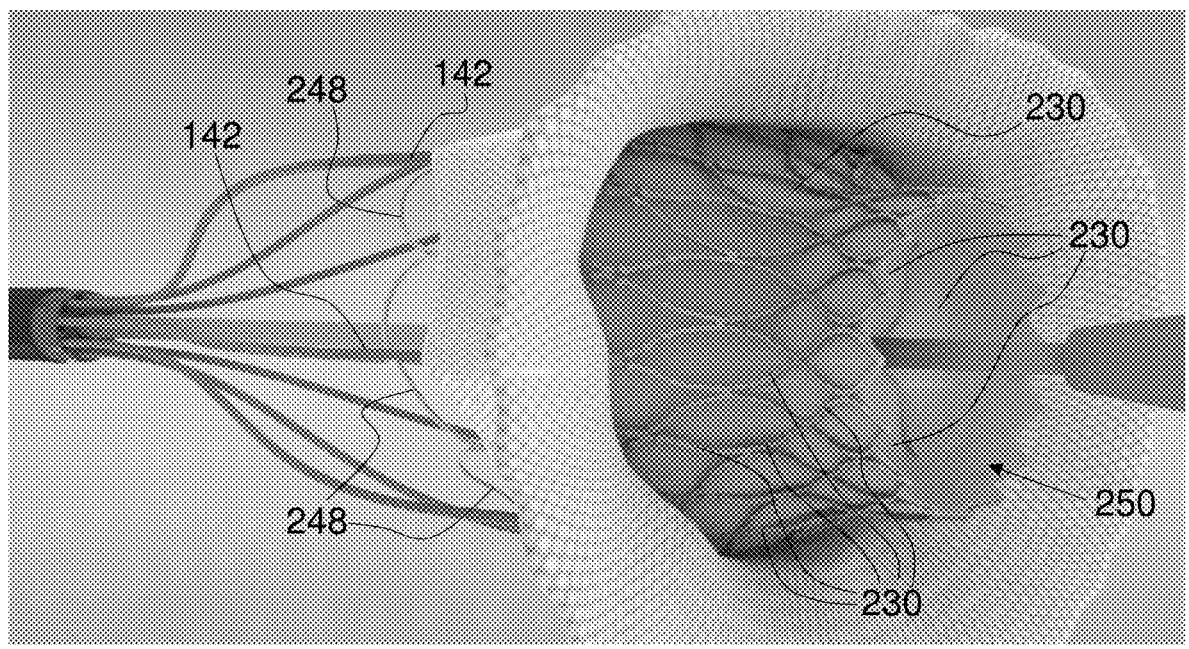
FIG. 6 is a fragmentary, perspective view of the distal end of the delivery system of FIG. 1 with the mitral valve replacement implant of FIG. 5 in a fully-expanded, delivery orientation with the drive wires still engaged to the implant and constraining atrium wall retainers.

FIG. 5 illustrates the implant 200 in a partially forcibly expanded state and FIG. 6 illustrates the implant 200 in a further expanded state. The implant 200 is rotated in FIG. 6 to show more of the left ventricle side of the implant, i.e., the side of the implant configured to be positioned with the left ventricle of the patient. Here, the exterior implant skirt 240 and the valve trampoline lattice 230 are fully resolved and, therefore, the implant skirt 240 covers the adjustable stent lattice 210 so that it is no longer visible. The self-expanding, memory shaped skirt lattice 242 is visible beneath the exterior material 244 of the implant skirt 240 for clarity. The material 244 can be made from anything that is fluid-tight or resistant and retains that fluid-tight or resistant characteristic even after being attached to the skirt lattice 242 or to the adjustable stent lattice 210 with sutures that puncture the material 244, for example. The material 244 can be a woven polyester fabric, a sheet of plastic, and/or a sheet of pericardial tissue, for example. Preferably, the material 244 is of braided polyester coated with polyurethane. As can be seen on the exterior surface of the material 244, sutures 246 (e.g., in the shape of an "X") fixedly attach the material 244 and the skirt lattice 242 to the adjustable stent lattice 210 therein such that, as the adjustable stent lattice 210 expands, both the skirt lattice 242 and the material 244 expands correspondingly, as is shown, for example, in the transition from FIG. 5 to FIG. 6.

Extending proximally from skirt lattice 242 (and being part of the skirt lattice 242) are left-atrium wall-retaining petals 248. Even though the material 244 prevents viewing of the entire extent of the retaining petals 248, it can be seen in FIGS. 5 and 6 that the lattice disconnect tubes 142 are disposed radially outside the retaining petals 248 but inside the skirt lattice 242/material 244. In this manner, the petals 248 are prevented from expanding radially outwards until the lattice disconnect tubes 142 are disconnected from the adjustable stent lattice 210. FIG. 6 shows the implant 200 in an exemplary fully-expanded, delivery orientation with the drive wires 150 still engaged to the implant 200. It is noted that the circular shape of the retaining petals 248 is only one exemplary configuration for retaining the implant 200 on the atrium side of the mitral valve annulus. These petals 248 can take any shape that, after being allowed to pivot in a direction from the guidewire lumen 110 radially outward, allows the implant 200 to be secured on the atrium side.

Figure 7:
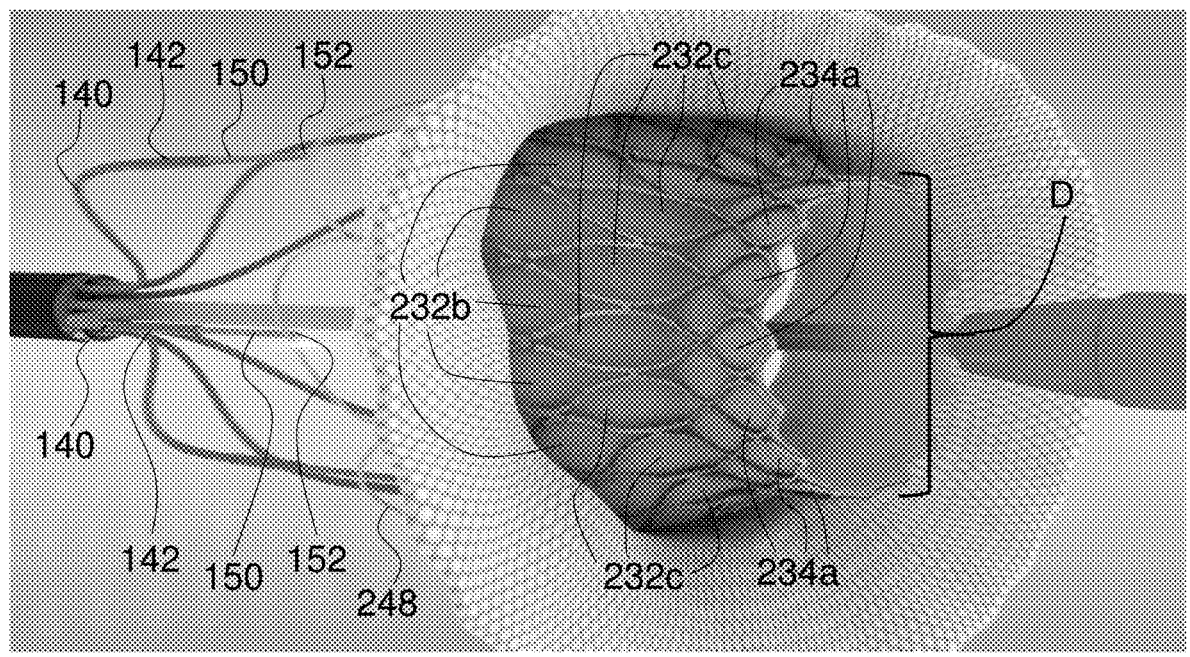
FIG. 7 is a fragmentary, perspective view of the distal end of the delivery system of FIG. 1 with the mitral valve replacement implant of FIG. 5 having the drive wires disengaged from the implant and from the atrium wall-retaining structures.
Figure 8:
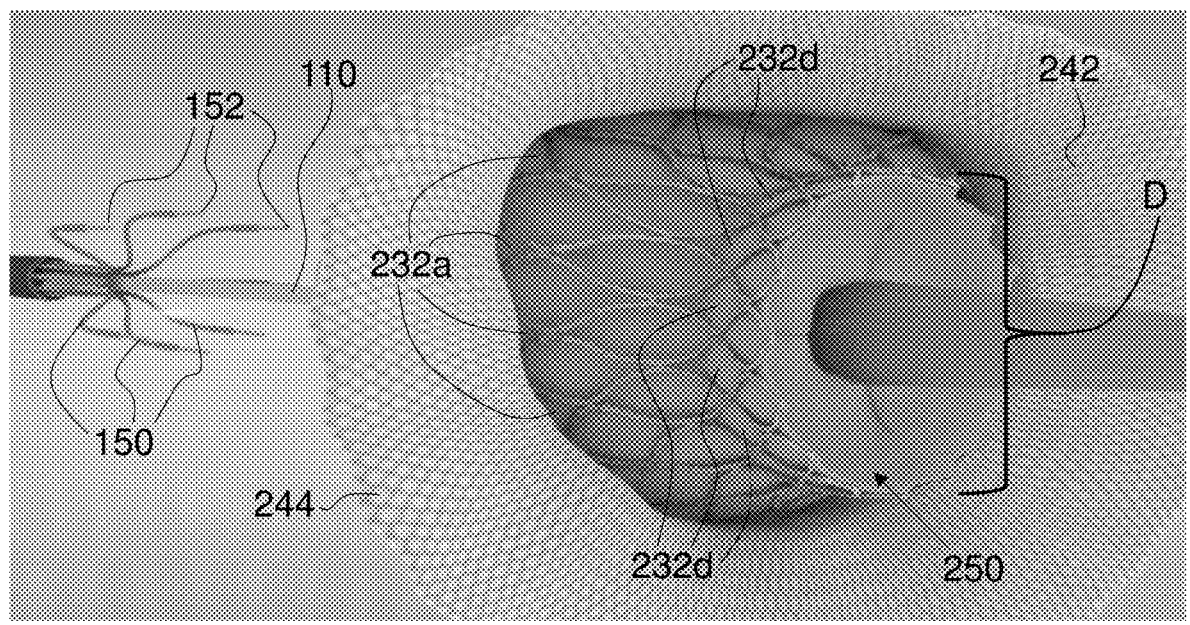
FIG. 8 is a fragmentary, perspective view of the distal end of the delivery system of FIG. 1 with the mitral valve replacement implant of FIG. 7 having the drive wires in a further retracted position from the implant and with the nosecone in a retracted state within the implant.
Figure 9:
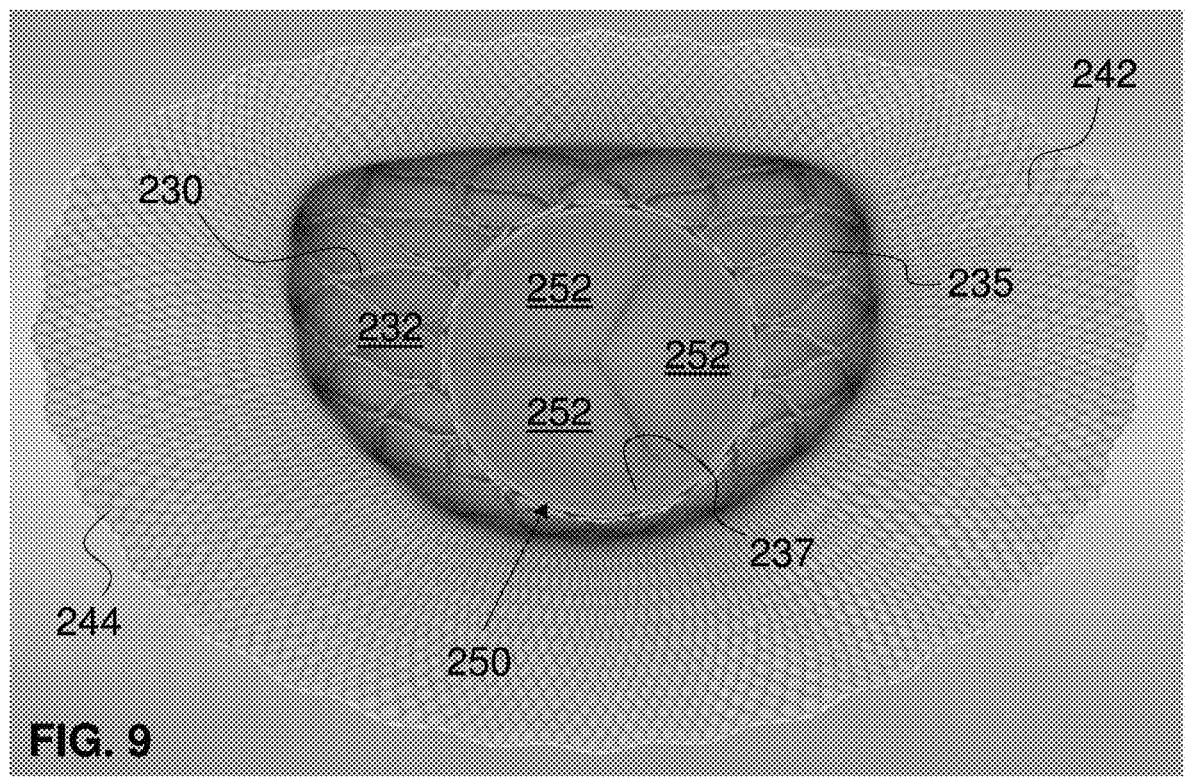
FIG. 9 is a ventricle-side elevational view of the mitral valve replacement implant of FIG. 8 with the mitral valve leaflets closed and with the D-shape of the self-expanding valve trampoline lattice visible.
Figure 10:
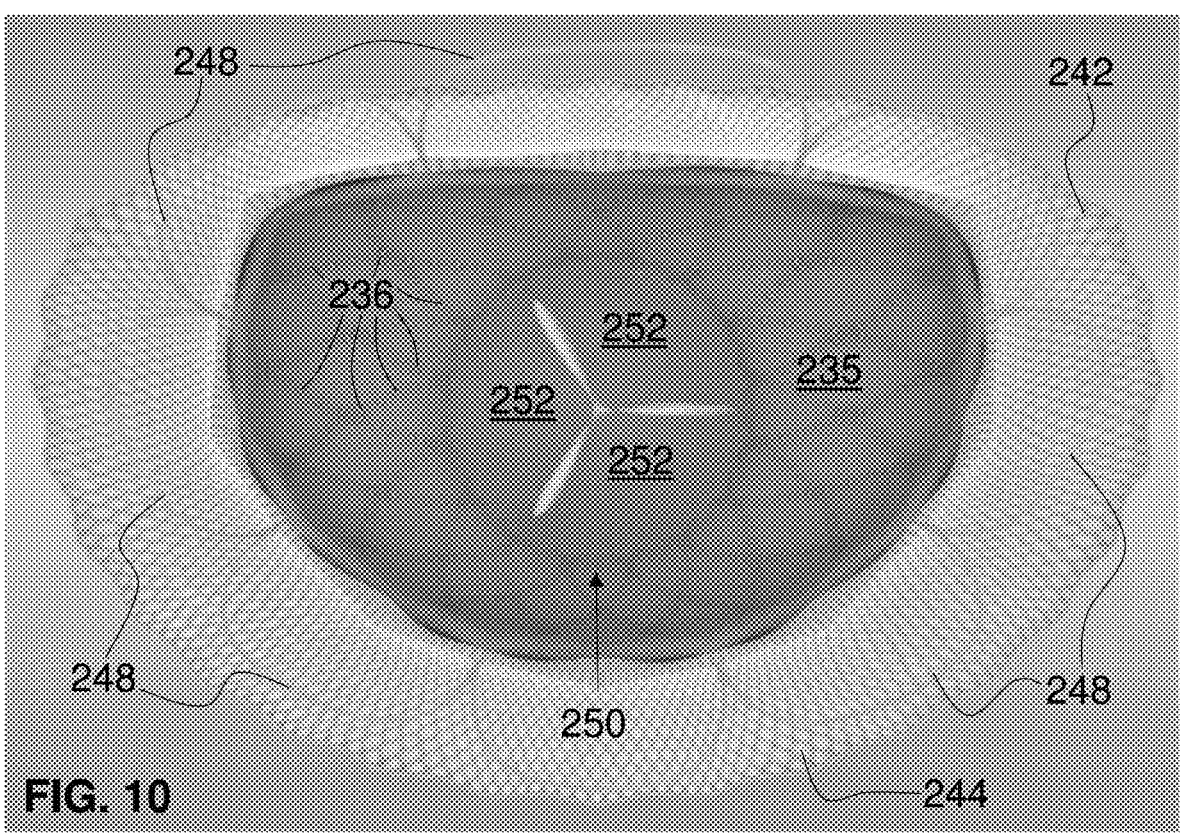
FIG. 10 is an atrium-side elevational view of the mitral valve replacement implant of FIG. 8 with the valve leaflets in an almost-closed state.
Figure 11:
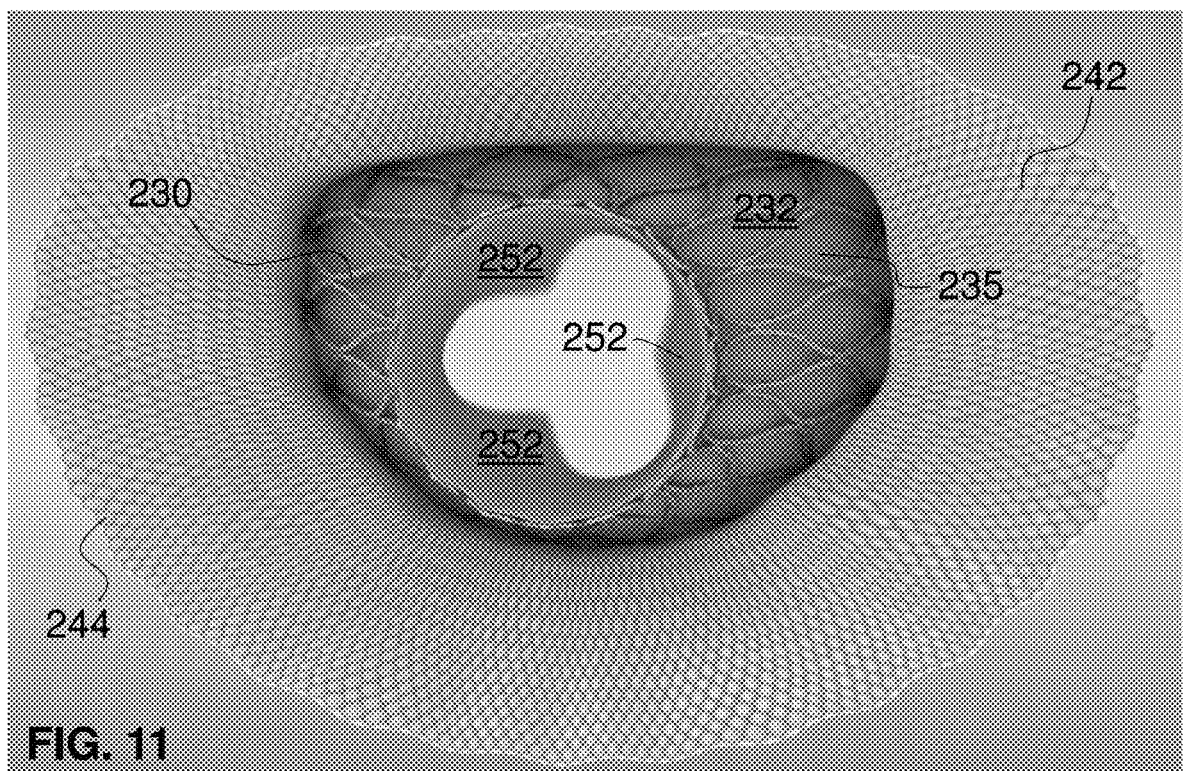
FIG. 11 is a ventricle-side perspective view of the mitral valve replacement implant of FIG. 9 with the valve leaflets partially open.
Figure 12:
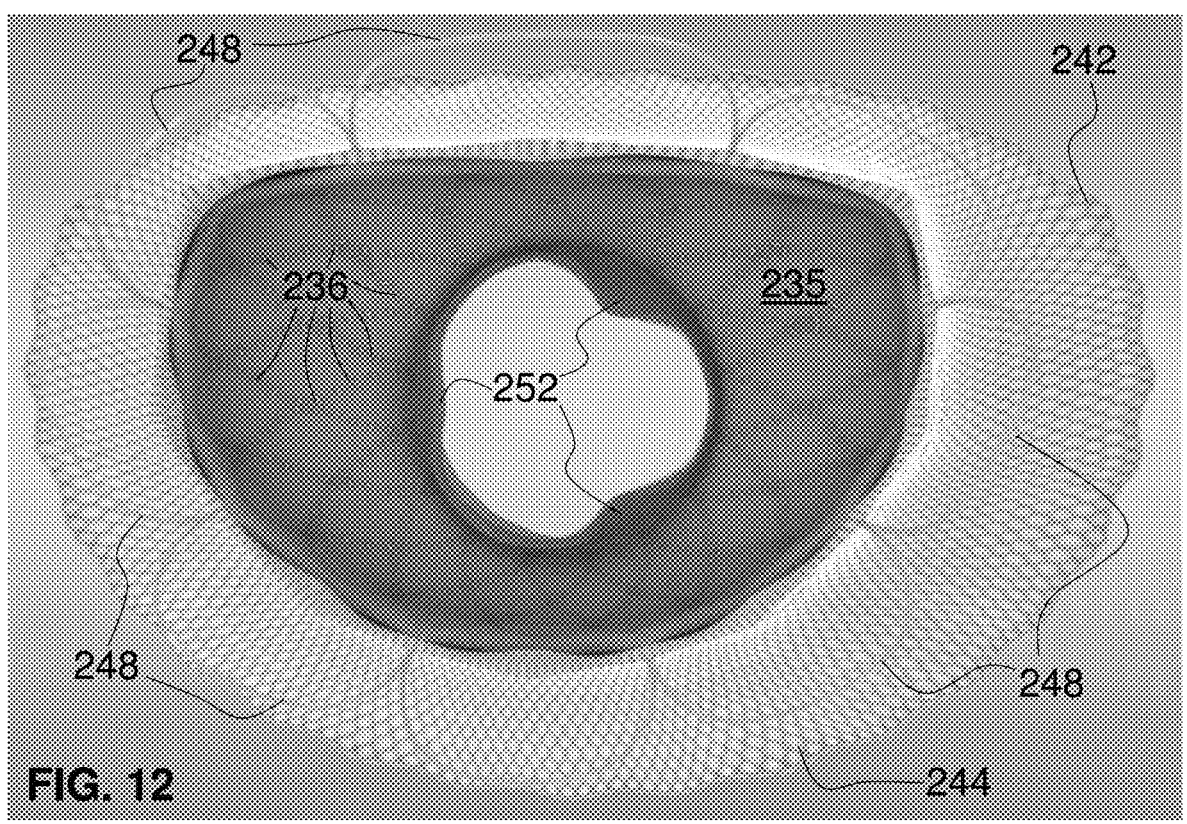
FIG. 12 is an atrium-side perspective view of the mitral valve replacement implant of FIG. 9 with the valve in a substantially open state.
Figure 13:
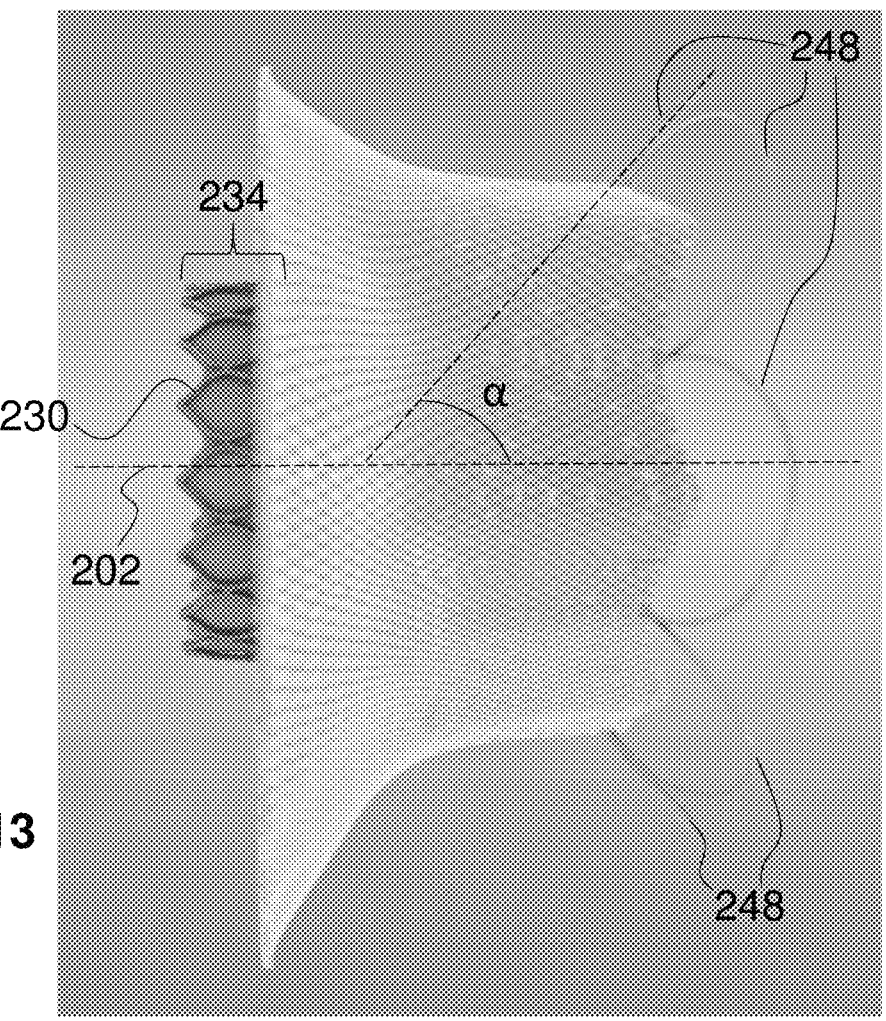
FIG. 13 is a side elevational view of the mitral valve replacement implant of FIG. 15 with attachment points connecting the skirt lattice and the skirt fabric to the adjustable stent lattice.

When the implant 200 is positioned in a final desired orientation, such as that shown in FIGS. 7 through 13, the drive wires 150 are to be disconnected from all of the jack screws 220 and, thereafter, removed from the patient. To disengage the drive wires 150, a non-illustrated control handle moves each of the disconnect lumens 140 proximally (either simultaneously or separately) to thereby slide the hollow disconnect tubes 142 away from the adjustable stent lattice 210. When this covering is removed, the temporary connection of the drive wire connectors 152 and the proximal ends of the jack screws 220 can be allowed to separate from one another, as shown in FIG. 7, allowing the disconnect lumens 140 and the drive wires 150 (and the sheath 130 if desired) to retract away from the adjustable stent lattice 210. The collapsed or contracted state of the wall-retaining petals 248 only remains while the disconnect lumens 140 and the drive wires 150 remain connected to the adjustable stent lattice 210. When disconnected therefrom, the petals 248 are allowed to move to their steady state or pre-set orientation, which is a position where the petals 248 extend in a plane that is substantially perpendicular to the axis of the guidewire lumen 110. Likewise, when allowed to self-expand, the skirt lattice 242 moves to its steady-state or pre-set orientation, which is a position where the edges of the skirt lattice 242 extend in a plane that is more perpendicular to the axis of the guidewire lumen 110 than parallel thereto. This orientation of the implant 200 secured in a target location, such as the mitral valve annulus, is depicted in the views of FIGS. 9 to 12 and, in particular, in the side elevational view of FIG. 13. As can be seen in FIG. 13, the angle α between the petals 248 and the central axis 202 of the implant 200 is between approximately 45 degrees and approximately 90 degrees including every number therebetween. In particular, the angle α is between approximately 50 degrees and approximately 75 degrees including every number therebetween.

Also shown in FIGS. 5 to 13 is the structure of the valve trampoline lattice 230, including a centrally disposed valve 250, which, in this exemplary embodiment, is a replacement for a mitral valve. More particularly, as shown in FIG. 5, the self-expanding valve trampoline lattice 230 has an expandable outer trampoline portion 232 and an expandable but fixed maximum diameter inner circumferential valve portion 234, which can be cylindrical and, for example, fabricated from a laser-cut, nitinol tube. The outer trampoline portion 232 connects on its exterior circumference to an interior circumference of the adjustable stent lattice 210. The connection can be integral or can be formed, for example, by crimping, banding, and/or welding. Deformable cells of the outer trampoline portion 232 allow the outer trampoline portion 232 to expand and contract substantially. In this example, the cells are substantially marquis-shaped or tear-drop shaped, but they can take other closed curved or straight shapes. More particularly in the exemplary embodiment of FIGS. 5 to 13, the valve trampoline lattice 230 has figure-eight-shaped structures that, when attached together at their sides, form five rows of cells that circumscribe the valve trampoline lattice. The outer trampoline portion 232 includes the first four rows of tear-drop and marquis-shaped cells. A first row of relatively smaller tear-drop-shaped cells 232a (see FIGS. 7 and 8) are sixteen in number and define an outermost ring of outer trampoline portion 232 cells. A second row of relatively larger marquis-shaped cells 232b, also sixteen in number, define a first inner ring of the outer trampoline portion 232. A third row of sixteen marquis-shaped cells 232c narrower and longer than the cells 232b define a second inner ring of the outer trampoline portion 232. Finally, a fourth row of sixteen smallest marquis-shaped cells 232d define a third inner ring of the outer trampoline portion 232. In comparison, the inner circumferential valve portion 234 of the valve trampoline lattice 230 has one row of sixteen cells 234a about its circumference, each cell having a longitudinal length that is about the same as the circumferential width. Accordingly, these sixteen cells 234a are substantially circular, even though they have tear-drop tips on either end. The substantially circular nature of the sixteen cells 234a creates a cylinder at the interior end of the valve trampoline lattice 230. This compound structure allows the inner circumferential valve portion 234 to remain substantially circular even while the outer trampoline portion 232 expands and contracts with expansion or contraction of the adjustable stent lattice 210.

Accordingly, when the adjustable stent lattice 210 expands or contracts, the outer circumference of the outer trampoline portion 232 correspondingly expands or contracts without limitation. The inner circumferential valve portion 234 connects to the outer trampoline portion 232 at cell connection points 233. This inner circumferential valve portion 234 is not D-shaped and does not have cells that allow it to expand and contract in the same way that the cells of the outer trampoline portion 232 permit unrestricted expansion. Instead, in this exemplary configuration, the cells of the inner circumferential valve portion 234 only allow expansion up to a pre-determined state once the adjustable stent lattice 210 is expanded far enough to no longer constrain the inner circumferential valve portion 234. At that state, which is shown starting at FIG. 6, the cells forming the outer circumference of the inner circumferential valve portion 234 are disposed about the central axis 202 of the implant 200 in a substantially circular manner defining a pre-determined maximum diameter D, shown in FIGS. 7 and 8 and continues in FIGS. 9 to 13. Thus, no matter how far the adjustable stent lattice 210 expands the outer trampoline portion 232 of the trampoline lattice 230, the inner circumferential valve portion 234 will not expand past the diameter D.

The reason why the trampoline lattice 230 is referred to as a "trampoline" is because of the way that it supports the valve 250. At the inner circumferential valve portion 234, the trampoline lattice 230 is substantially constant after the adjustable stent lattice 210 has expanded to no longer restrict the inner circumferential valve portion 234. The outer trampoline portion 232, in contrast, expands to whatever shape is needed to bridge the gap between the inner circumferential valve portion 234 and the adjustable stent lattice 210. Thus, the outer portion 232 acts as a stretchable "trampoline" to move and adjust to whatever shape is needed to suspend the relatively stable inner circumferential valve portion 234 (and the valve 250) at the central region of the trampoline lattice 230. The natural shape of the outer trampoline portion 232 corresponds to the inner circumference of the adjustable stent lattice 210, which means it has a natural D-shaped circumference.

Both the outer trampoline portion 232 and the inner circumferential valve portion 234 are fluid-tightly sealed to the material 244 so that, when installed, the implant 200 forms a fluid-tight seal that only permits fluid flow through the valve 250. As shown best in FIGS. 9 and 10, a first sealing material 235 is secured to the inside surfaces of the outer trampoline portion 232 and a second sealing valve material 237 is secured to the inside surfaces of the inner circumferential valve portion 234. The second sealing valve material 237 can be a single sheet with three leaflets cut therein or it can be a set of three separate leaflet portions individually connected to the interior surfaces of the inner circumferential valve portion 234. The material 235 can be a woven polyester fabric, a sheet of plastic, and/or a sheet of pericardial tissue, for example. The material 237 can be pericardial tissue or a natural valve harvested from a mammal, such as a porcine valve. In this exemplary embodiment, the second sealing valve material 237 extends from the distal most ends of the inner circumferential valve portion 234 to the center of the valve 250 and, thereby, forms the leaflets 252 of the valve 250, which, in this embodiment, is a tricuspid form (i.e., three leaflets 252). The tricuspid form is not to be considered as limiting and can have any number of leaflets. The first sealing material 235 and the second sealing valve material 237 can be separate, with the leaflets 252 extending into the central orifice of the inner circumferential valve portion 234 from either the first or second materials 235, 237, or they can be integral, with the leaflets 252 being a part of the material portions 235, 237 and extending into the central orifice of the inner circumferential valve portion 234.

With the petals 248 on the atrium side of the now-installed implant 200 and the skirt lattice 242 with its material 244 on the ventricle side of the implant 200, the diseased mitral valve annulus is captured and surrounded by the implant 200 in a liquid-tight and leak-free manner. Viewed in a cross-sectional plane extending along the axis of the guidewire lumen 110, therefore, the petals 248 and the skirts lattice 242 with the material 244 forms a U-shaped annular raceway as depicted in FIG. 13.

Figure 14:
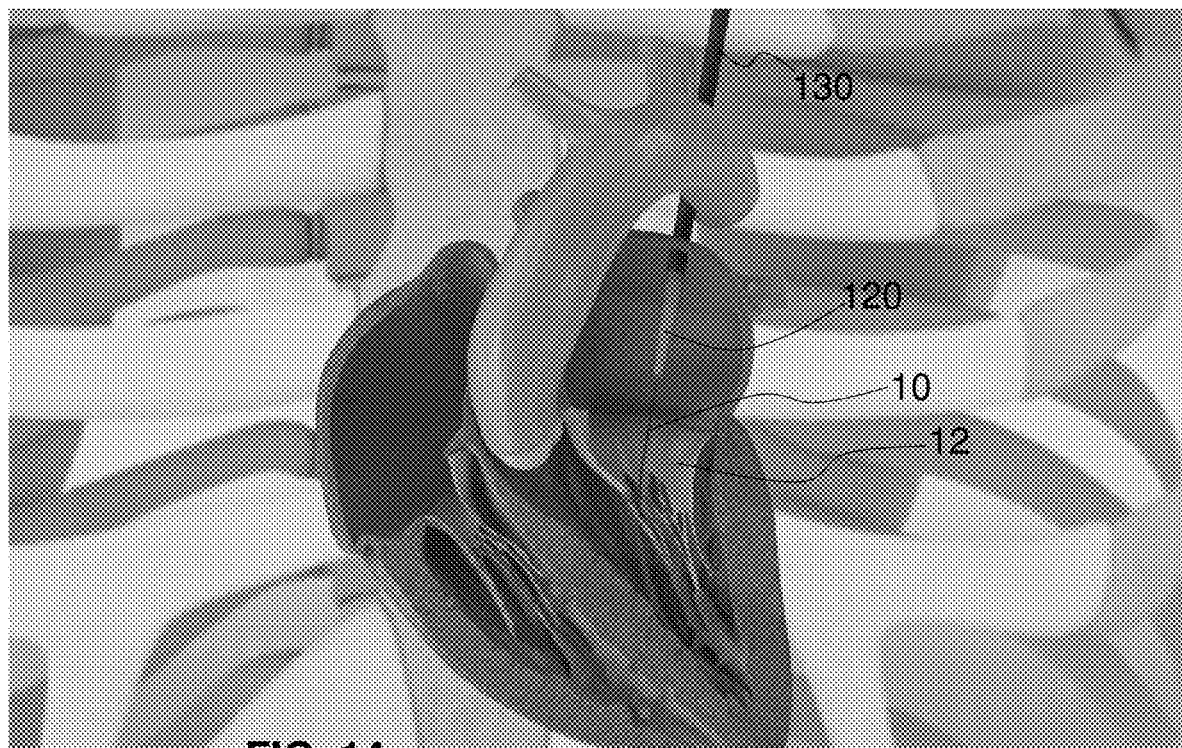
FIG. 14 is a fragmentary, perspective view of the delivery system of FIG. 1 for the actively controllable mitral valve replacement implant in a vertical cross-section of a human heart and with the guidewire in the left ventricle and the nosecone entering the left atrium of a ventricle-contracted heart.
Figure 15:
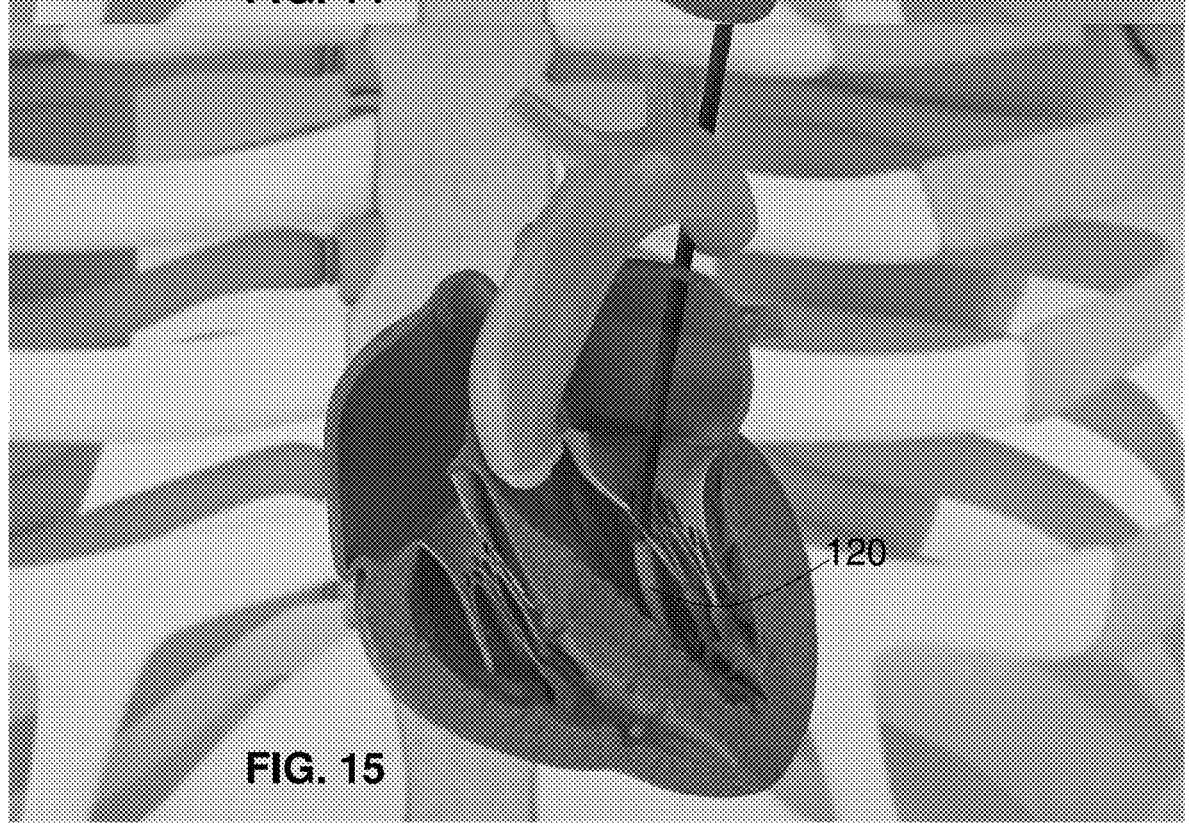
FIG. 15 is a fragmentary, perspective view of the delivery system of FIG. 14 with the nosecone in the left ventricle of a ventricle-relaxed heart.
Figure 16:
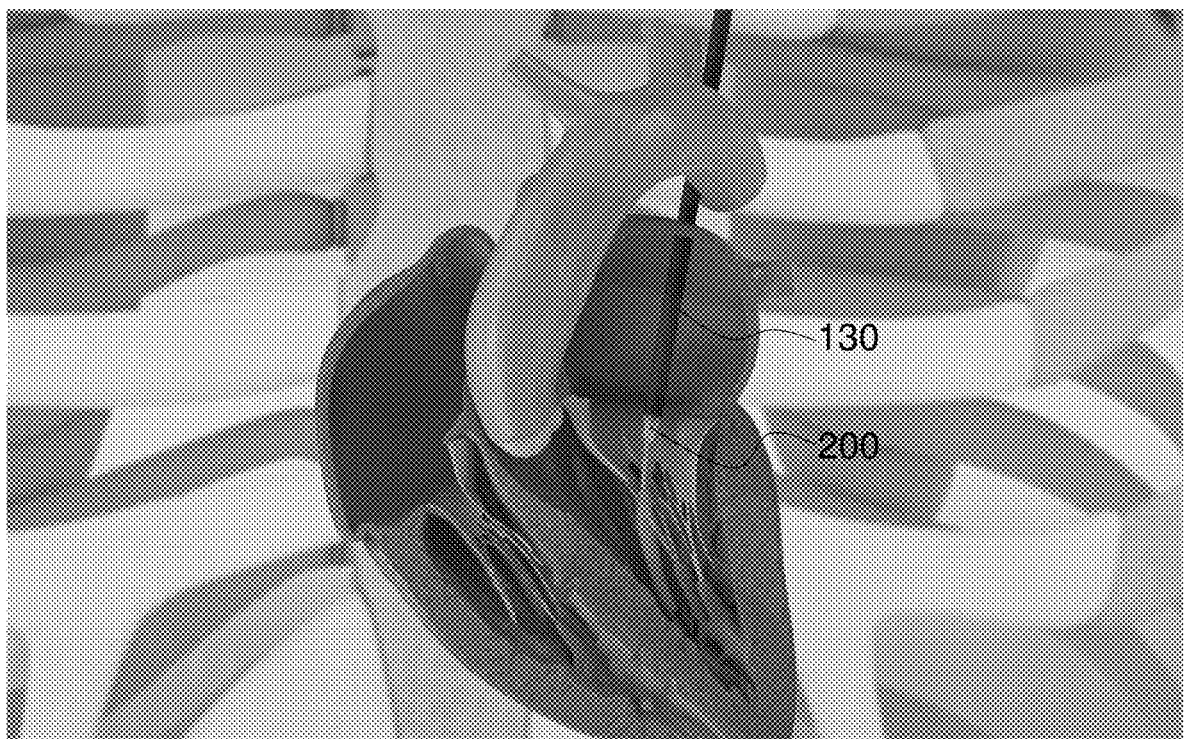
FIG. 16 is a fragmentary, perspective view of the delivery system of FIG. 15 with the outer sheath withdrawn into the left atrium and the mitral valve replacement implant beginning to show within a ventricle-contracted heart.
Figure 17:
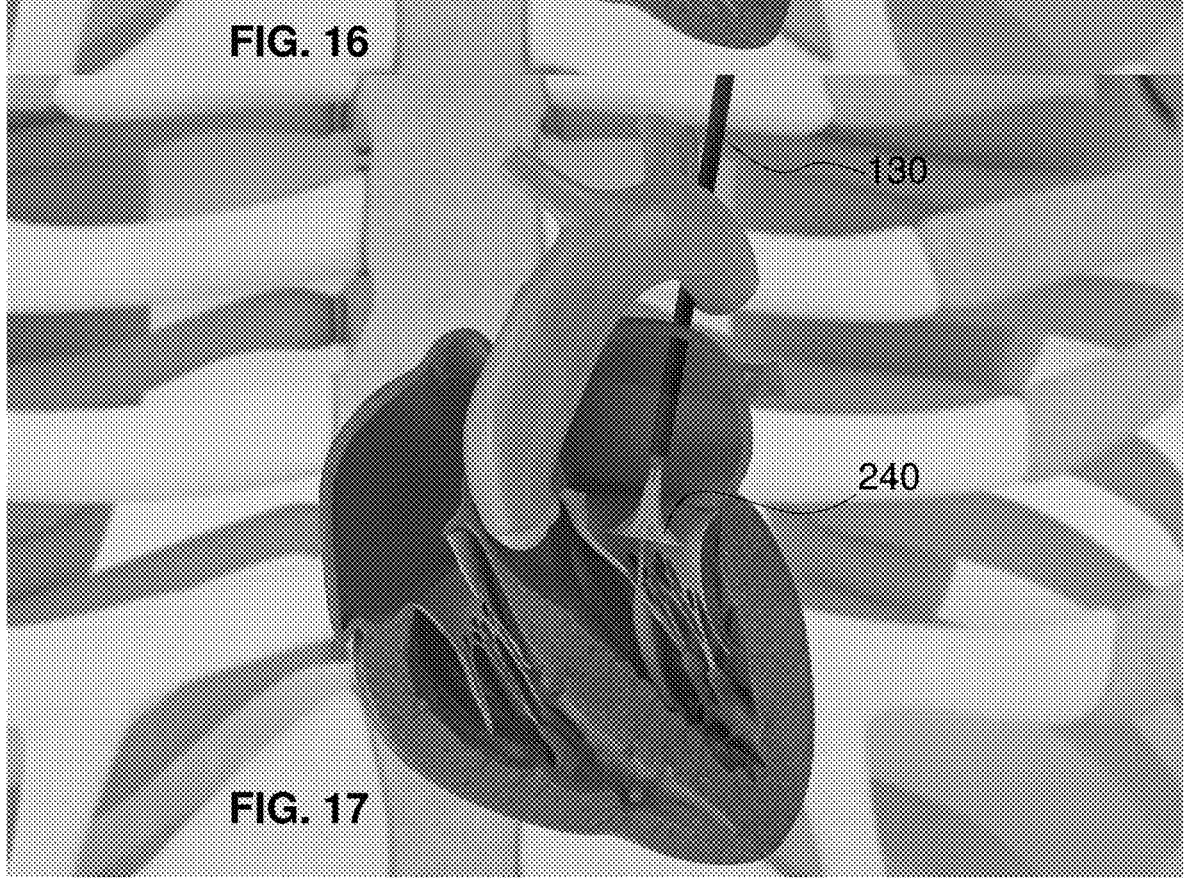
FIG. 17 is a fragmentary, perspective view of the delivery system of FIG. 16 with the outer sheath substantially withdrawn over the mitral valve replacement implant and the implant skirt in a first self-expanded orientation within the mitral valve orifice of a ventricle-relaxed heart.
Figure 18:
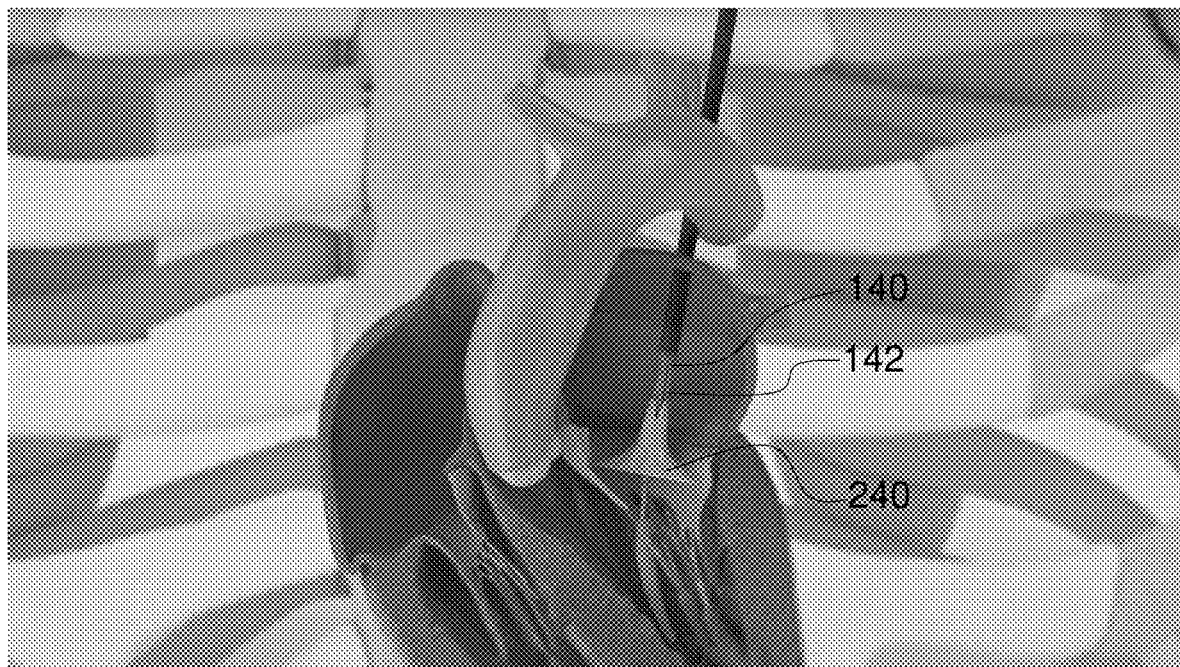
FIG. 18 is a fragmentary, perspective view of the delivery system of FIG. 17 with the implant skirt in a second self-expanded orientation within the mitral valve orifice and with the drive wires of the mitral valve replacement implant partially visible within a ventricle-contracted heart.
Figure 19:
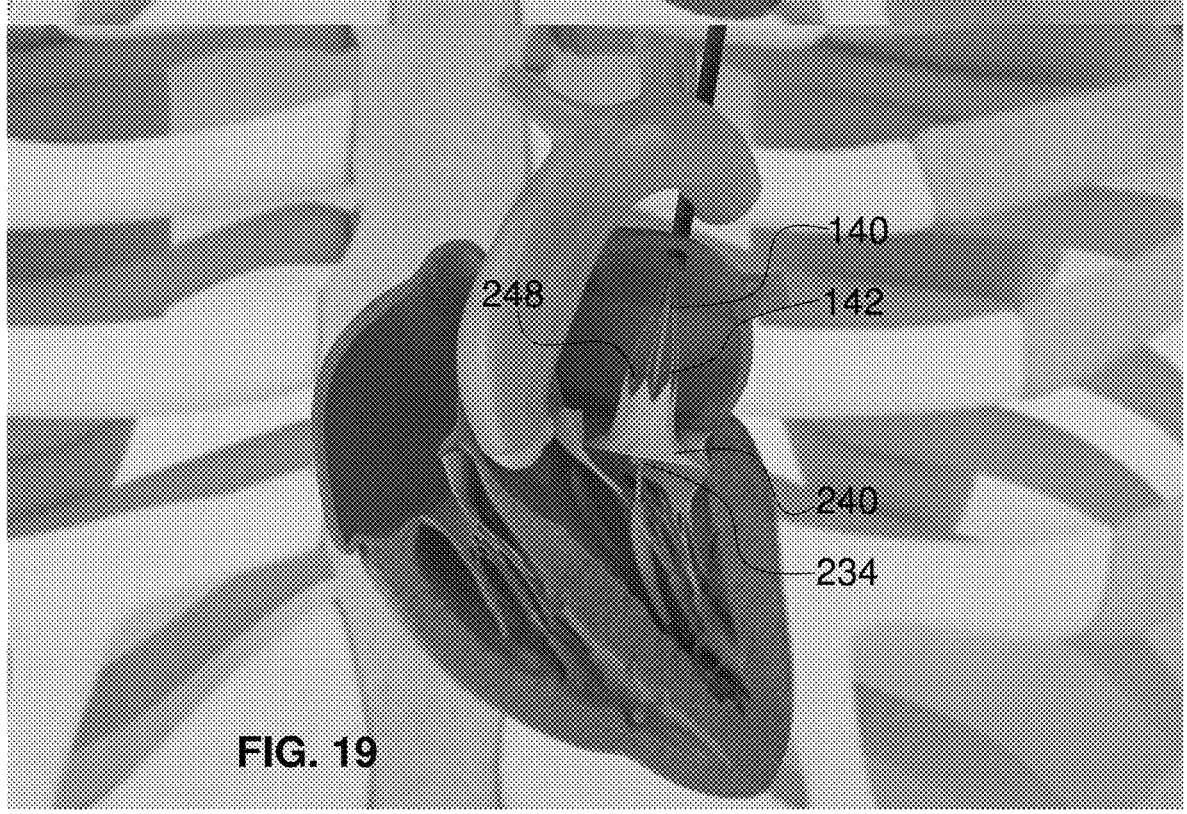
FIG. 19 is a fragmentary, perspective view of the delivery system of FIG. 18 with the implant skirt in a third self-expanded orientation within the mitral valve orifice and with the drive wires of the mitral valve replacement implant visible within a ventricle-contracted heart.
Figure 20:
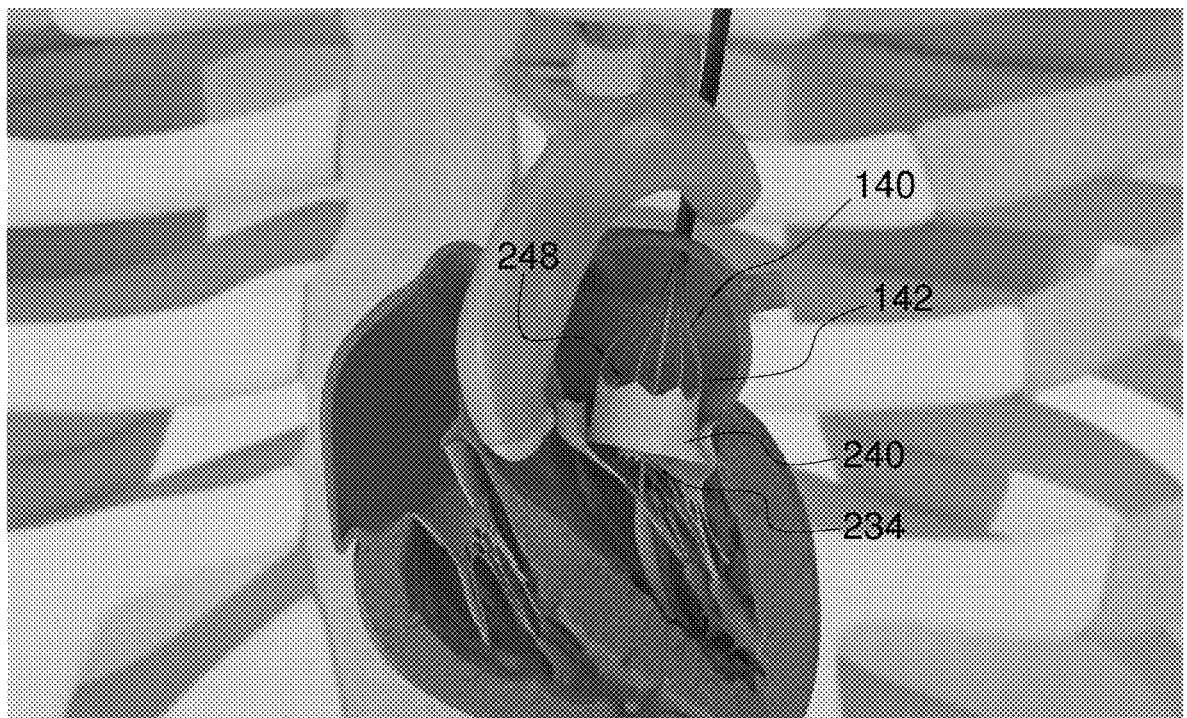
FIG. 20 is a fragmentary, perspective view of the delivery system of FIG. 19 with the adjustable stent lattice in a forcibly expanded orientation within the mitral valve orifice of a ventricle-relaxed heart.
Figure 21:
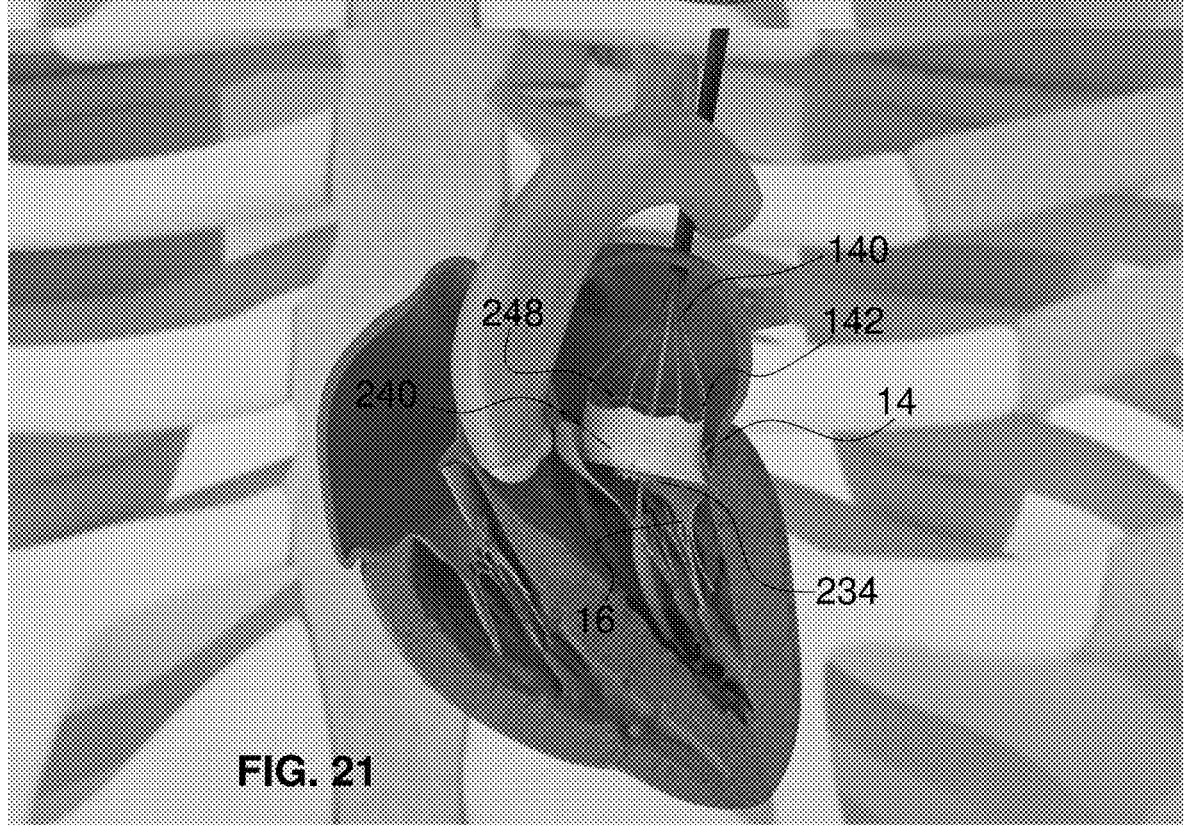
FIG. 21 is a fragmentary, perspective view of the delivery system of FIG. 20 with the adjustable stent lattice and the implant skirt in a fully expanded and implanted orientation within the mitral valve orifice of a ventricle-contracted heart before disconnection of the drive wires.

This capture of the native mitral valve annulus is depicted in the progression of FIGS. 14 to 22, which is an example of replacement mitral valve implantation with a transapical approach. In FIG. 14, a guidewire 10 has been installed through the atrium wall and the diseased mitral valve 12 and rests in the left ventricle. The guidewire lumen 110 is threaded onto the guidewire 10 and the guidewire lumen 110 enters the left atrium preceded by the distally connected nosecone 120. The nosecone 120 of the delivery system 100 is extended into the left ventricle in FIG. 15. In FIG. 16, the outer sheath 130 has been withdrawn into the left atrium and the mitral valve replacement implant 200 contained within the sheath 130 starts to be exposed within the diseased mitral valve annulus. In FIG. 17, the outer sheath 130 has been withdrawn almost all of the way over the mitral valve replacement implant 200 to an extent where the implant skirt 240 is able to self-expand into and towards the sub-valvular structures below the diseased mitral valve annulus. In FIG. 18, the outer sheath 130 has been withdrawn completely from the mitral valve replacement implant 200 to an extent where the sheath 130 only constrains the disconnect lumens 140 and drive wires 150. The implant skirt 240 is further self-expanded into the sub-valvular structures below the diseased mitral valve annulus. In FIG. 19, the outer sheath 130 has been withdrawn completely to no longer radially constrain the disconnect lumens 140 or drive wires 150 to, thereby, allow the adjustable stent lattice 210 to self-expand to its pre-determined, memory shape. The implant skirt 240 is further self-expanded into and touching the sub-valvular structures below the diseased mitral valve annulus to an extent that it could reach and touch the chords beyond the native leaflet edges if sized appropriately. FIG. 20 shows the adjustable stent lattice 210 forcibly expanded radially outwards and the implant skirt 240 remaining secured against the sub-valvular structures below the diseased mitral valve annulus but also adapting to the forcibly expanded orientation of the internal adjustable stent lattice 210. Finally, FIG. 21 illustrates the mitral valve replacement implant 200 in a fully expanded and implanted orientation within the mitral valve annulus just before disconnection of the drive wires 150. As can be seen, the implant skirt 240 substantially engages the native leaflets 14 and chordae tendineae 16 to create a fluid tight seal at the mitral valve annulus.

Figure 22:
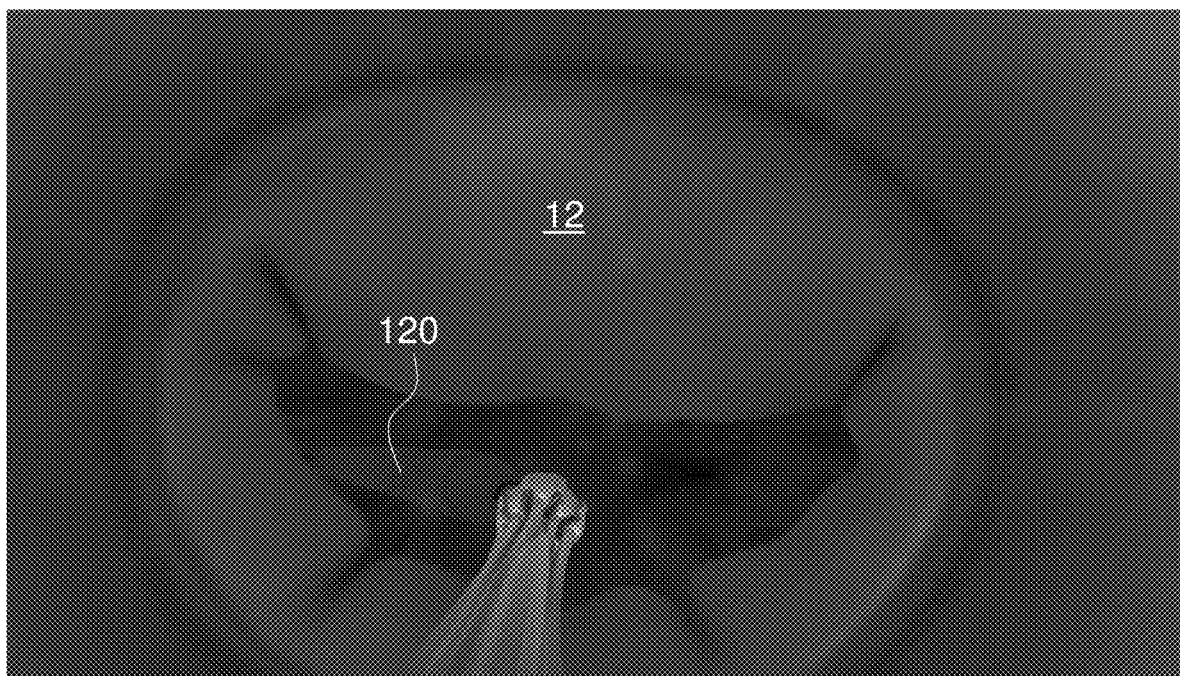
FIG. 22 is a fragmentary, perspective view of an exemplary embodiment of a sheath-constrained mitral valve replacement implant within a mitral valve orifice viewed from the left atrium with the mitral valve partially open, with the drive wires fully constraining the atrium retaining petals, and with the outer delivery sheath removed.
Figure 23:
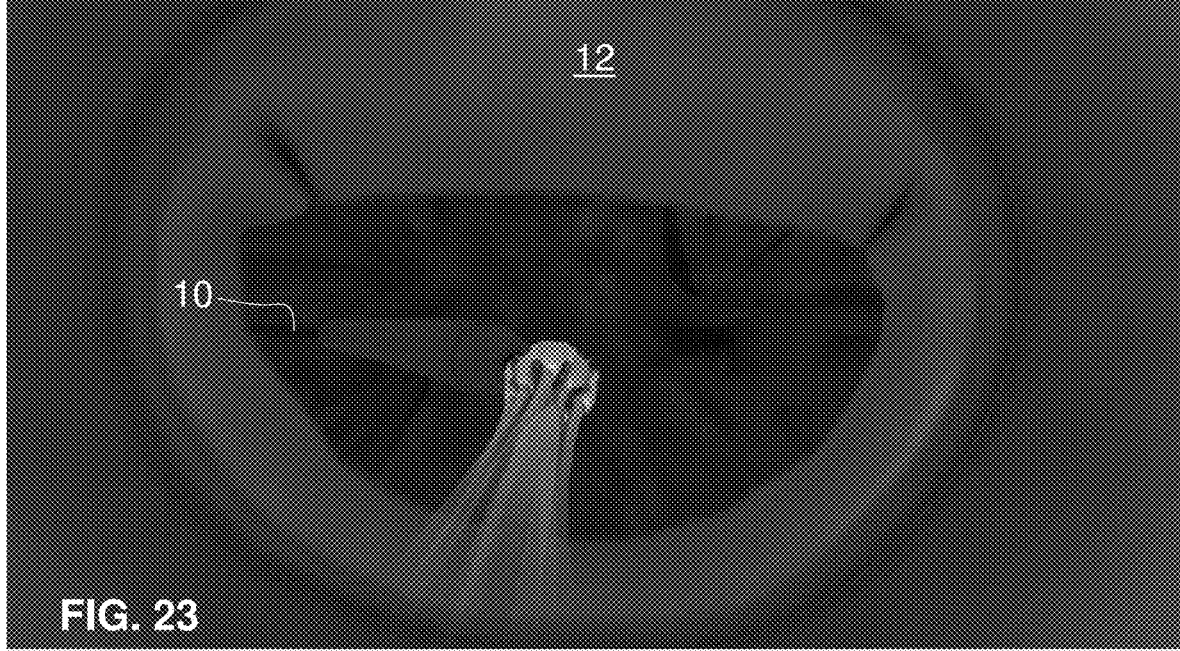
FIG. 23 is a fragmentary, perspective view of the sheath-constrained mitral valve replacement implant of FIG. 22 with the mitral valve fully open.
Figure 24:
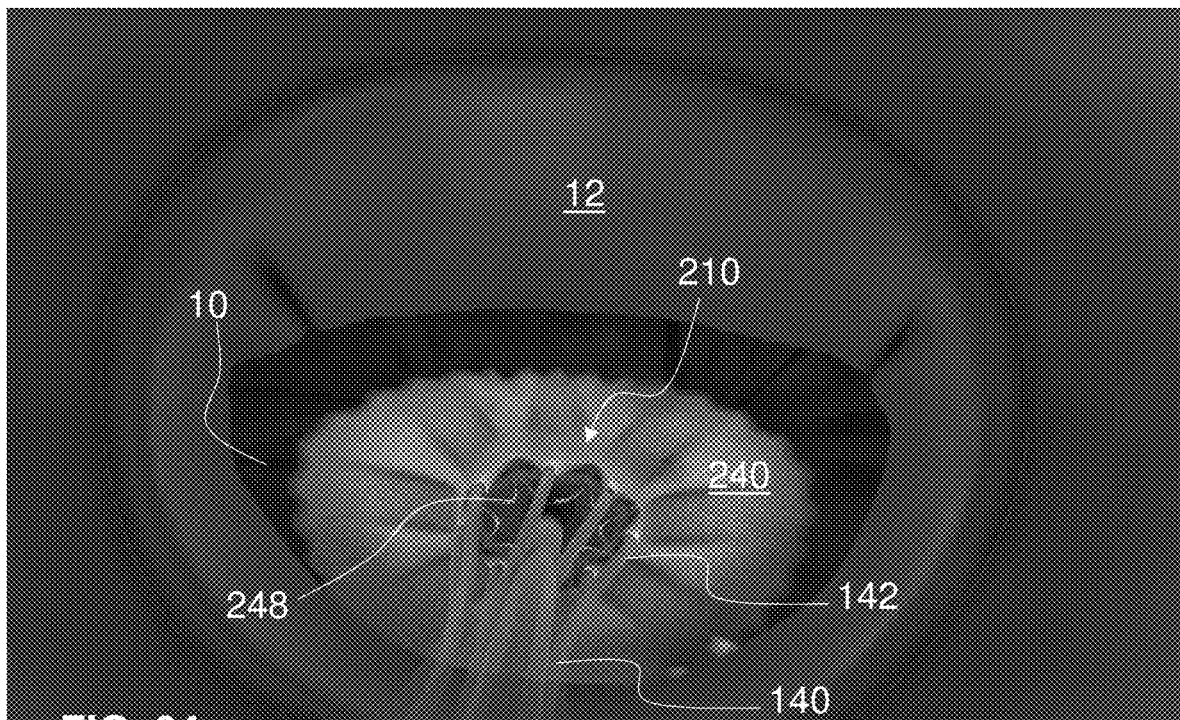
FIG. 24 is a fragmentary, perspective view of the mitral valve replacement implant of FIG. 23 with the sheath retracted and with the skirt of the mitral valve replacement implant in a self-expanded state with the mitral valve fully open and with the drive wires constraining the atrium retaining petals.
Figure 25:
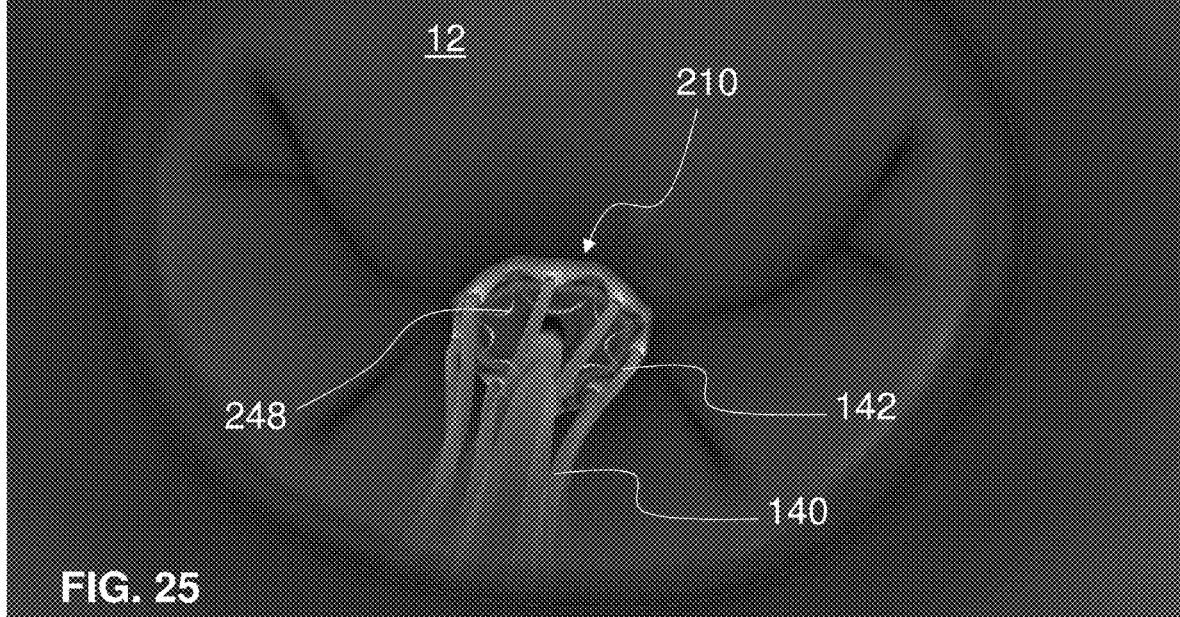
FIG. 25 is a fragmentary, perspective view of the mitral valve replacement implant of FIG. 24 with the mitral valve closed upon the skirt of the valve implant.
Figure 26:
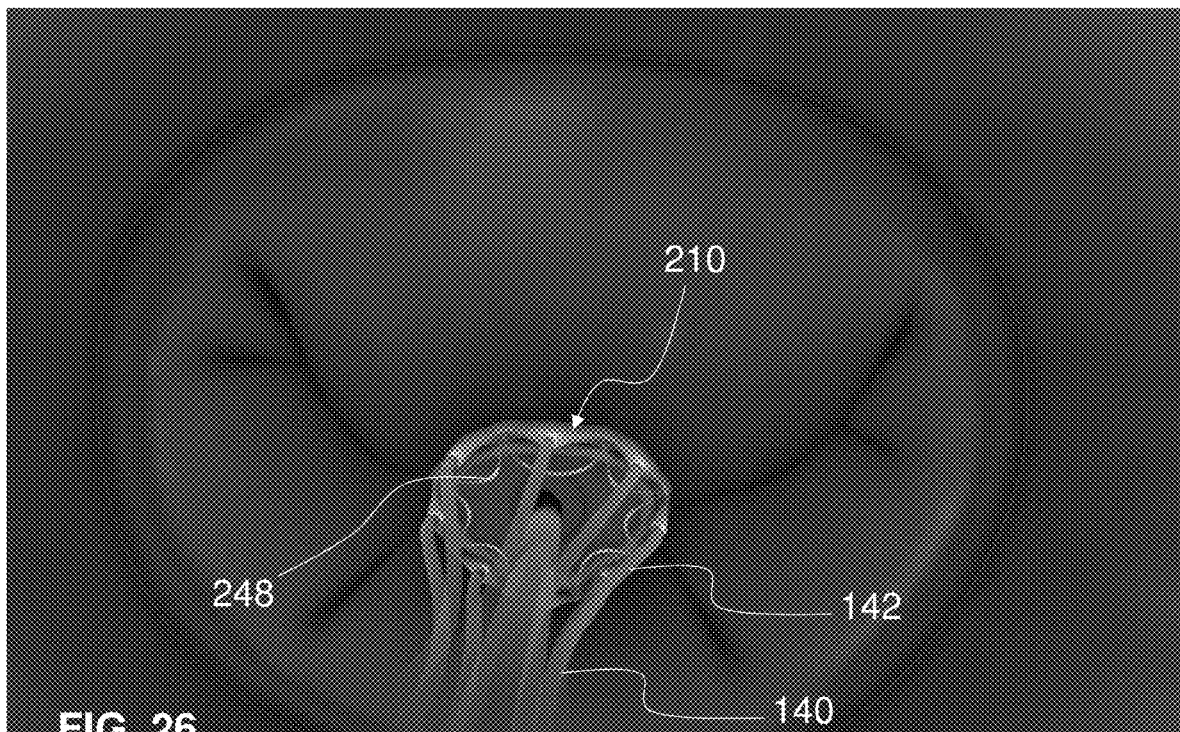
FIG. 26 is a fragmentary, perspective view of the mitral valve replacement implant of FIG. 25 in a fully self-expanded state with the mitral valve closed upon the mitral valve replacement implant.
Figure 27:
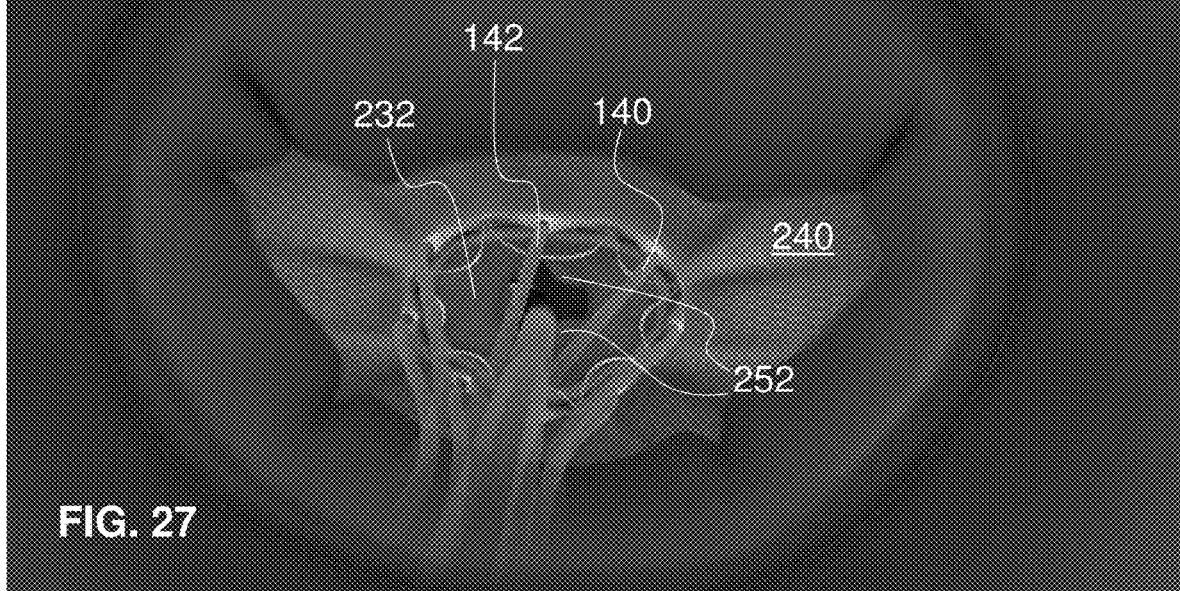
FIG. 27 is a fragmentary, perspective view of the mitral valve replacement implant of FIG. 26 in a forcibly expanded state with the mitral valve partially open around the mitral valve replacement implant and with the replacement valve of the mitral valve replacement implant partially open.
Figure 28:
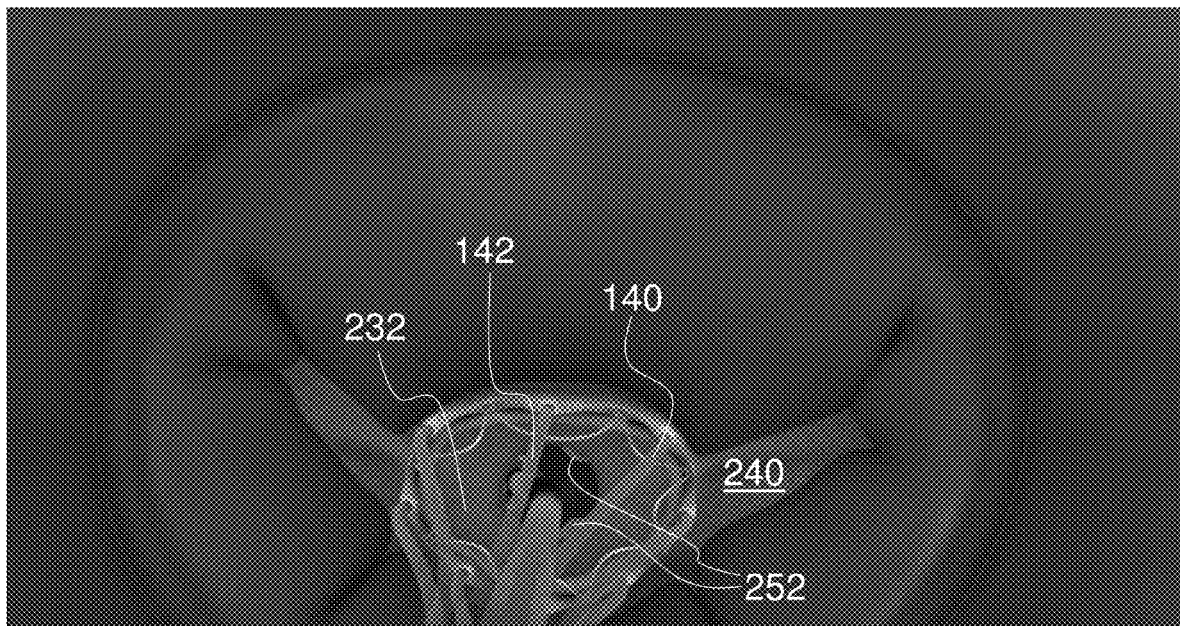
FIG. 28 is a fragmentary, perspective view of the mitral valve replacement implant of FIG. 27 in still a further forcibly expanded state with the mitral valve partially closed around the mitral valve replacement implant and with the replacement valve of the mitral valve replacement implant almost fully open.
Figure 29:
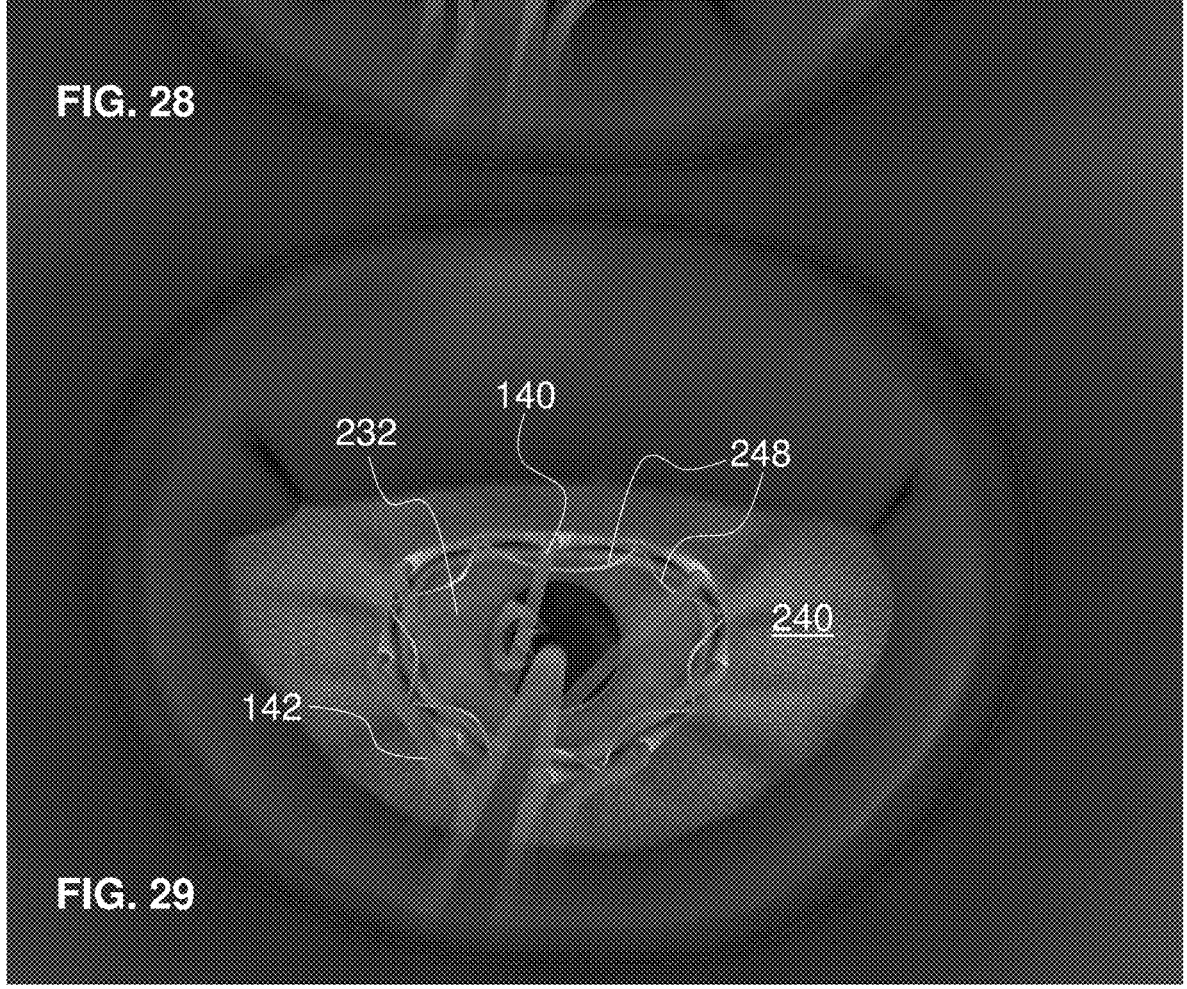
FIG. 29 is a fragmentary, perspective view of the mitral valve replacement implant of FIG. 28 in yet a further forcibly expanded state with the mitral valve open around the mitral valve replacement implant and with the replacement valve of the mitral valve replacement implant fully open.
Figure 30:
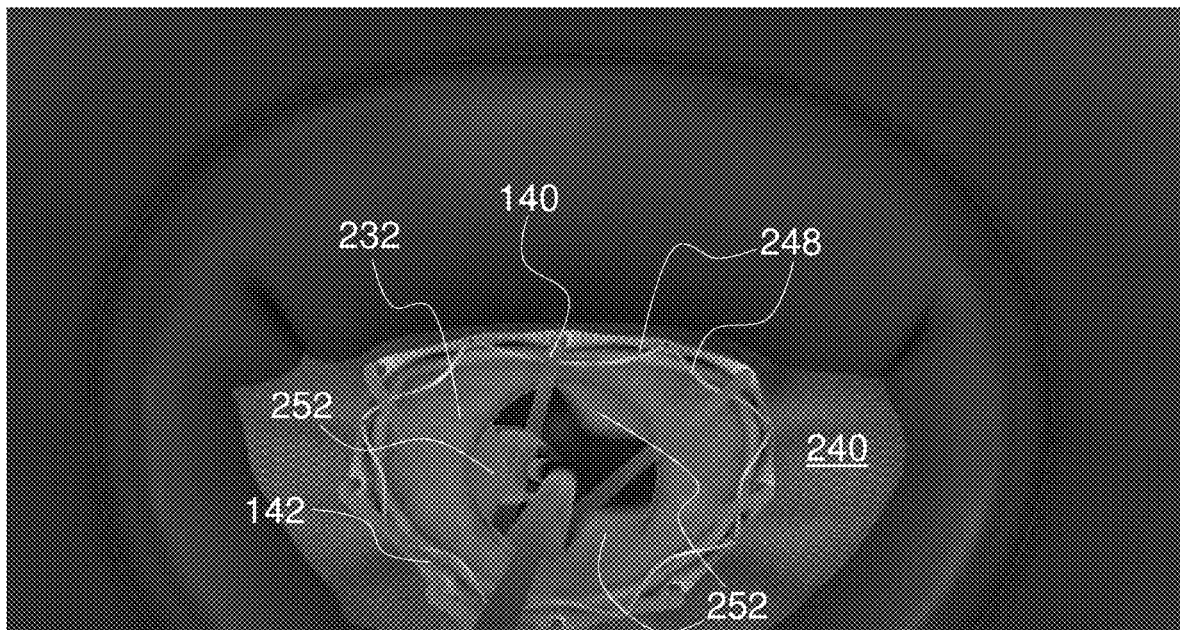
FIG. 30 is a fragmentary, perspective view of the mitral valve replacement implant of FIG. 29 in another forcibly expanded state with the mitral valve open around the mitral valve replacement implant and with the replacement valve of the mitral valve replacement implant partially open.
Figure 31:
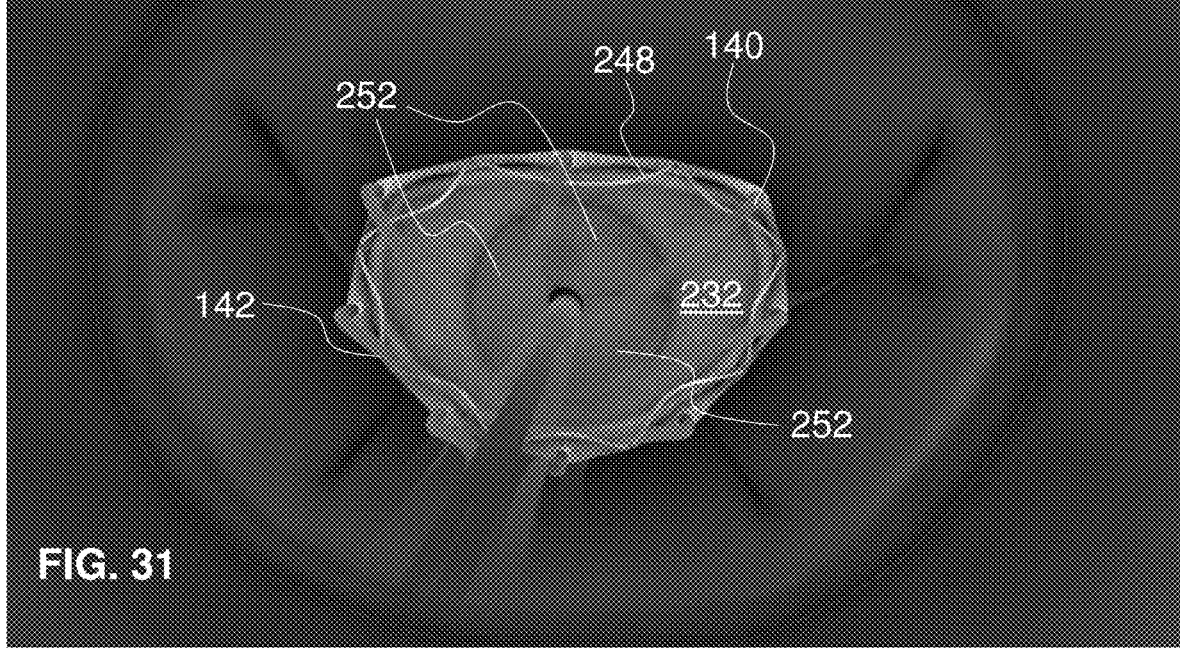
FIG. 31 is a fragmentary, perspective view of the mitral valve replacement implant of FIG. 30 with the mitral valve closed around the mitral valve replacement implant and with the replacement valve of the mitral valve replacement implant closed around the delivery guidewire lumen.

The process for installing the implant 240 from the atrial side is shown in the progression of FIGS. 22 through 35. FIGS. 22 and 23 illustrate the guidewire 10 resting in the left ventricle (installed through the atrium wall) and the diseased mitral valve 12. The guidewire lumen 110 is threaded onto the guidewire 10 and enters the left atrium preceded by the distally connected nosecone 120, resting in the left ventricle. The mitral valve 12 is shown partially closed in FIG. 22 and substantially open in FIG. 23. The implant 200 is compressed within the exterior sheath 130 but the sheath 130 is not illustrated for clarity. In FIG. 24, the outer sheath 130 has been retracted to allow the implant 240 to start self-expanding to its pre-defined, mitral valve D-shape and the implant skirt 240 to start self-expanding within the ventricle to its pre-defined memory shape. In this figure, the mitral valve 12 is substantially open. The adjustable stent lattice 210 is positioned within the mitral valve annulus, as can be seen in FIG. 25, where the mitral valve 12 is closed upon the adjustable stent lattice 210. As the drive wires 150 and disconnect lumens 140 are still connected to the adjustable stent lattice 210, the atrium wall-retaining petals 248 are constrained at the interior sides of the disconnect lumens 140. With the implant 200 centrally disposed within the mitral valve 12, the drive wires 150 can be rotated to actuate the jack screws 220 and, thereby, start expansion of the implant 200. FIG. 26 shows the implant 200 in the state where the implant 200 is fully self-expanded and defines the pre-defined D-shape of the implant (albeit smaller than when implanted), and FIG. 27 shows the implant 200 in a first, forcibly expanded state, with the D-shape larger than the pre-set D-shape. With the mitral valve 12 partially open around the implant 200, the implant skirt 240 can be seen on the ventricle side self-expanded to such an extent that it already occludes the opening of the mitral valve 12, which is due both to the self-expanding features of the implant skirt 240, 242, 244 and to the pressure exerted on the ventricle side of the implant skirt 240 by blood flow. Likewise, this blood flow imparts a force on the replacement valve 250, causing the leaflets 252 to open and allow blood flow through the implant 200. With still further expansion of the implant 200, as shown in FIGS. 28 and 29, expansion of the outer trampoline portion 232 becomes more apparent and the replacement valve 250 begins to function as a valve well before full implantation occurs. This valve functioning is clearly shown in FIGS. 30 and 31, in which, a further expanded state of the implant 200 allows the leaflets 252 of the replacement valve 250 to fully open and fully close (about the guidewire lumen 110).

Figure 32:
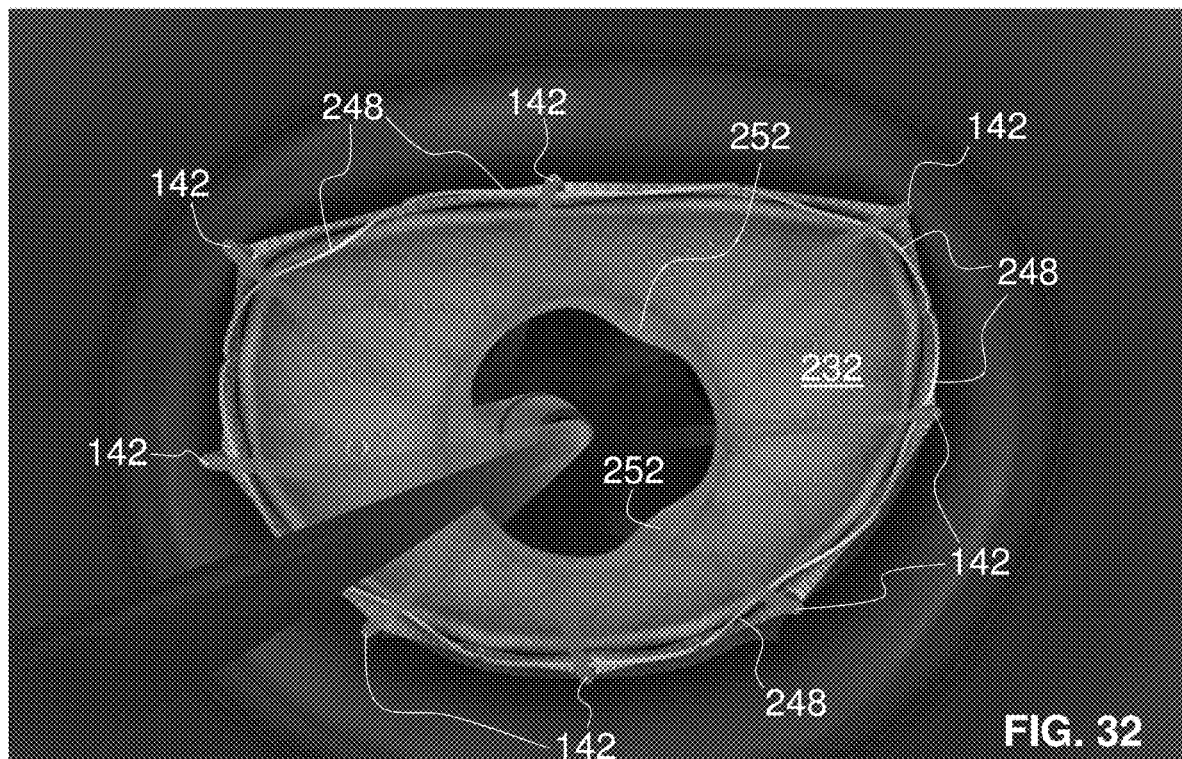
FIG. 32 is a fragmentary, perspective view of the mitral valve replacement implant of FIG. 31 held open by the mitral valve replacement implant in a valve-implanted state and with the replacement valve of the mitral valve replacement implant in an almost fully open state.
Figure 33:
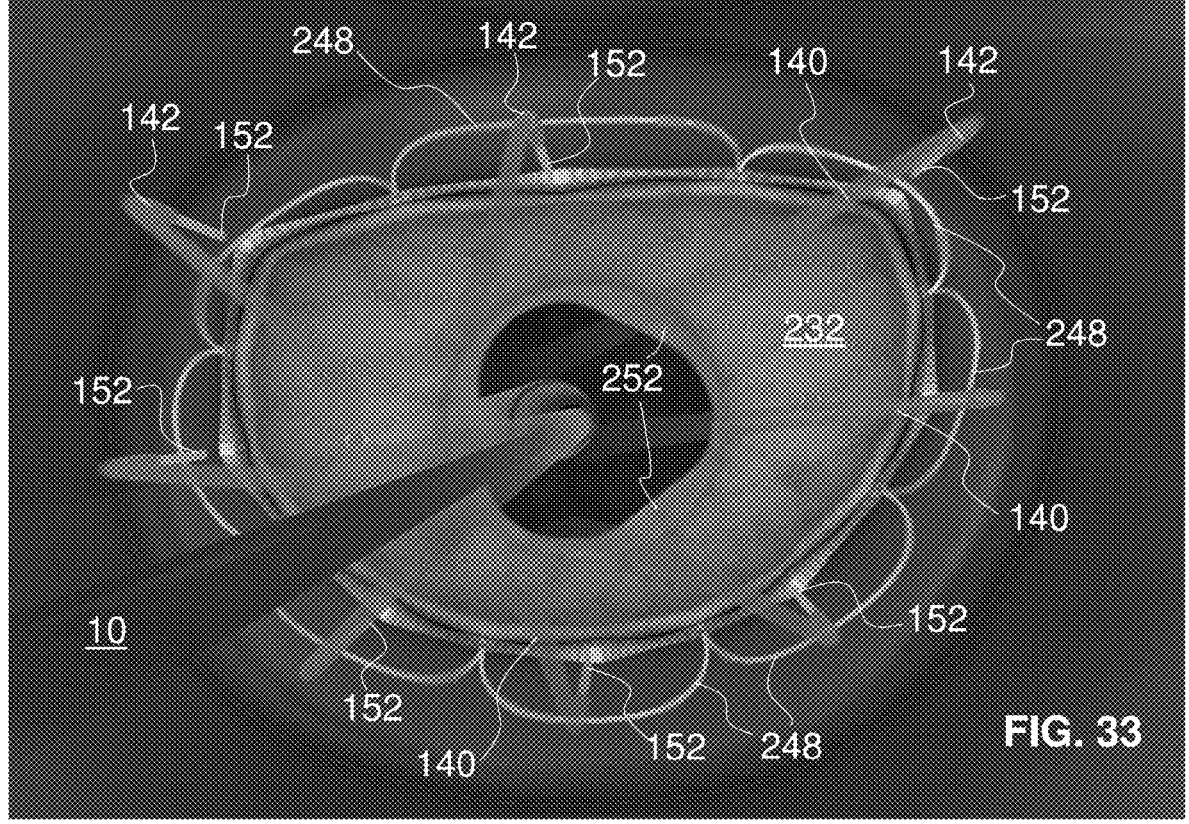
FIG. 33 is a fragmentary, perspective view of the mitral valve replacement implant of FIG. 32 with the mitral valve replacement implant in the valve-implanted state and with the drive wire assembly retracted and disengaged to no longer constrain the atrium retaining petals.

When the implant 200 has been expanded to a state where it is fixed in the diseased mitral valve 12 to hold the diseased mitral valve 12 open, as shown in FIG. 32, the implant 200 is ready to be disengaged from the delivery system 100. At this point, the surgeon can ensure correct implantation because the implant 200 has the ability to reversibly contract and be repositioned if desired. To confirm that the implant 200 is in a desired final state, the surgeon can inject a contrast dye into the ventricle (e.g., through the guidewire lumen 110 or through the guidewire 10, if either is configured to deliver dye, or through a separate contrast device within the ventricle). When the surgeon has determined that no leakage occurs around the implant 200 and that the implant 200 is satisfactorily installed, the surgeon can actuate the disengagement feature of the delivery system 100, which, in this exemplary embodiment, causes the disconnect lumens 140 to retract proximally and, thereby, move the lattice disconnect tubes 142 away from the drive wire connectors 152. FIG. 33 illustrates the disconnect lumens 140 having retracted the lattice disconnect tubes 142 from the drive wires 150 to expose the drive wire connectors 152 (which engage the proximal ends of the jack screws 220 and remain engaged only so long as the lattice disconnect tubes 142 are extended) and, thereby, allow the drive wire connectors 152 to disengage automatically from the jack screws 220. At this point, implantation is final and cannot be reversed without physically removing the implant 200, e.g., through a secondary open surgical procedure. However, such a situation is not necessary when the surgeon has ensured correct placement before disengagement.

Figure 34:
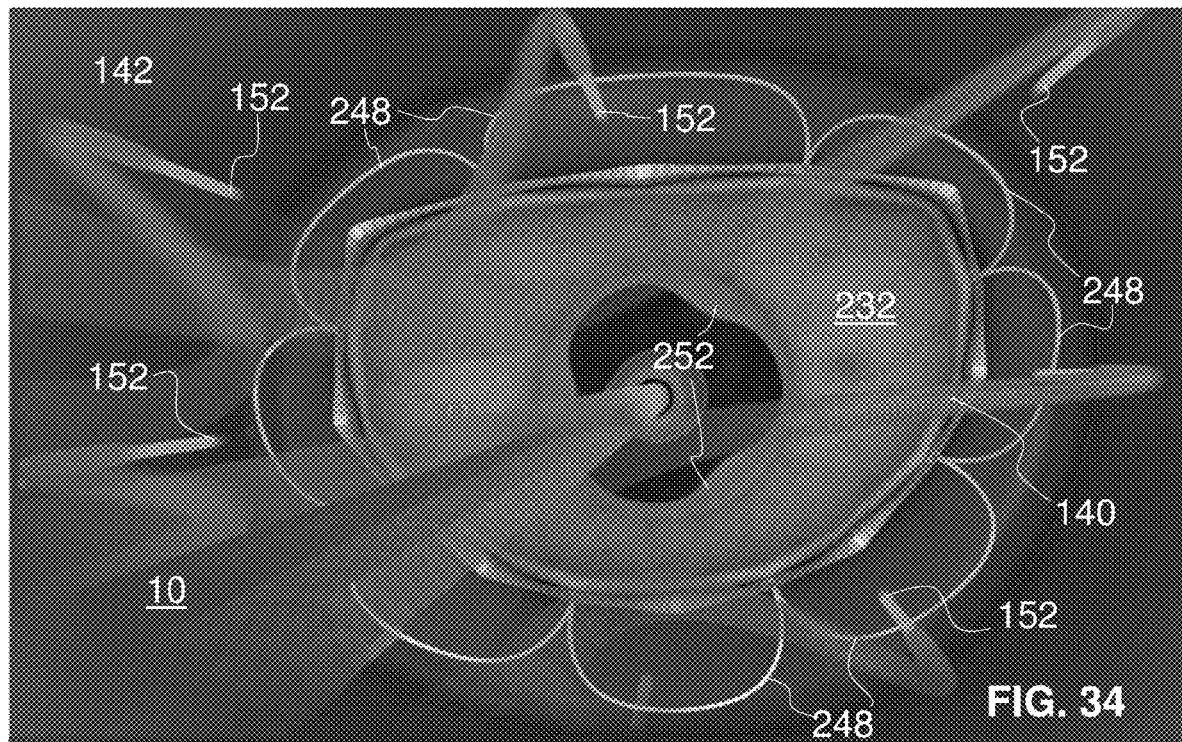
FIG. 34 is a fragmentary, perspective view of the mitral valve replacement implant of FIG. 33 with the mitral valve replacement implant in the valve-implanted state, with the drive wire assembly disengaged and further retracted, and with the atrium retaining petals retained against the wall of the left atrium.
Figure 35:
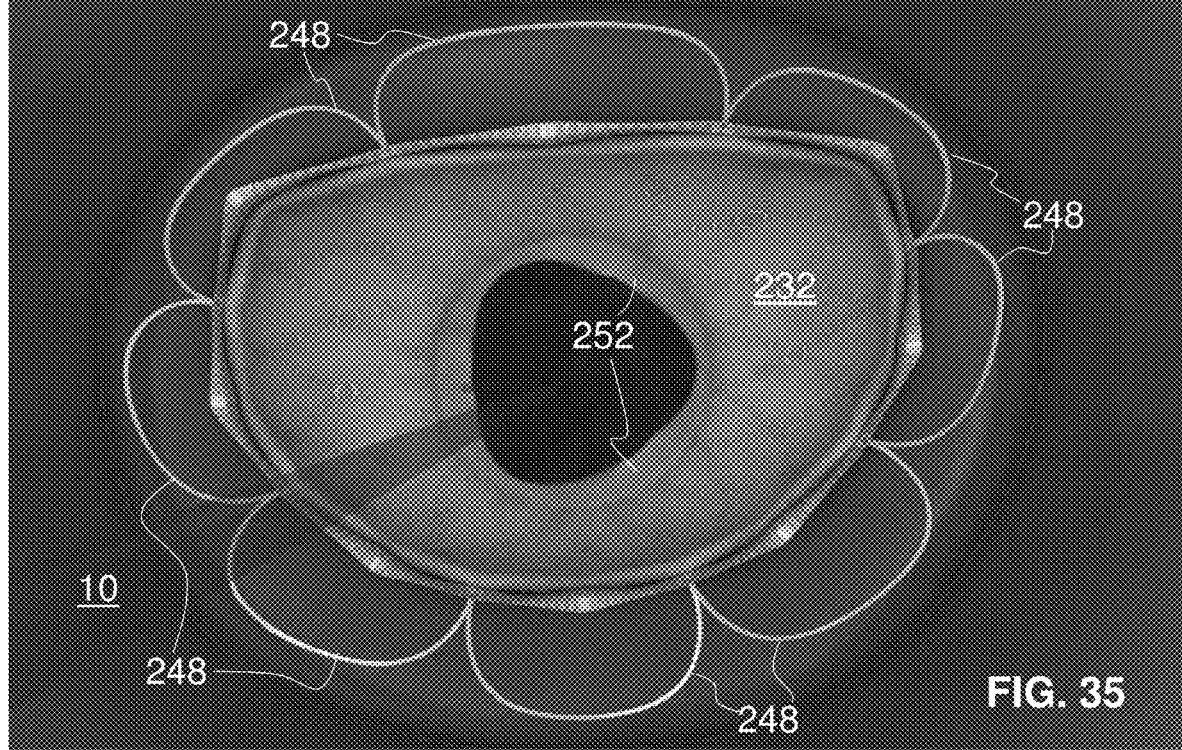
FIG. 35 is a fragmentary, perspective view of the mitral valve replacement implant of FIG. 34 with the mitral valve replacement implant in the valve-implanted state, with the replacement valve of the mitral valve replacement implant in an open state, and with the drive wire assembly completely retracted.
Figure 36:
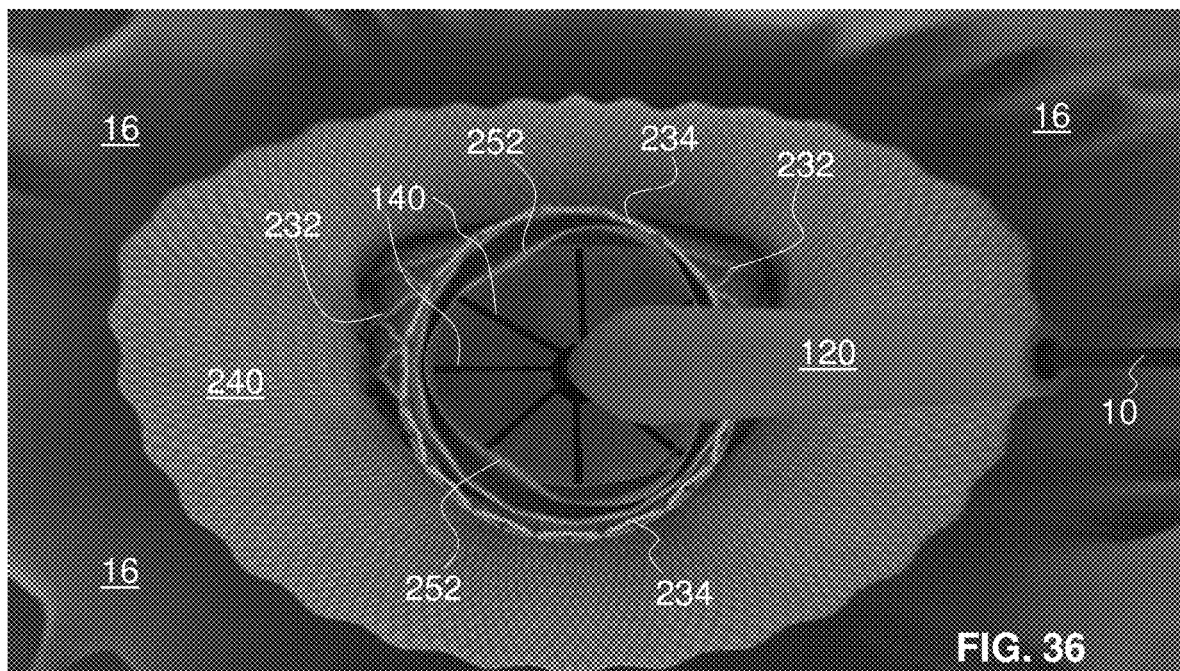
FIG. 36 is a fragmentary, perspective view of the mitral valve replacement implant of FIGS. 9 to 13 in a skirt-and-valve-expanded state approximately equivalent to the view of the mitral valve replacement implant of FIG. 26 and with the replacement valve in a substantially open state.
Figure 37:
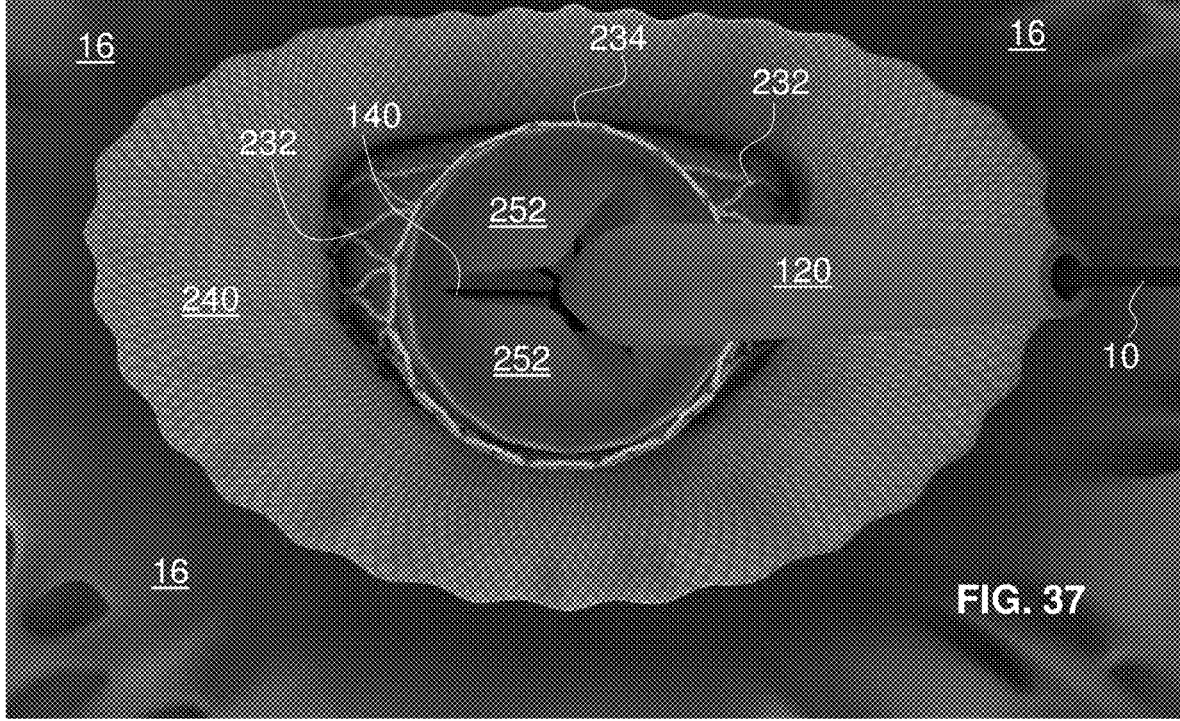
FIG. 37 is a fragmentary, perspective view of the mitral valve replacement implant of FIG. 36 in a skirt-and-valve-expanded state approximately equivalent to the view of the mitral valve replacement implant of FIG. 27 and with the replacement valve in an almost closed state.
Figure 38:
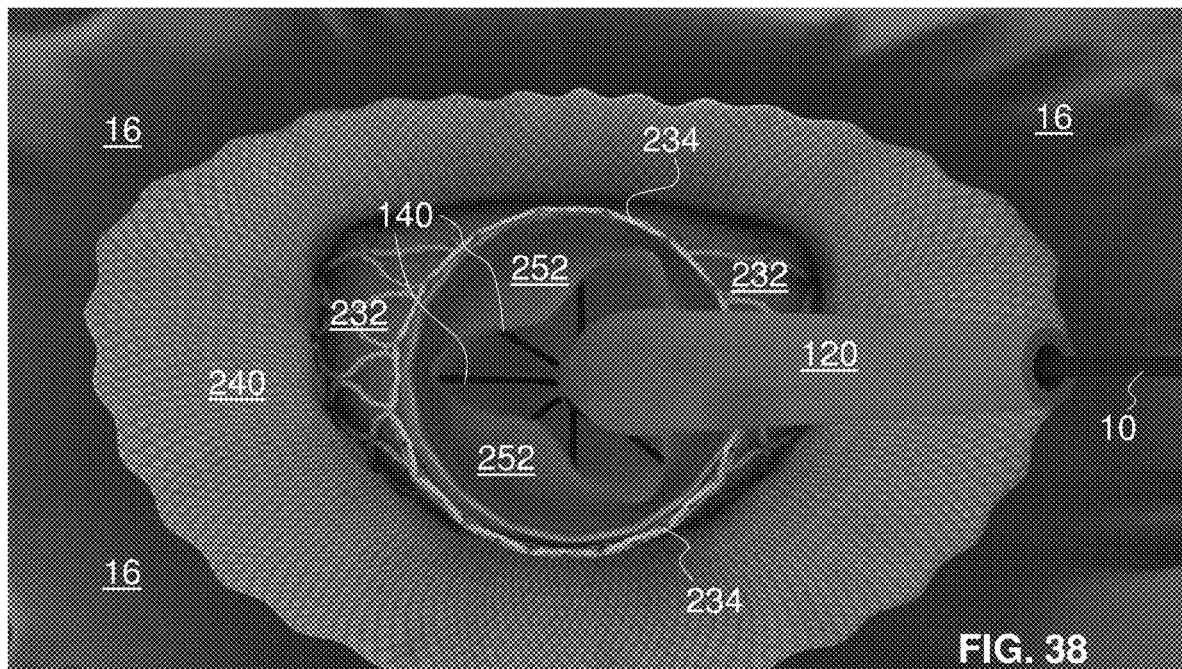
FIG. 38 is a fragmentary, perspective view of the mitral valve replacement implant of FIG. 37 in a skirt-and-valve-expanded state approximately equivalent to the view of the mitral valve replacement implant of FIG. 29 and with the replacement valve in a partially open state.
Figure 39:
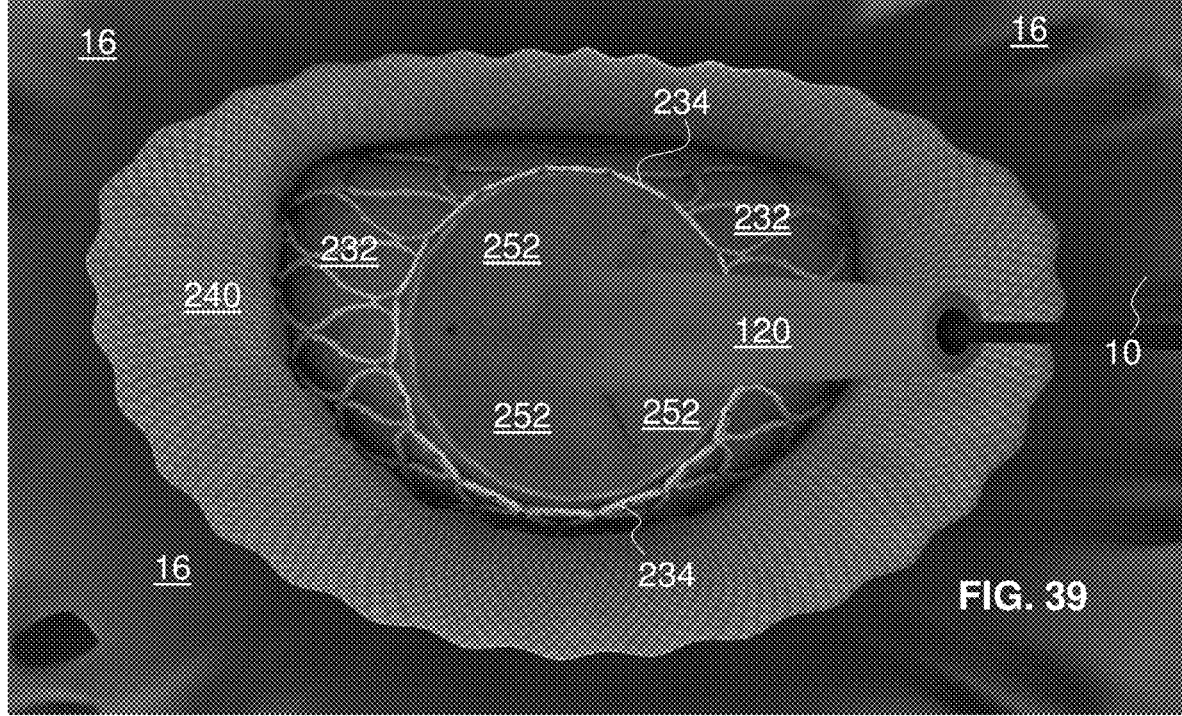
FIG. 39 is a fragmentary, perspective view of the mitral valve replacement implant of FIG. 38 in a skirt-and-valve-expanded state between the views of the mitral valve replacement implant of FIGS. 31 and 32 and with the replacement valve in a substantially closed state.

Now that the disconnect lumens 140 and lattice disconnect tubes 142 no longer restrain the atrium wall-retaining petals 248, the petals 248 can expand outward to their pre-set orientation. FIG. 33 shows the petals 248 in the process of this expansion and FIG. 34 illustrates the petals 248 fully expanded and compressing the ventricle side of the mitral valve 12 in a direction of the implant skirt 240, which, itself, is fully expanded and imparting a compressive force against the atrium side of the mitral valve 12. As the implant process is complete, the disconnect lumens 140 and the drive wires 150 can be removed, which is depicted in FIG. 35.

Figure 40:
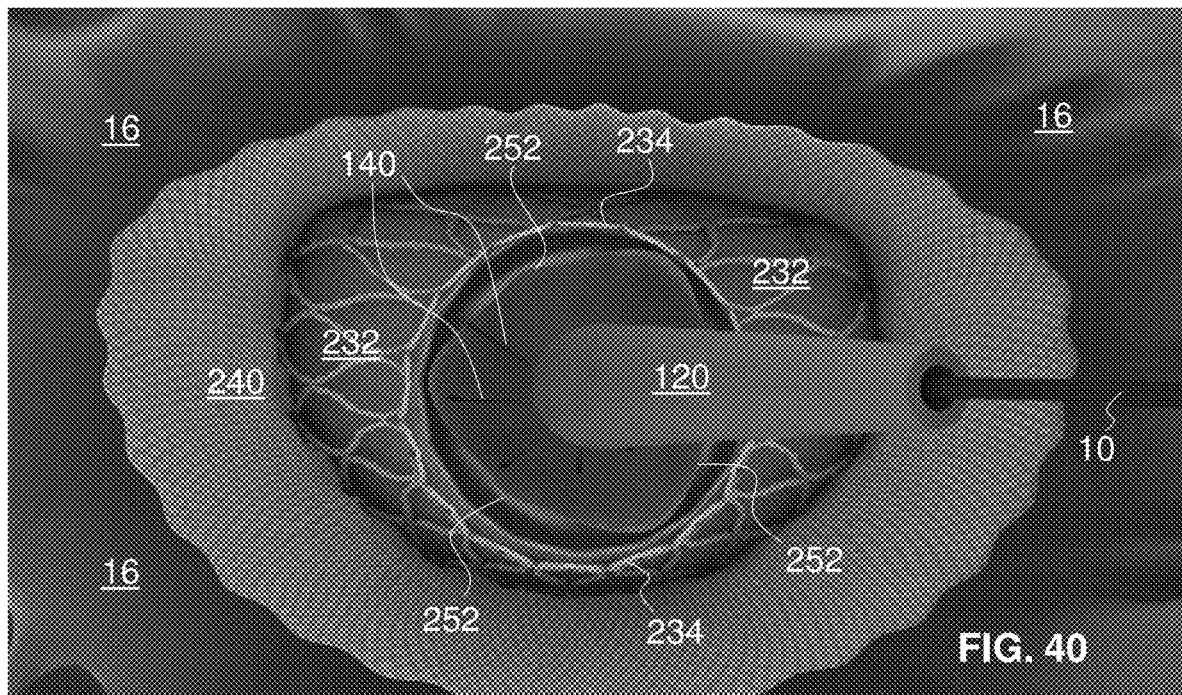
FIG. 40 is a fragmentary, perspective view of the mitral valve replacement implant of FIG. 39 in a valve-implanted state approximately equivalent to the view of the mitral valve replacement implant of FIG. 33 with the replacement valve in a substantially open state and with the drive wires disengaged from the mitral valve replacement implant.
Figure 41:
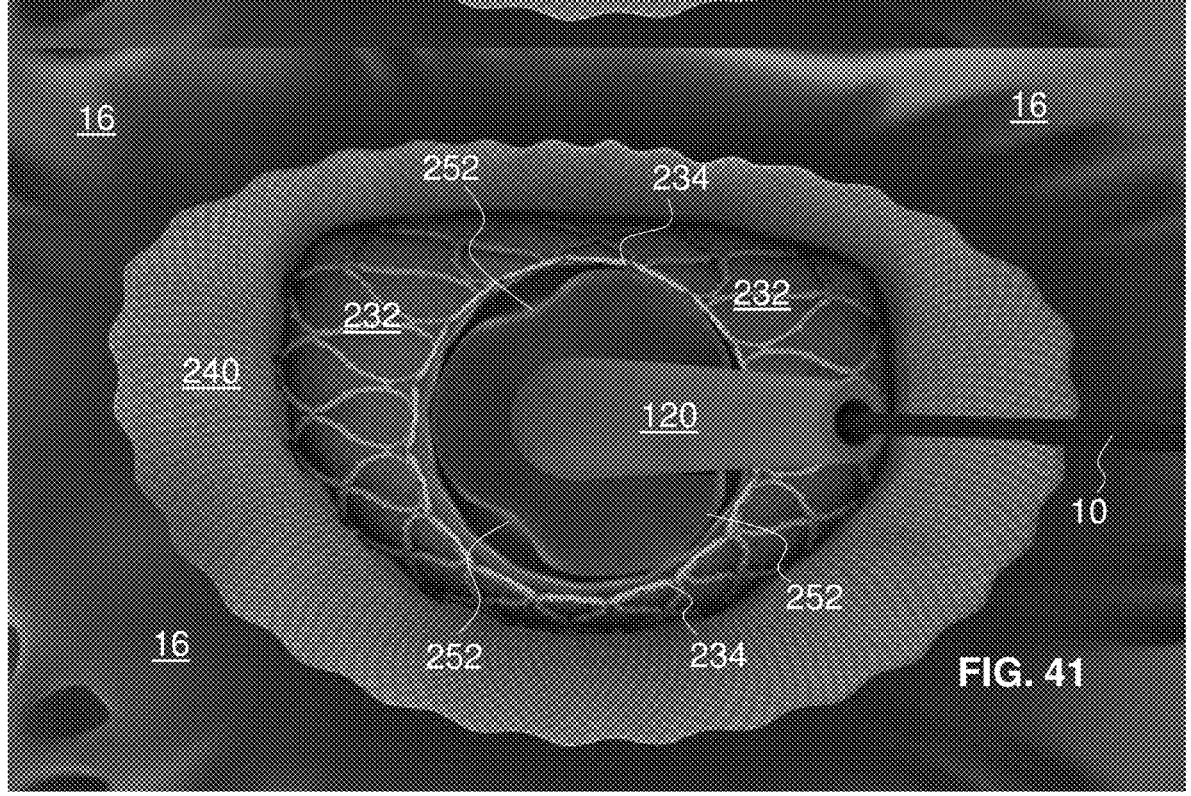
FIG. 41 is a fragmentary, perspective view of the mitral valve replacement implant of FIG. 40 with the drive wires removed and with the nosecone partially retracted.
Figure 42:
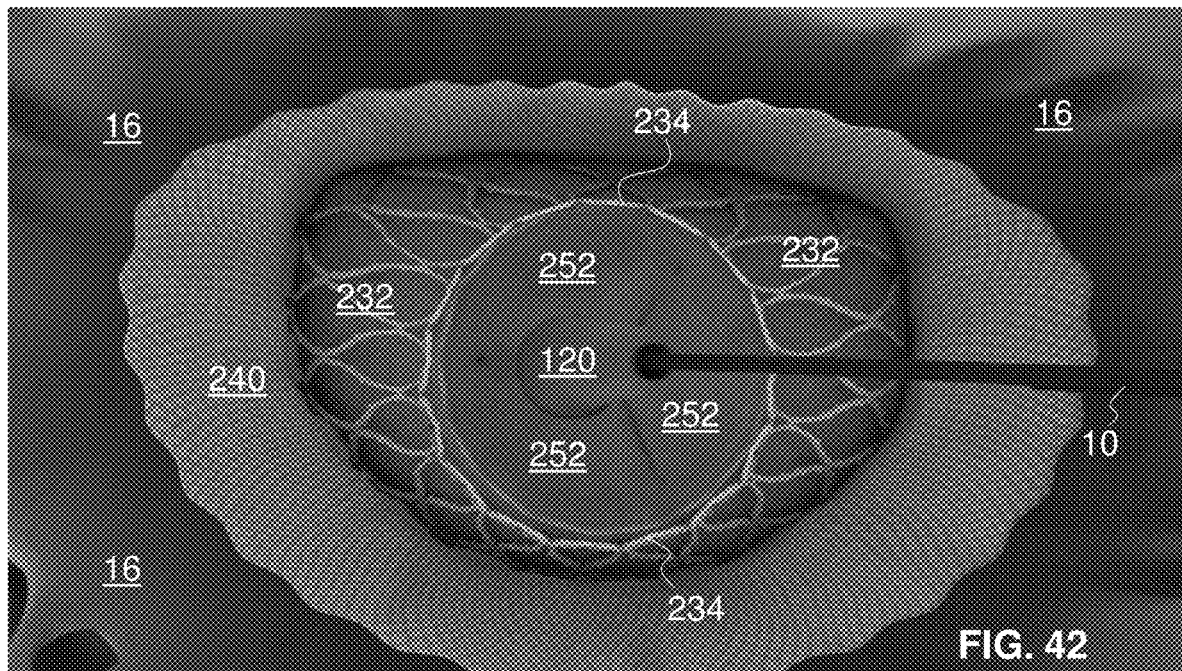
FIG. 42 is a fragmentary, perspective view of the mitral valve replacement implant of FIG. 41 with the nosecone retracted partially through and closed upon by the leaflets of the mitral valve replacement implant.
Figure 43:
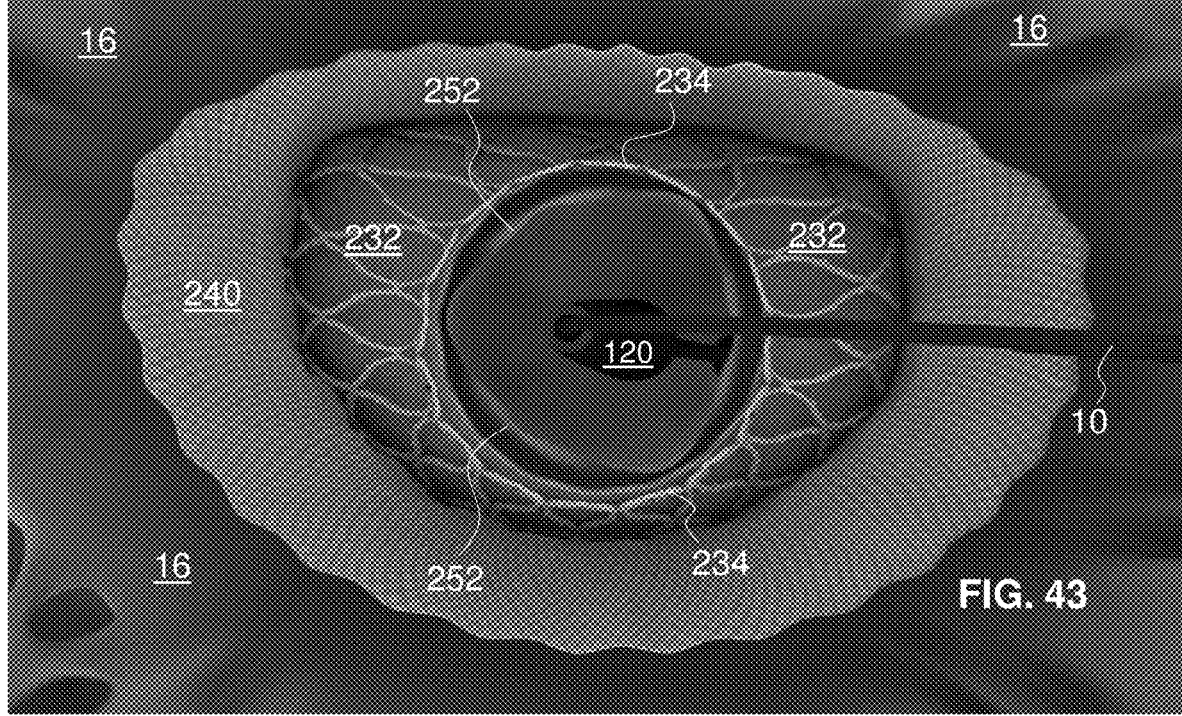
FIG. 43 is a fragmentary, perspective view of the mitral valve replacement implant of FIG. 42 with the nosecone withdrawn from the mitral valve replacement implant and with the replacement valve in a substantially open state.

Above, the implant skirt 240 is described as self-expanding on the ventricle side of the mitral valve 12 starting from the time that it is released from capture within the exterior sheath 130. That expansion is shown from a side of the implant 240 in FIGS. 18 through 21, 24, and 27. FIGS. 36 through 43, however, show the behavior of the implant skirt 240 as the adjustable stent lattice 210 is forcibly expanded from its fully self-expanded state (shown in FIG. 36) until the time of final implantation (shown in FIG. 40). FIGS. 36 through 43 show this behavior viewed from the ventricle side of the implant 200. As the adjustable stent lattice 210 forcibly expands from its self-expanded state in FIG. 36 through the range of expansion in FIGS. 37, 38, and 39, it can be seen that the innermost portions of the implant skirt 240, including the skirt lattice 242 and the outer material 244, move and adjust to accommodate the ever-expanding outer extremities of the outer trampoline portion 232. In contrast, the outermost annulus of the implant skirt 240 remains substantially constant from the time that it is completely released from the sheath 130 until the time when the implant 200 is in its final implant orientation, which is seen in FIG. 40. At this point, the stent control devices (disconnect lumens 140 and drive wires 150) can be disconnected and withdrawn, which is depicted in FIG. 40, these devices 140, 150 being entirely removed from view in FIG. 41 and the nosecone 120 being withdrawn in the progression of FIG. 42 to FIG. 43. These figures illustrated that the replacement valve 250 has functioning leaflets 252 from the time that the adjustable stent lattice 210 is merely allowed to self-expand and continues functioning as a valve all during the time that the implant 200 is being adjusted, expanded, contracted, moved, and/or rotated. These figures also show how the valve trampoline lattice acts as a trampoline. The inner circumferential valve portion 234 remains patent in its circular orientation throughout the time that the outer trampoline portion 232 is being expanded (or contracted).

FIGS. 44 to 47 illustrate an alternative embodiment of an actively controllable stent graft 300. This implant is similar in structure to the implant 200 except the wall-retaining petals 248 and the exterior implant skirt 240 are not present. Although the interior valve assembly also is not present, any valve assembly can be included within the adjustable stent lattice 310 of the implant 300. The implant 300 can be substantially circular or it can be D-shaped. As all other aspects of the implant 300 are similar to the implant 200, all features are not repeated to avoid unnecessary repetition. Likewise, where similar parts are referenced, the reference numeral is increased by 100. What is different with the implant 300 is that the tissue-fixation structures are extendible hooks 342 that are part of or attached to the adjustable stent lattice 310. Such hooks 342 can take the form of the needles 1700 or 2200 or 3070 shown and described in U.S. Patent Publication No. 2013/0046373 to Cartledge et al.

Figure 44:
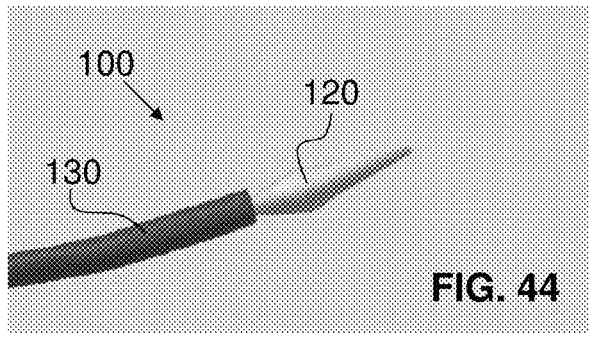
FIG. 44 is a fragmentary, perspective view of an embodiment of an actively controllable delivery or deployment system for an adjustable stent graft.
Figure 45:
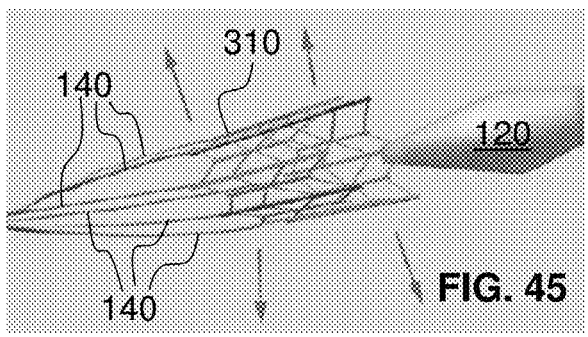
FIG. 45 is a fragmentary, perspective view of another exemplary embodiment of an actively controllable stent graft connected to the delivery system of FIG. 44 in a partially expanded state.
Figure 46:
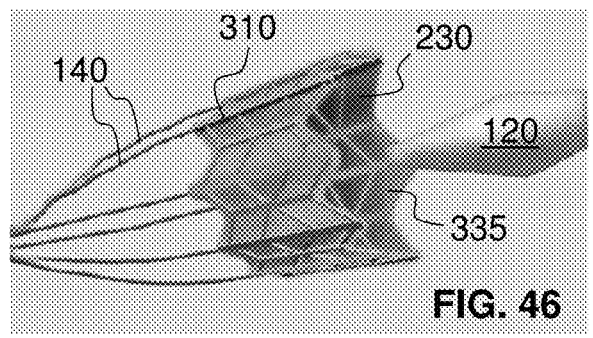
FIG. 46 is a fragmentary, perspective view of the stent graft of FIG. 45 in a fully expanded and ready-to-implant state.
Figure 47:
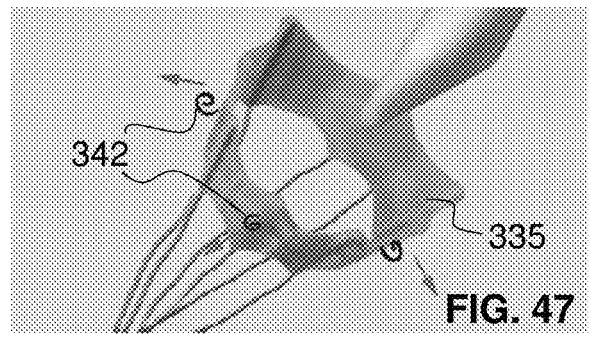
FIG. 47 is a fragmentary, perspective view of the stent graft of FIG. 46 implanted at a target area with tissue-engagement hooks deployed.
Figure 48:
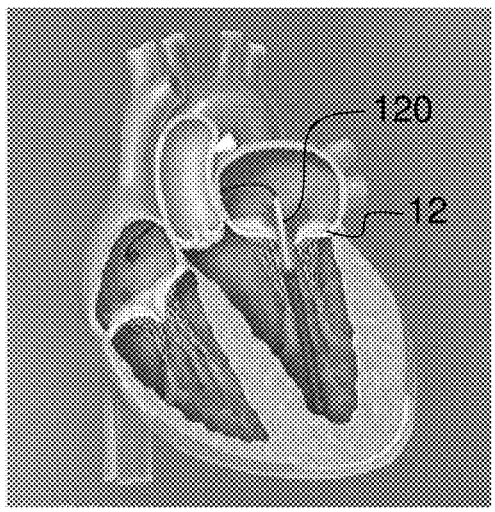
FIG. 48 is a fragmentary, vertically cross-sectional and perspective view of the delivery system of FIG. 44 inserted through the apex of the heart and through the mitral valve annulus into the left atrium.

Deployment of the implant 300 is performed just as implant 200. The delivery system 100 in FIG. 44 is guided along a non-illustrated guidewire to an implant site in the patient. The adjustable stent lattice 310 is allowed to self-expand after removal of the sheath 130 and then is forcibly expanded into the annulus of the implant site to a final implant size, the implant 300 being reversibly expanded and contracted as desired to achieve optimal deployment. This expansion is shown in FIGS. 45 and 46 (the graft material 335 of the implant 300 is not illustrated in FIG. 45). When the implant 300 is in the desired location and orientation and is ready to be released, the extendible hooks 342 are extended out from the sides of the implant 300 to enter into and fixedly connect to the tissue at the implant site. Only three of the hooks 342 are illustrated in FIG. 47 but this number is not to be limiting. In an exemplary embodiment, the number of hooks 342 is equal to the number of disconnect lumens 140, which in the embodiment shown would be six in number.

Figure 49:
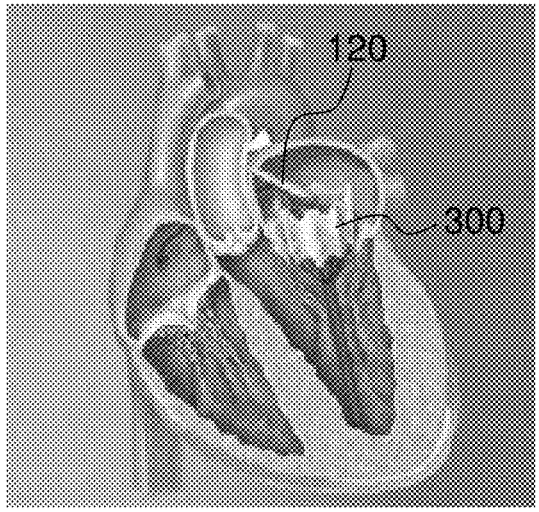
FIG. 49 is a fragmentary, vertically cross-sectional and perspective view of the heart of FIG. 48 with the delivery system deploying the stent graft of FIG. 45 as a replacement mitral valve implant with the implant partially expanded in the mitral valve annulus.
Figure 50:
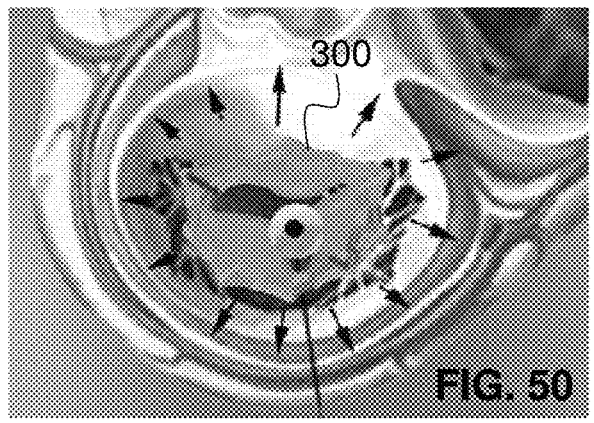
FIG. 50 is a fragmentary, horizontally cross-sectional and perspective view of the heart of FIG. 49.
Figure 51:
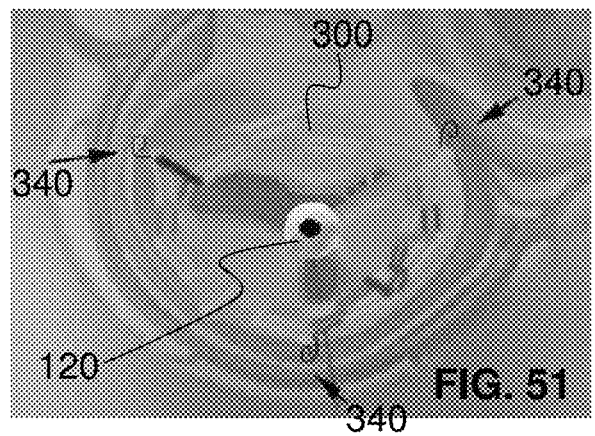
FIG. 51 is a fragmentary, horizontally cross-sectional and perspective view of the heart of FIG. 49 with the delivery system having deployed hooks of the implant into the mitral valve annulus.
Figure 52:
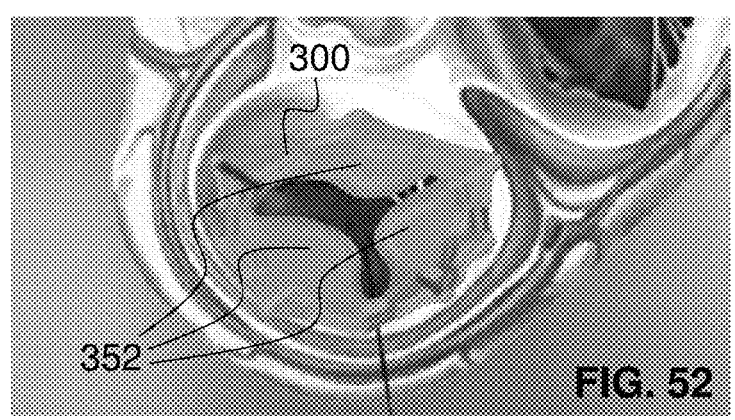
FIG. 52 is a fragmentary, horizontally cross-sectional and perspective view of the heart of FIG. 51 with the delivery system removed from the heart and the implant secured in the mitral valve annulus.

FIGS. 48 to 52 illustrate the process for deploying the implant 300, for example, in the mitral valve of a heart. In contrast to the embodiment of implant 200, which is inserted through the atrium from above the heart, the implant 300 is inserted through a transapical approach. The delivery system 100 is inserted through the apex of the heart up through the left ventricle and through the mitral valve 12 to place the nosecone 120 within the left atrium. The implant 300 is expanded into the mitral valve 12 as shown in FIGS. 49 and 50. When ready to implant, the hooks 342 are extended into the wall of the heart. In FIG. 52, the implant 300 is released from the delivery system 100 and the internal valve leaflets function to valve the blood flow.

FIGS. 53 to 57 illustrate an alternative embodiment of an actively controllable replacement mitral valve implant 400. This implant is similar in structure to the implant 200 except the wall-retaining petals 248 are not present Like implant 200, the implant 400 has an exterior implant skirt 440. The implant 400 can be substantially circular, but it is D-shaped in this mitral valve embodiment. As all other aspects of the implant 400 are similar to the implant 200, all features are not repeated to avoid unnecessary repetition. Likewise, where similar parts are referenced, the reference numeral is increased by 200. What is different with the implant 400 is that the implant skirt 440 is supplemented with tissue-fixation structures in the form of extendible hooks 442 that are part of or attached to the adjustable stent lattice 410. Such hooks 442 can take the form of the needles 1700 or 2200 or 3070 shown and described in U.S. Patent Publication No. 2013/0046373 to Cartledge et al.

Figure 53:
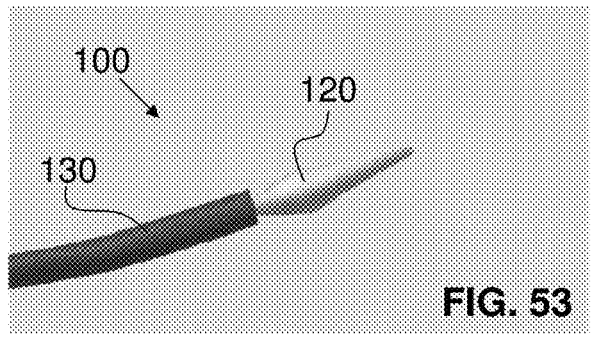
FIG. 53 is a fragmentary, perspective view of the actively controllable delivery system of FIG. 44.
Figure 54:
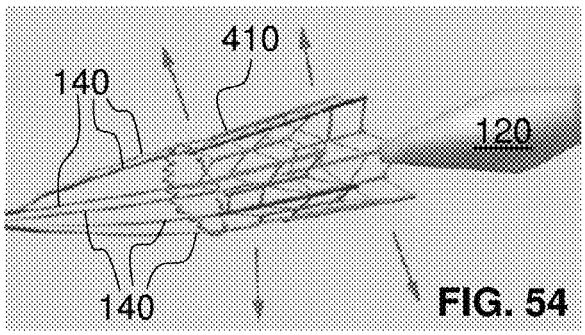
FIG. 54 is a fragmentary, perspective view of another exemplary embodiment of an actively controllable heart valve replacement implant connected to the delivery system of FIG. 53 in a partially expanded state with the inner valve assembly removed.
Figure 55:
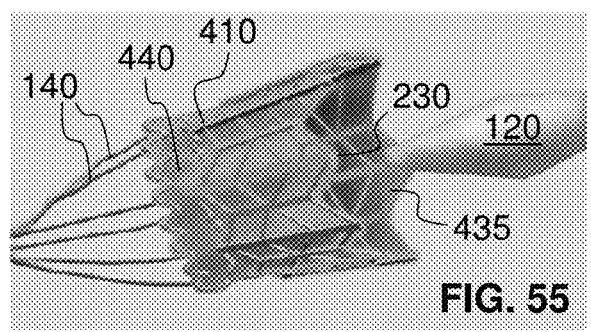
FIG. 55 is a fragmentary, perspective view of the heart valve replacement implant of FIG. 54 in a fully expanded and ready-to-implant state with interior portions of the inner valve assembly removed.
Figure 56:
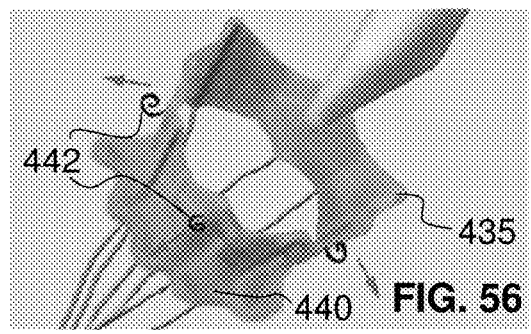
FIG. 56 is a fragmentary, perspective view of the heart valve replacement implant of FIG. 55 implanted at a target area with tissue-engagement hooks and a skirt deployed and with interior portions of the inner valve assembly removed.
Figure 57:
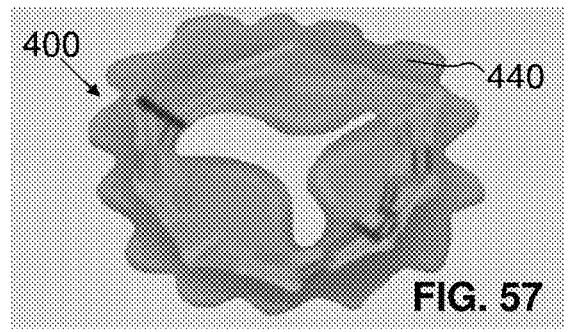
FIG. 57 is a fragmentary, top plan view of the heart valve replacement implant of FIG. 56 implanted at a target area with tissue-engagement hooks and a skirt deployed and with interior portions of the inner valve assembly.

Deployment of the implant 400 is performed just as implant 200. The delivery system 100 in FIG. 53 is guided along a non-illustrated guidewire to an implant site in the patient. The adjustable stent lattice 410 is allowed to self-expand after the sheath is removed and then is forcibly expanded into the annulus of the mitral valve to a final implant size, the implant 400 being reversibly expanded and contracted as desired to achieve optimal deployment. As with implant 200, when the sheath 130 is removed from the compressed implant 400, the implant skirt 440 is allowed to self-expand on the ventricle side of the mitral valve annulus. This expansion is shown in FIGS. 54 and 55 (the graft material 435 of the implant 400 is not illustrated in FIG. 54). When the implant 400 is in the desired location and orientation and is ready to be released, the extendible hooks 442 are extended out from the sides of the implant 400 to enter into and fixedly connect to the tissue at the implant site. Only three of the hooks 442 are illustrated in FIG. 56 but this number is not to be limiting. In an exemplary embodiment, the number of hooks 442 is equal to the number of disconnect lumens 140, which in the embodiment shown would be six in number.

FIGS. 58 to 62 illustrate the process for deploying the implant 400 in the mitral valve annulus of a heart. In contrast to the embodiment of implant 200, which is inserted through the atrium from above the heart, the implant 400 is inserted through a transapical approach. The delivery system 100 is inserted through the apex of the heart up through the left ventricle and through the mitral valve 12 to place the nosecone 120 within the left atrium. The implant 400 is expanded into the mitral valve 12 as shown in FIGS. 59 and 60. When ready to implant, the hooks 442 are extended into the wall of the heart. In FIG. 62, the implant 400 is released from the delivery system 100 and the internal valve leaflets 452 function to valve the blood flow.

FIGS. 63 to 67 illustrate an alternative embodiment of an actively controllable replacement mitral valve implant 500. This implant is similar in structure to the implant 200 except the wall-retaining petals 248 are not present Like implant 200, the implant 500 has an exterior implant skirt 540. The implant 500 can be substantially circular, but it is D-shaped in this mitral valve embodiment. As all other aspects of the implant 500 are similar to the implant 200, all features are not repeated to avoid unnecessary repetition. Likewise, where similar parts are referenced, the reference numeral is increased by 300. What is different with the implant 500 is that the implant skirt 540 is supplemented with tissue-fixation structures in the form of extendible hooks 542 that are part of or attached to the adjustable stent lattice 410. The self-expanding valve trampoline lattice 530 is also present. The hooks 542 can take the form of the needles 1700 or 2200 or 3070 shown and described in U.S. Patent Publication No. 2013/0046373 to Cartledge et al.

Figure 63:
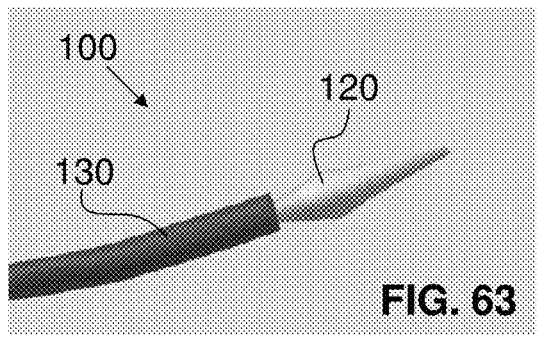
FIG. 63 is a fragmentary, perspective view of the actively controllable delivery system of FIG. 44.
Figure 64:
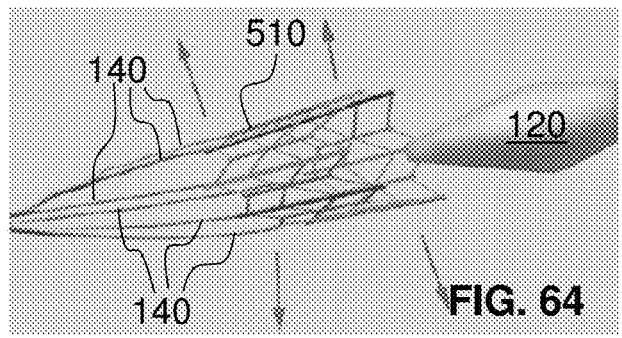
FIG. 64 is a fragmentary, perspective view of another exemplary embodiment of an actively controllable heart valve replacement implant connected to the delivery system of FIG. 63 in a partially expanded state with the inner valve assembly removed.
Figure 65:
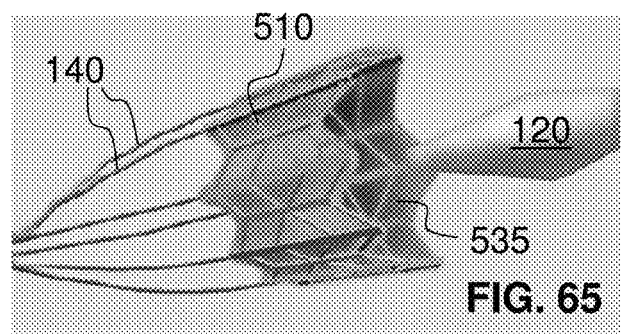
FIG. 65 is a fragmentary, perspective view of the heart valve replacement implant of FIG. 64 in a fully expanded and ready-to-implant state with interior portions of the inner valve assembly removed.
Figure 66:
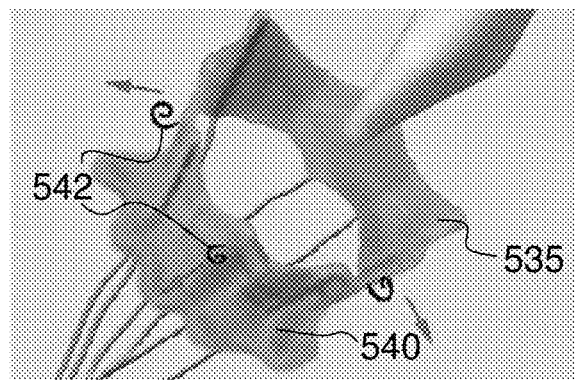
FIG. 66 is a fragmentary, perspective view of the heart valve replacement implant of FIG. 65 implanted at a target area with tissue-engagement hooks and an upstream skirt deployed and with interior portions of the inner valve assembly removed.
Figure 67:
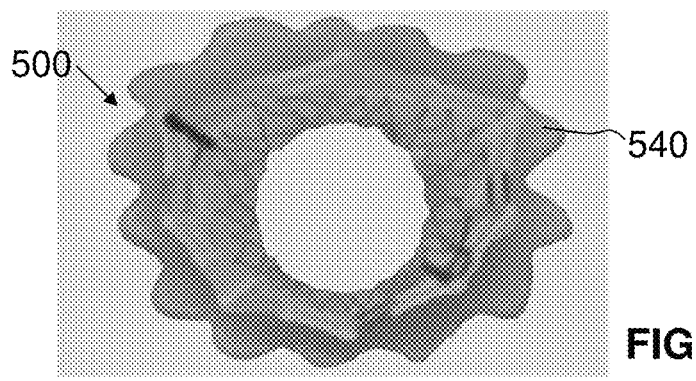
FIG. 67 is a fragmentary, top plan view of the heart valve replacement implant of FIG. 66 implanted at a target area with tissue-engagement hooks, an upstream skirt, and a trampoline valve deployed and with valve leaflets removed.

Deployment of the implant 500 is performed just as implant 200. The delivery system 100 in FIG. 63 is guided along a non-illustrated guidewire to an implant site in the patient. The adjustable stent lattice 510 is allowed to self-expand after the sheath is removed and then is forcibly expanded into the annulus of the mitral valve to a final implant size, the implant 500 being reversibly expanded and contracted as desired to achieve optimal deployment. As with implant 200, when the sheath 130 is removed from the compressed implant 500, the implant skirt 540 is allowed to self-expand on the ventricle side of the mitral valve annulus. This expansion is shown in FIGS. 64 and 65 (the graft material 535 of the implant 500 is not illustrated in FIG. 64). When the implant 600 is in the desired location and orientation and is ready to be released, the extendible hooks 542 are extended out from the sides of the implant 500 to enter into and fixedly connect to the tissue at the implant site. Only three of the hooks 542 are illustrated in FIG. 66 but this number is not to be limiting. In an exemplary embodiment, the number of hooks 542 is equal to the number of disconnect lumens 140, which in the embodiment shown would be six in number.

FIGS. 68 to 72 illustrate the process for deploying the implant 500 in the mitral valve annulus of a heart. In contrast to the embodiment of implant 200, which is inserted through the atrium from above the heart, the implant 500 is inserted through a transapical approach. The delivery system 100 is inserted through the apex of the heart up through the left ventricle and through the mitral valve 12 to place the nosecone 120 within the left atrium. The implant 500 is expanded into the mitral valve 12 as shown in FIGS. 69 and 70. When ready to implant, the hooks 542 are extended into the wall of the heart. In FIG. 72, the implant 500 is released from the delivery system 100 and the internal, non-illustrated valve leaflets function to valve the blood flow.

Figure 73:
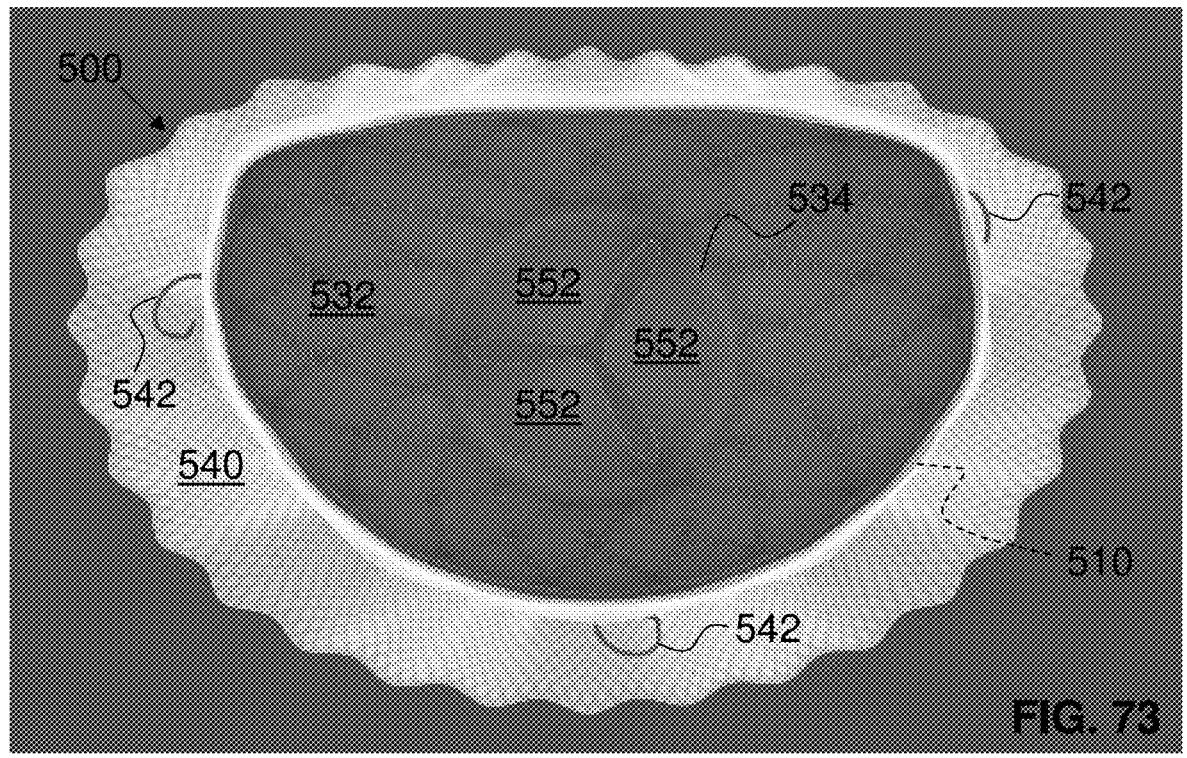
FIG. 73 is an atrium-side elevational view of the mitral valve replacement implant of FIGS. 64 to 67 and 69 to 72 with the valve leaflets in an almost-closed state and with hook fasteners extended radially outward.
Figure 74:
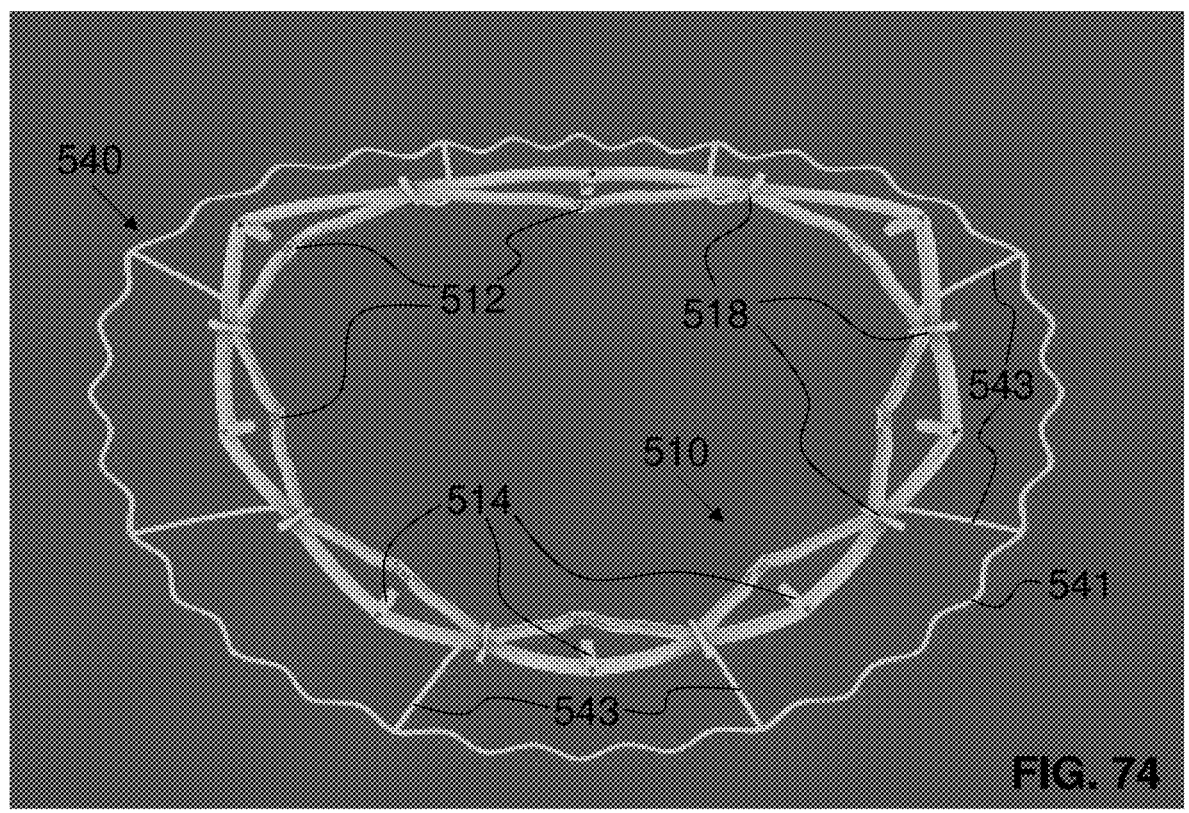
FIG. 74 is a top plan view of an implant skirt frame and an adjustable stent lattice of the mitral valve replacement implant of FIG. 73.
Figure 75:
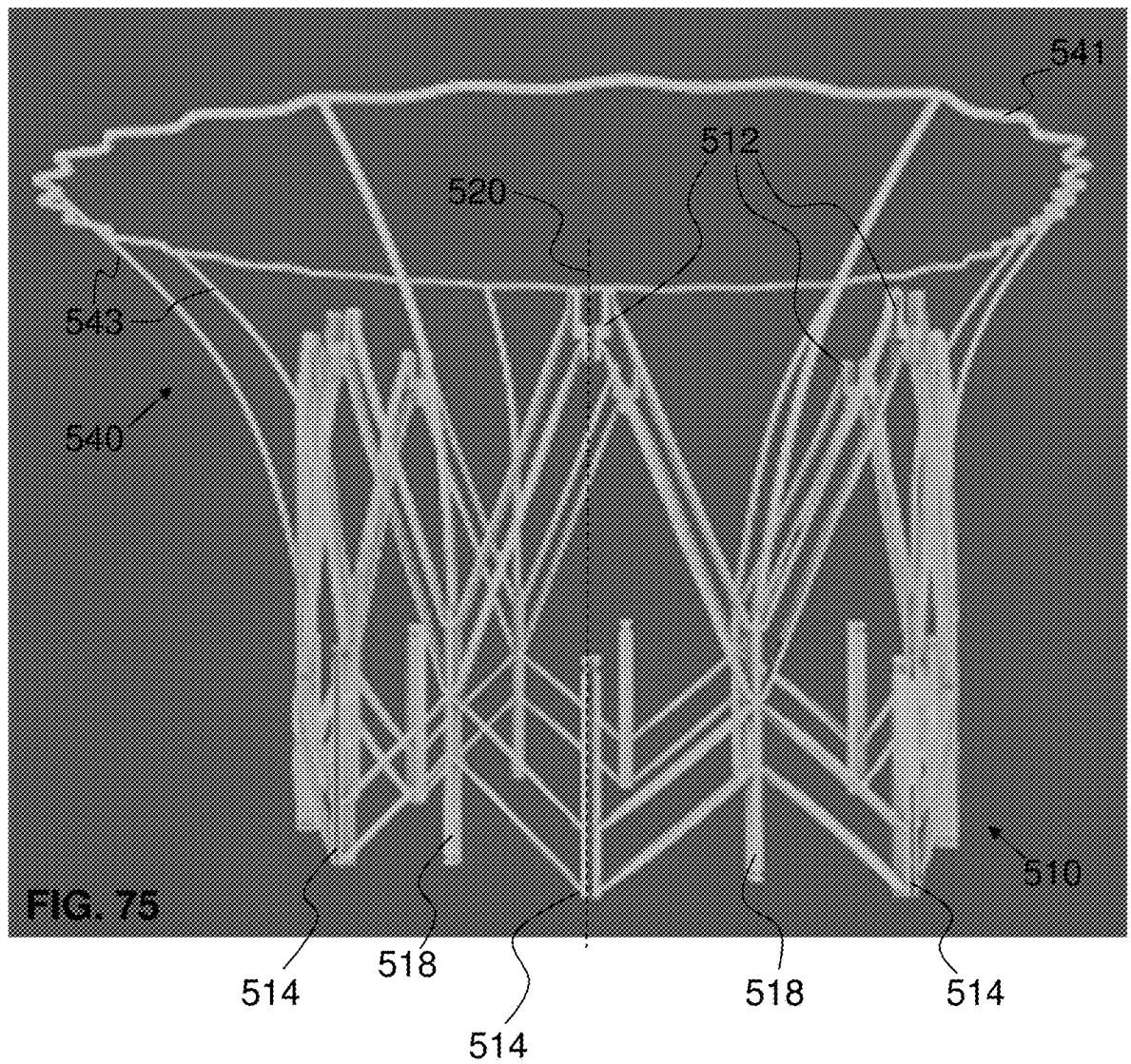
FIG. 75 is a perspective view from a side of the skirt frame and adjustable stent lattice of FIG. 74.

FIG. 73 illustrates an exemplary embodiment of the implant 500, viewed from the atrium side thereof with the expandable outer trampoline portion 532 deployed and the leaflets 552 of the inner circumferential valve portion 534 in an almost closed state. FIGS. 74 and 75 show the skeleton of the implant 500 with the outer material and trampoline valve removed. The implant skirt 540 comprises two parts, an outer circumferential ring 541 and a set of ring-connecting struts 543, which connect the ring 541 to the adjustable stent lattice 510. Both the ring 541 and the struts 543 are made of a material that is self-expanding and having a desired, pre-set shape (such as heat-set nitinol, for example). The struts 543 can be integral with the ring 541 and/or the adjustable stent lattice 510 or connected thereto. The various parts of the adjustable stent lattice 510 are best viewed in FIG. 75. The adjustable stent lattice 510 comprises sets of jack screw connectors, each set having a proximal jack strut 512 and a distal jack strut 514. Arms 516 connect each of the proximal and distal jack struts 512, 514 to an intermediate strut 518. Jack screws 520, which are non-illustrated for clarity but one is depicted as a dashed line in FIG. 75, connect to the proximal and distal jack struts 512, 514 so that, when the jack screw 520 is turned in one direction, the proximal and distal jack struts 512, 514 separate from one another and, when the jack screw 520 is turned in the other opposite direction, the proximal and distal jack struts 512, 514 move towards one another. This configuration can be achieved in various ways. One exemplary embodiment fixes a non-illustrated threaded nut within the distal jack strut 514 to allow the jack screw 520 to threadedly enter into and retract from a smooth-bored hollow in the distal jack strut 514 and places a rotationally free but longitudinally fixed connection of the jack screw 520 at the proximal jack strut 512. In this manner, when the jack screw 520 is rotated in a strut-approaching direction, the distal end of the jack screw 520 moves into the internal non-threaded bore of the distal jack strut 514 (via the connection with threads of the nut) and the proximal end of the jack screw 520 remains longitudinally fixed at the proximal jack strut 512 but is allowed to rotate freely therein. As set forth above, the proximal end of the jack screw 520 has a connector part that is removably connected to a drive wire connector 150 of a drive wire 150 so that, when the drive wire connector 150 is caused to rotate, the jack screw 520 rotates correspondingly. This connection is maintained in any of the exemplary embodiments when the lattice disconnect tubes surround both the proximal end of the jack screw (referred to as a driving connector) and the drive wire connector 150. One way to form the removable connection is through a form fit, such as two cylinders having a mirrored handshake keying that only remains connected when a hollow cylindrical shroud encircles that connection. A form-locking or form-fitting connection is one that connects two elements together due to the shape of the elements themselves, as opposed to a force-locking connection, which locks the elements together by force external to the elements.

With such a configuration, rotation of the many jack screws 520 in the strut-approaching direction causes the proximal and distal jack struts 512, 514 to move towards one another and, thereby, push the intermediate struts 518 (which are disposed parallel to the jack screws 520) away from the jack screw 520 in a direction along the circumferential extent of the annulus of the adjustable stent lattice 510. This relative movement of the intermediate strut 518 and the jack screw assemblies causes expansion of the adjustable stent lattice 510 when the proximal and distal jack struts 512, 514 move towards one another and causes contraction of the adjustable stent lattice 510 when the proximal and distal jack struts 512, 514 move away from one another. Ideally, all of the jack screws 520 are rotated at the same speed to but such equal movement is not to be considered limiting.

In the exemplary embodiment of the adjustable stent lattice 510 shown, there are eight pairs of jack struts 512, 514 and eight intermediate struts 518. This number is merely exemplary and there can be, for example, only six of each or any other number desired including any number from 1 to 10. Connecting the pairs of jack struts 512, 514 and the intermediate struts 518 are the laterally extending arms 516. As the adjustable stent lattice 510 is either contracted or expanded, the arms 516 each flex at their two endpoints, one at a respective intermediate strut 518 and the other at a respective one of a pair of jack struts 512, 514. As can be seen from the configuration shown in FIG. 75, when the adjustable stent lattice 510 is contracted (e.g., for installation into the delivery sheath 130), the arms 516 move towards a longitudinal orientation (parallel to the jack screws and to the central axis of the lattice 510. Conversely, when the adjustable stent lattice 510 is expanded (e.g., for implantation), the arms 516 angle away from the respective intermediate strut 518 and one of the pair of jack struts 512, 514 in a circumferential orientation (perpendicular to the jack screws).

While this detailed description of the parts of the adjustable stent lattice 510 is present herein with respect to implant 500, it is equally applicable to the each of the alternative implant embodiments described herein.

As stated above, the structures forming the various exemplary embodiments for heart valves are not limited to only a single valve or a single exterior shape. The features can be extended to alternative configurations.

Figure 76:
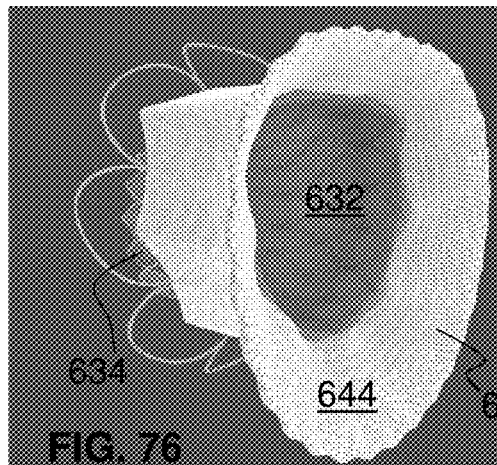
FIG. 76 is an atrium-side perspective view of another exemplary embodiment of an actively controllable, mitral valve replacement implant with an implant skirt, wall-retaining petals, and an internal valve trampoline.
Figure 77:
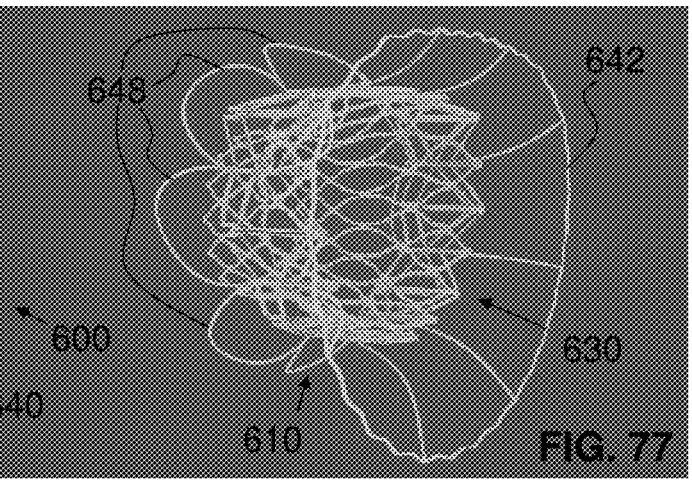
FIG. 77 is an atrium-side perspective view of an implant skirt frame, wall-retaining petals, a valve trampoline lattice, and an adjustable stent lattice of the mitral valve replacement implant of FIG. 76.
Figure 78:
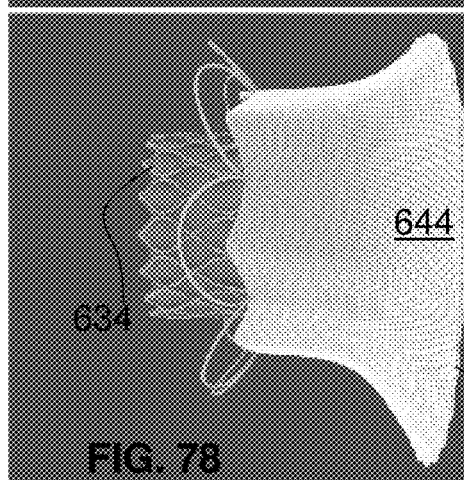
FIG. 78 is a substantially side elevational view of the mitral valve replacement implant of FIG. 76.
Figure 79:
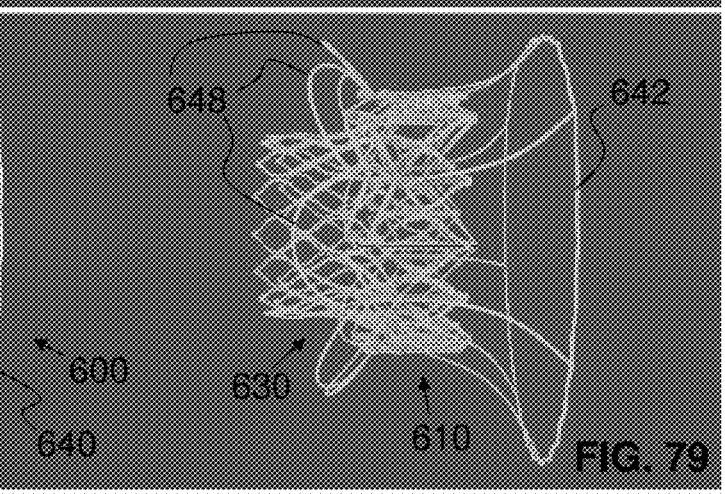
FIG. 79 is a substantially side elevational view of the implant skirt frame, the wall-retaining petals, the valve trampoline lattice, and the adjustable stent lattice of the mitral valve replacement implant of FIG. 76.
Figure 80:
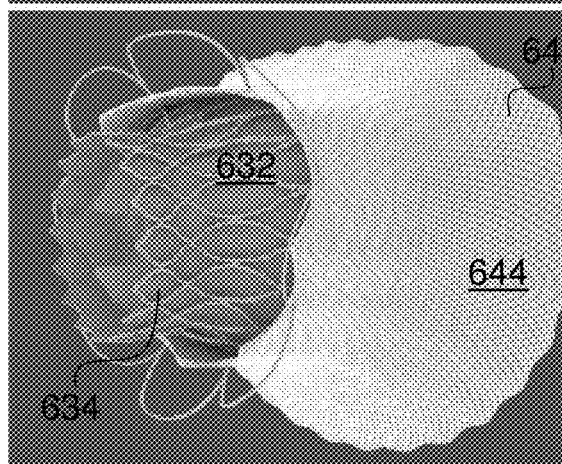
FIG. 80 is a ventricle-side perspective view of the mitral valve replacement implant of FIG. 76.
Figure 81:
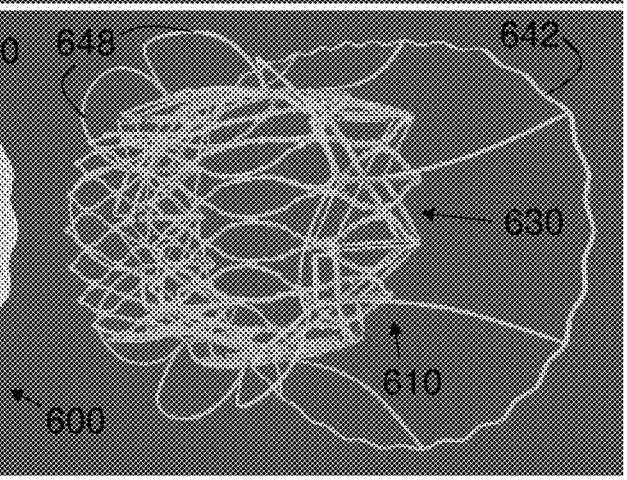
FIG. 81 is a ventricle-side perspective view of the implant skirt frame, the wall-retaining petals, the valve trampoline lattice, and the adjustable stent lattice of the mitral valve replacement implant of FIG. 76.

A first alternative configuration of a mitral valve replacement implant 600 is shown in FIGS. 78 to 81. In the embodiment of FIGS. 2 to 13, the mitral valve replacement implant 200 had the trampoline lattice 230 projecting through the implant skirt 240 on the ventricle side of the implant 200. The exemplary embodiment of the mitral valve replacement implant 600 in FIGS. 78 to 81 provides the trampoline lattice 630 with the inner circumferential valve portion 634 on the opposing side and projecting out from the side of the implant 600 with the wall-retaining petals 648. The expandable outer trampoline portion 632 is visible in FIG. 76. The framework of the implant 600 is shown without the external coverings and valve material in FIGS. 77, 79, and 81 to expose the adjustable stent lattice 610, the skirt lattice 642, and the wall-retaining petals 648.

A second alternative configuration of a circular valve replacement implant 600 is shown in FIGS. 82 to 87. In the embodiment of FIGS. 78 to 81, the implant 600 had an overall D-shape and the wall-retaining petals 648 were uncovered. The exemplary embodiment of the valve replacement implant 700 in FIGS. 82 to 87 likewise provides the trampoline lattice 730 with the inner circumferential valve portion 734 on the side opposite the implant skirt 740 projecting out from the side of the implant 700 with the wall-retaining petals 748 but is circular in its overall shape. Both the expandable outer trampoline portion 732 and the inner circumferential valve portion 734 are visible in FIG. 82. As can be seen, the material 744 of the implant skirt 740 also covers the wall-retaining petals 748. The framework of the implant 700 is shown without the external coverings and valve material in FIGS. 83, 85, and 87 to expose the adjustable stent lattice 710, the skirt lattice 742, and the wall-retaining petals 748. Because the disconnect lumens 140 and the drive wires 150 connect from the side of the wall-retaining petals 748, the nosecone 120 is on the side of the implant skirt 740.

A third alternative configuration of a circular valve replacement implant 800 is shown in FIGS. 88 to 93. In the embodiment of FIGS. 82 to 87, the implant 700 had an overall circular shape and the wall-retaining petals 748 were covered. Like the implant 700, the implant 800 is circular in its overall shape. In contrast to the implant 700, however, the exemplary embodiment of the valve replacement implant 800 in FIGS. 88 to 93 has the trampoline lattice 830 with the inner circumferential valve portion 834 on the side opposite the wall-retaining petals 848 to project out from the side of the implant 800 having the implant skirt 840. The expandable outer trampoline portion 832 is visible from the interior of the implant 800 in FIG. 88 and the inner circumferential valve portion 834 is visible in both FIGS. 90 and 92. As can be seen, the material 844 of the implant skirt 840 does not cover the wall-retaining petals 848, but it does project into the central orifices defined by each petal 848 in order to cover the proximal jack strut 812. The framework of the implant 800 is shown without the external coverings and valve material in FIGS. 89, 91, and 93 to expose the adjustable stent lattice 810, the skirt lattice 842, and the wall-retaining petals 848. Because the disconnect lumens 140 and the drive wires 150 connect from the side of the wall-retaining petals 848, the nosecone 120 is on the side of the implant skirt 840.

Figure 94:
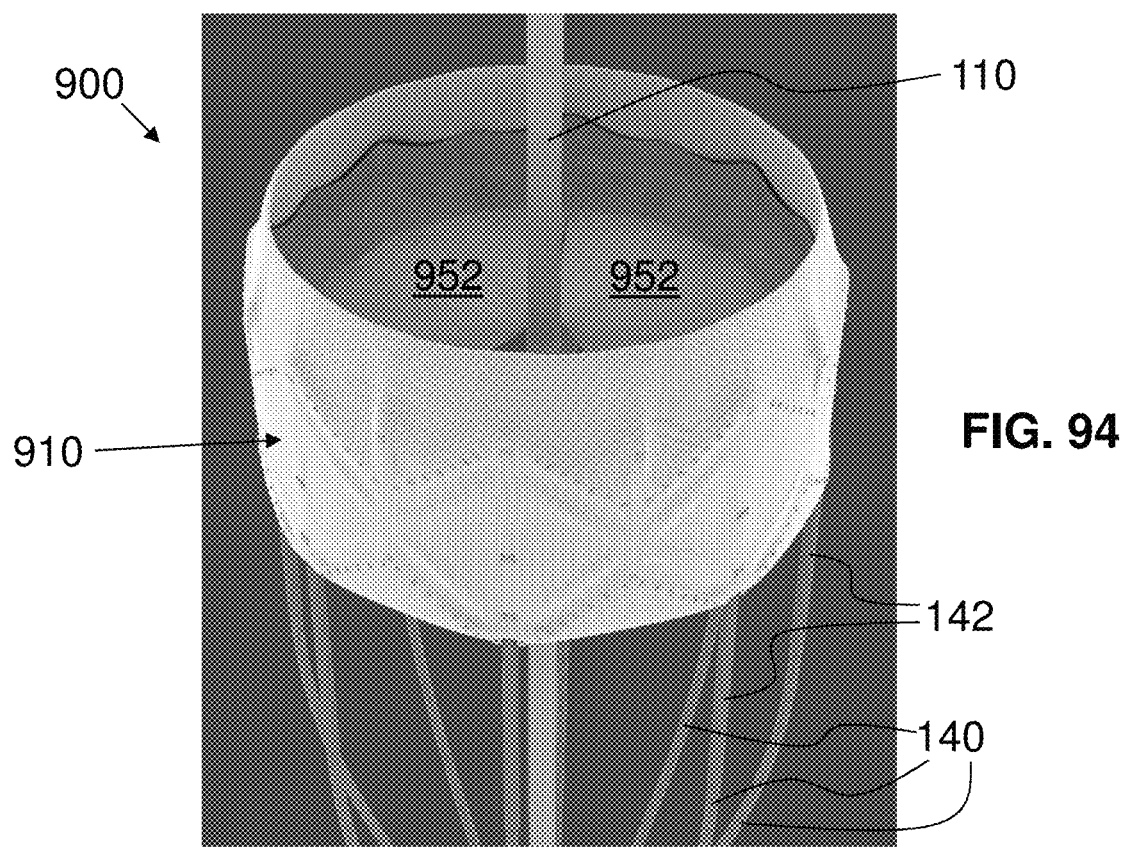
FIG. 94 is a nosecone-side perspective view of another exemplary embodiment of an actively controllable, circular valve replacement implant.
Figure 95:
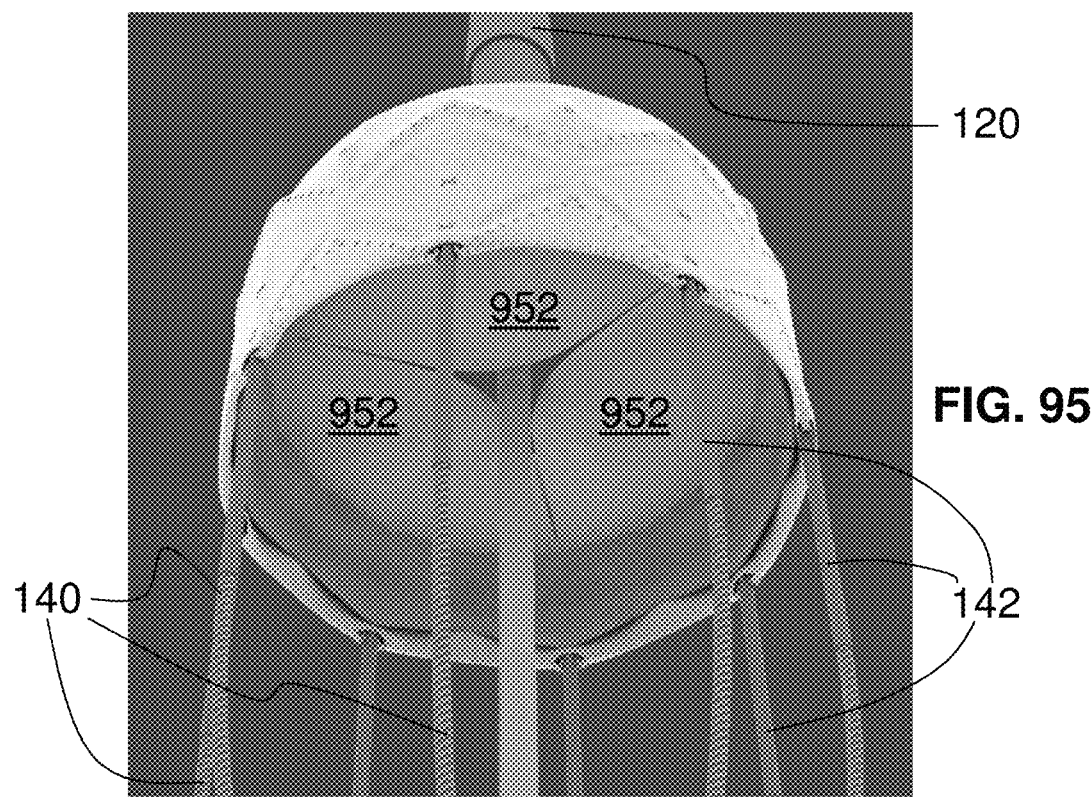
FIG. 95 is an installation-side perspective view of the circular valve replacement implant of FIG. 94.
Figure 96:
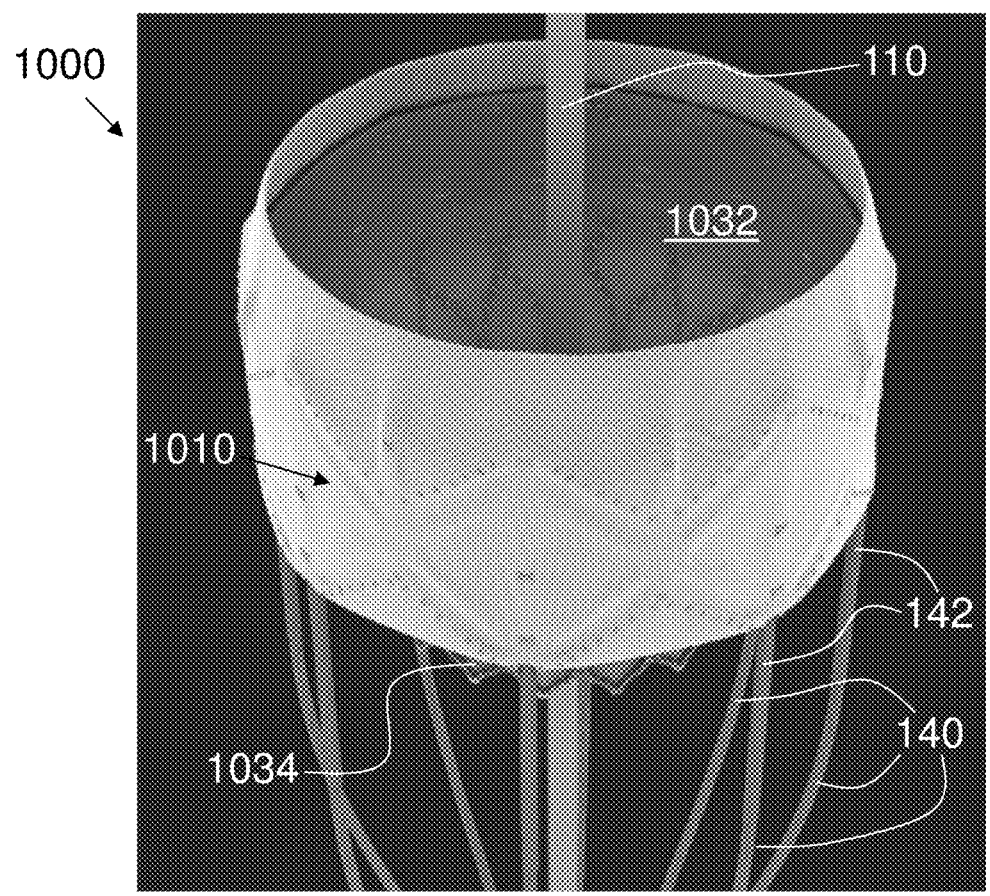
FIG. 96 is a nosecone-side perspective view of another exemplary embodiment of an actively controllable, circular valve replacement implant with a trampoline valve.
Figure 97:
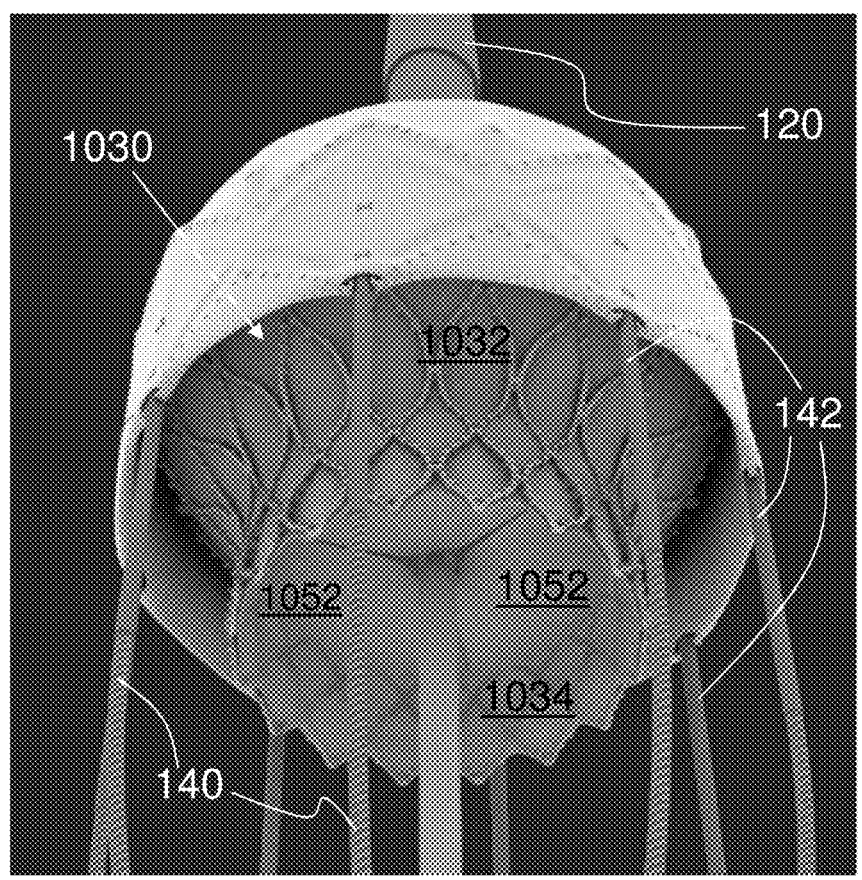
FIG. 97 is an installation-side perspective view of the circular valve replacement implant of FIG. 96.
Figure 98:
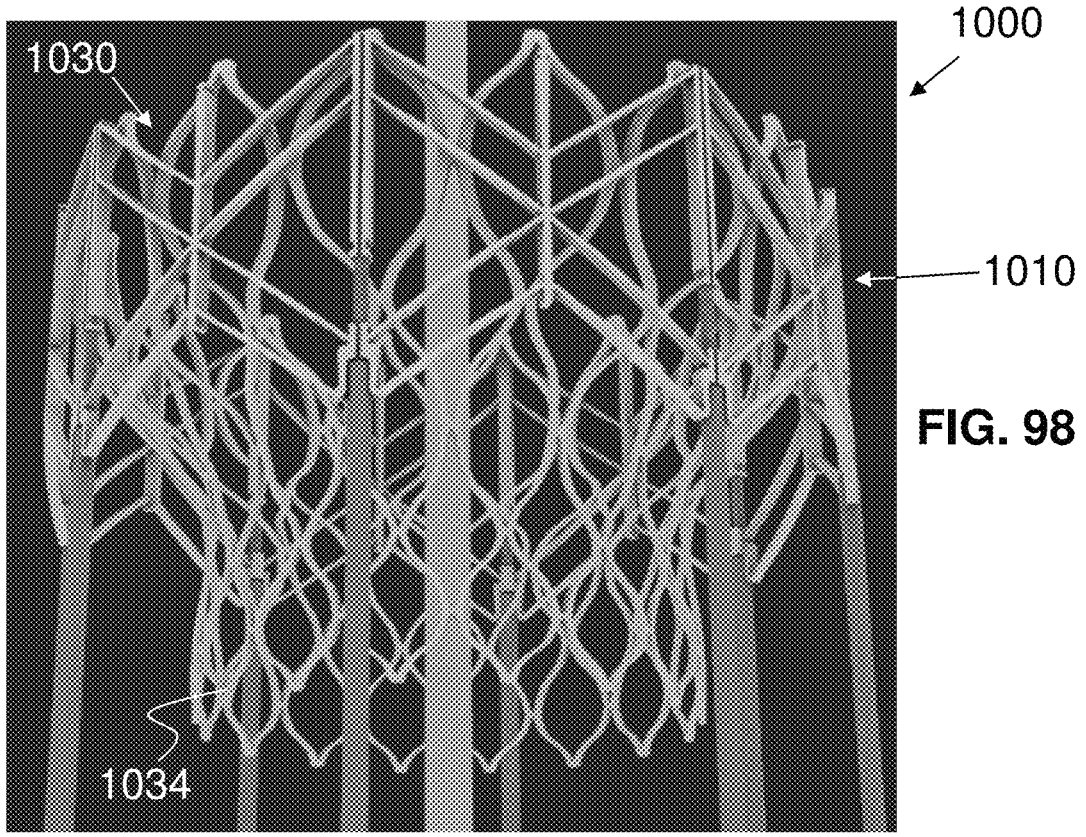
FIG. 98 is an installation-side perspective view of an adjustable stent lattice and valve trampoline lattice of the circular valve replacement implant of FIG. 96.
Figure 99:
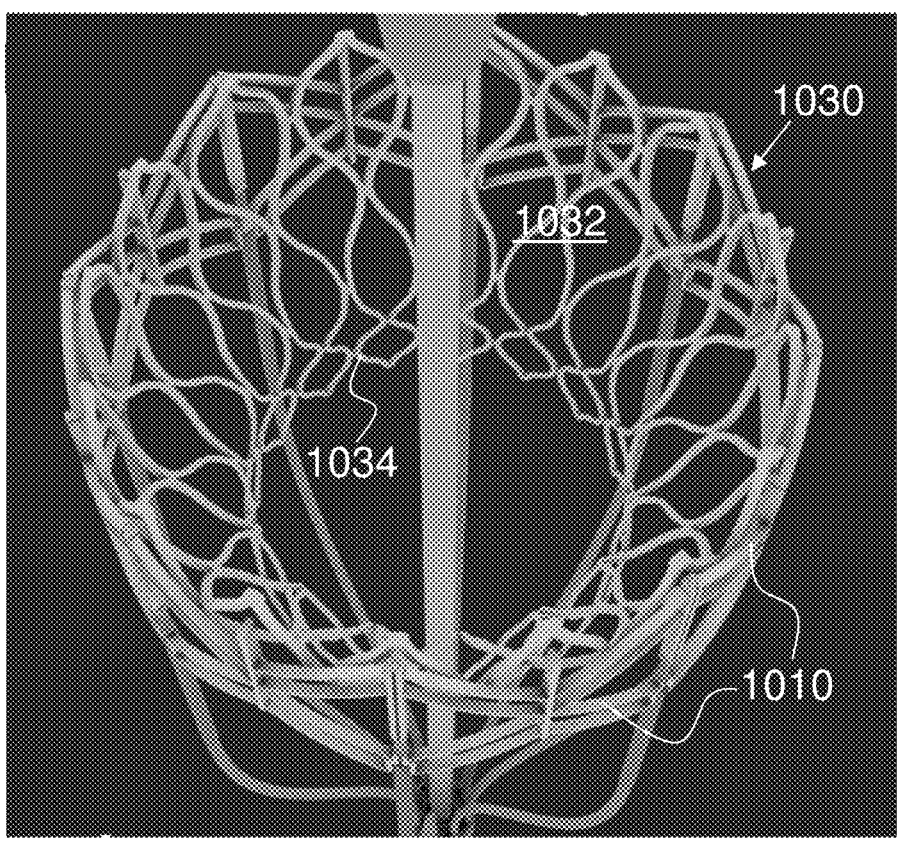
FIG. 99 is a nosecone-side perspective view of the adjustable stent lattice the and valve trampoline lattice of FIG. 98.

A fourth alternative configuration of a circular valve replacement implant 900 is shown in FIGS. 94 and 95. In contrast to the previous exemplary embodiments, the implant 900 has no exterior skirt, has no wall-retaining petals, and does not have the trampoline valve. The implant 900 has an overall circular shape and a tricuspid valve with leaflets 952 attached to the interior of the adjustable stent lattice 910.

A fifth alternative configuration of a circular valve replacement implant 1000 is shown in FIGS. 96 to 99. In contrast to the previous exemplary embodiments, the implant 1000 has a self-expanding valve trampoline lattice 1030 but it does not have an exterior skirt or wall-retaining petals. The trampoline lattice 1030 has an inner circumferential valve portion 1034 on a side where the disconnect lumens 140 project out from the proximal end of the adjustable stent lattice 1010. The expandable outer trampoline portion 1032 is visible from the interior of the implant 1000 in FIG. 96 and the inner circumferential valve portion 1034 is visible in both FIGS. 96 and 97 with the internal leaflets 1052 is visible in FIG. 97. The framework of the implant 1000 is shown without the external coverings and valve material in FIGS. 98 and 99 to expose the adjustable stent lattice 1010 and the trampoline lattice 1030. Because the disconnect lumens 140 and the drive wires 150 connect from the side of the inner circumferential valve portion 1034, the nosecone 120 is on the side opposite the inner circumferential valve portion 1034.

Figure 102:
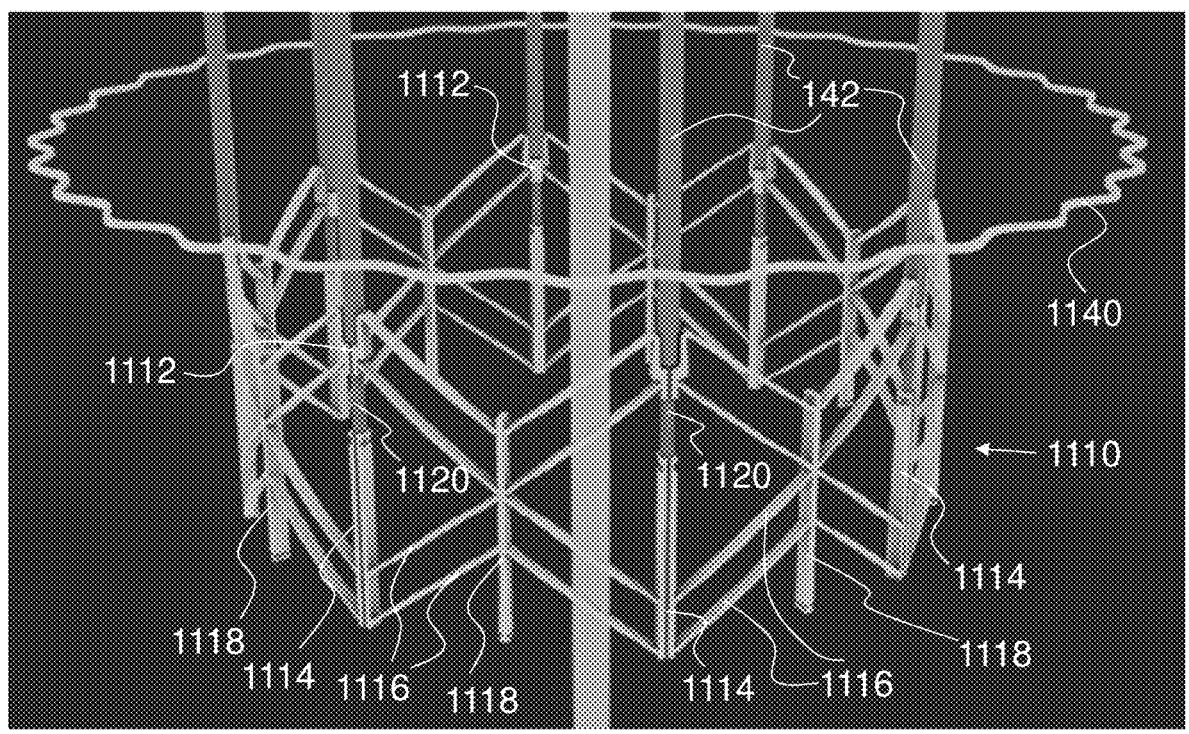
FIG. 102 is a side perspective view of an adjustable stent lattice and an implant skirt frame of the circular valve replacement implant of FIG. 100.

A sixth alternative configuration of a circular valve replacement implant 1100 is shown in FIGS. 100 to 102. In contrast to the previous exemplary embodiments, the implant 1100 has an exterior implant skirt 1140 but it does not have self-expanding valve trampoline lattice or wall-retaining petals. The valve contained within the adjustable stent lattice 1110 has three leaflets 1152, which are shown in FIGS. 100 and 101. The implant 1100 is installed from the side of the adjustable stent lattice 1110 having the implant skirt 1140, the side where the disconnect lumens 140 project out from the proximal end of the adjustable stent lattice 1110. Because the disconnect lumens 140 and the drive wires 150 connect from the side of the implant skirt 1140, the nosecone 120 is on the side opposite the implant skirt 1140, as shown in FIG. 101.

The framework of the implant 1100 is shown without the external coverings and valve material in FIG. 102 to expose the adjustable stent lattice 1110 and the lattice of the skirt 1140, as well as their various components. The implant skirt 1140, in this exemplary embodiment comprises only one part, an outer circumferential ring. This implant skirt 1140 does not connect to the adjustable stent lattice with intervening struts as in some of the above embodiments. The skirt 1140 is made of a material that is self-expanding and has a desired, pre-set shape (such as heat-set nitinol, for example). The adjustable stent lattice 1110 comprises sets of jack screw connectors, each set having a proximal jack strut 1112 and a distal jack strut 1114. Arms 1116 connect each of the proximal and distal jack struts 1112, 1114 to an intermediate strut 1118. Jack screws 1120 connect to the proximal and distal jack struts 1112, 1114 so that, when the jack screw 1120 is turned in one direction, the proximal and distal jack struts 1112, 114 separate from one another and, when the jack screw 1120 is turned in the other opposite direction, the proximal and distal jack struts 1112, 1114 move towards one another. This configuration can be achieved in various ways as described above and, therefore, this is not repeated here.

With such a configuration, rotation of the many jack screws 1120 in the strut-approaching direction causes the proximal and distal jack struts 1112, 1114 to move towards one another and, thereby, push the intermediate struts 1118 (which are disposed parallel to the jack screws 1120) away from the jack screw 1120 in a direction along the circumferential extent of the annulus of the adjustable stent lattice 1110. This relative movement of the intermediate strut 1118 and the jack screw assemblies causes expansion of the adjustable stent lattice 1110 when the proximal and distal jack struts 1112, 1114 move towards one another and causes contraction of the adjustable stent lattice 1110 when the proximal and distal jack struts 1112, 1114 move away from one another. Ideally, all of the jack screws 120 are rotated at the same speed to but such equal movement is not to be considered limiting.

In the exemplary embodiment of the adjustable stent lattice 1110 shown, there are eight pairs of jack struts 1112, 1114 and eight intermediate struts 1118. This number is merely exemplary and there can be, for example, only six of each or any other number desired including any number from 1 to 10. Connecting the pairs of jack struts 1112, 1114 and the intermediate struts 1118 are the laterally extending arms 1116, which, in this exemplary embodiment is two for each of the proximal and distal jack struts 1112, 1114, but this number is not limiting. As the adjustable stent lattice 1110 is either contracted or expanded, the arms 1116 each flex at their two endpoints, one at a respective intermediate strut 1118 and the other at a respective one of a pair of jack struts 1112, 1114. When the adjustable stent lattice 1110 is contracted (e.g., for installation into the delivery sheath 130), the arms 1116 move towards a longitudinal orientation (parallel to the jack screws and to the central axis of the lattice 1110. Conversely, when the adjustable stent lattice 1110 is expanded (e.g., for implantation), the arms 1116 angle away from the respective intermediate strut 1118 and one of the pair of jack struts 1112, 1114 in a circumferential orientation (perpendicular to the jack screws).

A seventh alternative configuration of a circular valve replacement implant 1200 is shown in FIGS. 103 and 104. In contrast to the previous exemplary embodiments, the implant 1200 has an exterior implant skirt 1240 and a self-expanding valve trampoline lattice 1230 but it does not have wall-retaining petals. The trampoline lattice 1230 has an inner circumferential valve portion 1234 on the side of the implant skirt 1240 where the disconnect lumens 140 project out from the proximal end of the adjustable stent lattice 1210. The expandable outer trampoline portion 1232 is visible from the interior of the implant 1200 in FIG. 103 and the inner circumferential valve portion 1234 is visible in FIG. 104 with the internal leaflets 1252 also visible there, three in number in this example. The implant 1200 is installed from the skirt side of the adjustable stent lattice 1210 where the inner circumferential valve portion 1234 exists and the side where the disconnect lumens 140 project out from the proximal end of the adjustable stent lattice 1210. Because the disconnect lumens 140 and the drive wires 150 connect from the side of the inner circumferential valve portion 1234, the nosecone 120 is on the side opposite the inner circumferential valve portion 1234.

In the above embodiments, memory shape and other metallic lattices were described. These lattices can have a material thickness of between 0.6 mm (0.024") and 0.9 mm (0.035") and any number therebetween, in particular between 0.7 mm (0.028") and 0.8 mm (0.032") and any number therebetween.

With mitral valve replacement implants having a trampoline valve, the number of sizes needed to cover the range of patient population is decreased from prior art TAVR replacement valves, which generally requires at least four sizes to be available for use. For the trampoline valves described herein, a 22 mm diameter valve can reside within a valve trampoline lattice having an expanded diameter starting at approximately 25 mm at its smallest to approximately 40 mm at its largest size. A 30 mm diameter valve can reside within a valve trampoline lattice having an expanded diameter starting at approximately 40 mm at its smallest to approximately 55 mm at its largest size. With a valve diameter range of between 25 mm and 55 mm, this means that the herein-described mitral valve implants having valve trampolines can cover the entire range of expected patient population with only two sizes.

The catheter sheaths required to implant these two are approximately 28 Fr to 32 Fr for the 25 mm to 40 mm size and 32 Fr to 35 Fr for the 40 mm to 55 mm size. Well within the desired range of catheters for such valve replacement procedures. It is further noted that if porcine pericardium is used for the valve leaflets, the size of the delivery sheath can be reduced, in particular, to 25 Fr to 29 Fr and 29 to 32 Fr, respectively.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The foregoing description and accompanying drawings illustrate the principles, exemplary embodiments, and modes of operation of the systems, apparatuses, and methods. However, the systems, apparatuses, and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the systems, apparatuses, and methods as defined by the following claims.

What is claimed is:

1. A method for implanting a replacement mitral valve, comprising:
    contracting a replacement mitral valve to a reduced implantation size with a delivery system having drive wires, the replacement mitral valve having a self-expanding inner lattice and a forcibly-expanding outer lattice, wherein the outer lattice has an adjustable assembly with adjustable elements operatively connected to the drive wires such that, when the adjustable elements are adjusted by the drive wires, a configuration change in at least a portion of the replacement mitral valve occurs;
    inserting the contracted replacement mitral valve into a native mitral valve annulus in which the replacement mitral valve is to be implanted;
    allowing the self-expanding inner lattice to self-expand from the reduced implantation size to a functional size, the self-expanding inner lattice having an inflow end portion and an outflow end portion, the outflow end portion having a plurality of leaflets coupled thereto;
    rotating the drive wires with the delivery system to forcibly expand the forcibly-expanding outer lattice into the native mitral valve annulus, the forcibly-expanding outer lattice having a first end portion and a second end portion, the second end portion of the forcibly-expanding outer lattice being coupled to the inflow end portion of the self-expanding lattice;
    while rotating the drive wires, determining with the delivery system a torque applied to the drive wires; and
    stopping rotation of the drive wires based upon a value of the determined torque, wherein the outflow end portion of the self-expanding inner lattice is disposed radially inwardly from the second end portion of the forcibly-expanding outer lattice after stopping rotation of the drive wires.

2. The method of claim 1, wherein the replacement mitral valve is made of a shape-memory material set to a given shape.

3. The method of claim 1, wherein prior to rotating the drive wires, the method further comprises allowing the forcibly-expanding outer lattice of the replacement mitral valve to self-expand from the reduced implantation size to a partially expanded state.

4. A method of implanting a replacement mitral valve, comprising:
    expanding a replacement mitral valve to a first expanded configuration, wherein the replacement mitral valve comprises a force-expanding mitral valve lattice and a self-expanding valve trampoline lattice, wherein the mitral valve lattice has an inflow end portion and an outflow end portion, wherein the valve trampoline lattice has a first end portion and a second end portion, and wherein the first end portion of the valve trampoline lattice is attached to the outflow end portion of the mitral valve lattice; and
    rotating a plurality of jack screws connected to the mitral valve lattice, wherein the jack screws are configured to expand the mitral valve lattice from the first expanded configuration to a second expanded configuration in which the second end portion of the valve trampoline lattice is disposed radially inwardly from the outflow end portion of the mitral valve lattice.

5. The method of claim 4, wherein the first expanded configuration is one of circular and D-shaped.

6. The method of claim 5, wherein a valve portion of the valve trampoline lattice comprises a cylindrical shape and remains in the first expanded configuration when the mitral valve lattice expands to the second expanded configuration, and wherein the valve portion of the valve trampoline lattice is configured to support a prosthetic valve having a plurality of leaflets.

7. The method of claim 6, wherein a trampoline portion of the valve trampoline lattice expands from the first expanded configuration to the second expanded configuration together with the mitral valve lattice, and wherein the trampoline portion of the valve trampoline lattice is attached to the outflow end portion of the mitral valve lattice.

8. The method of claim 4, further comprising rotating the jack screws to compress the mitral valve lattice from the second expanded configuration to the first expanded configuration.

9. The method of claim 4, wherein the mitral valve lattice is made of a shape memory material and is shape-set to the first expanded configuration.

10. The method of claim 4, wherein when the mitral valve lattice is in the second expanded configuration, the valve trampoline lattice has a cylindrical portion supporting valve leaflets and a D-shaped portion extending between the cylindrical portion and the mitral valve lattice.

11. The method of claim 10, wherein the valve leaflets have an inflow side and the D-shaped portion is located on the inflow side of the valve leaflets.

12. The method of claim 4, wherein the mitral valve lattice comprises a D-shaped portion when the mitral valve lattice is in the second expanded configuration.

13. The method of claim 4, further comprising expanding a skirt lattice, wherein the skirt lattice has an outflow end portion that extends radially outwardly relative to the mitral valve lattice.

14. The method of claim 4, further comprising expanding a skirt lattice, wherein the skirt lattice has an inflow end portion comprising wall-retaining wires extending radially outwardly relative to the mitral valve lattice.

15. A method of implanting a replacement mitral valve, comprising:
    advancing a replacement mitral valve through a patient's vasculature with the replacement mitral valve retained in a delivery configuration by a sheath of a delivery system;
    exposing the replacement mitral valve from the sheath;
    expanding the replacement mitral valve from the delivery configuration to a first expanded configuration, wherein the replacement mitral valve includes a first lattice and a second lattice, the second lattice having an inner portion configured for supporting a valve member and an outer portion attached to the first lattice;
    rotating a plurality of jack screws connected to the first lattice, wherein the jack screws are configured to expand the first lattice from the first expanded configuration to a second expanded configuration, wherein the second expanded configuration is radially larger than the first expanded configuration, and wherein the first lattice contacts native heart valve tissue in the second expanded configuration;
    rotating the jack screws to contract the first lattice from the second expanded configuration to a third expanded configuration, wherein the first lattice at least partially disengages the native heart valve tissue in the third expanded configuration;
    repositioning the replacement mitral valve relative to native heart valve tissue; and
    rotating the jack screws to expand the first lattice from the third expanded configuration to a fourth expanded configuration, wherein the first lattice contacts the native heart valve tissue in the fourth expanded configuration, and wherein the inner portion of the second lattice is disposed radially inwardly from the first lattice when the first lattice is in the fourth expanded configuration.

16. The method of claim 15, wherein the third expanded configuration is radially larger than the first expanded configuration.

17. The method of claim 15, wherein the third expanded configuration is the same size radially as the first expanded configuration.

18. The method of claim 15, wherein the inner portion of the second lattice has a constant diameter when the first lattice is in the first expanded configuration, the second expanded configuration, the third expanded configuration, and the fourth expanded configuration.

19. The method of claim 15, wherein a diameter of the outer portion of the second lattice varies with the diameter of the first lattice as the first lattice moves between the first expanded configuration, the second expanded configuration, the third expanded configuration, and the fourth expanded configuration.

20. The method of claim 15, wherein the inner portion of the second lattice is disposed radially inwardly from the first lattice when the first lattice is in the second expanded configuration.

* * * * *